(12) United States Patent
Kupper

(10) Patent No.: US 12,319,970 B2
(45) Date of Patent: Jun. 3, 2025

(54) METHODS FOR IDENTIFYING PROGRESSION OF A PRIMARY MELANOMA

(71) Applicant: The Brigham and Women's Hospital, Inc., Boston, MA (US)

(72) Inventor: Thomas S. Kupper, Belmont, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 17/956,050

(22) Filed: Sep. 29, 2022

(65) Prior Publication Data

US 2023/0090450 A1    Mar. 23, 2023

Related U.S. Application Data

(63) Continuation of application No. 16/838,926, filed on Apr. 2, 2020, now abandoned.

(60) Provisional application No. 62/828,064, filed on Apr. 2, 2019.

(51) Int. Cl.
    *C12Q 1/6886*    (2018.01)

(52) U.S. Cl.
    CPC ...... *C12Q 1/6886* (2013.01); *C12Q 2600/118* (2013.01); *C12Q 2600/156* (2013.01); *G01N 2800/52* (2013.01); *G01N 2800/54* (2013.01); *G01N 2800/56* (2013.01)

(58) Field of Classification Search
    CPC ............ C12Q 1/6886; C12Q 2600/106; C12Q 2600/118; G01N 2800/52; G01N 2800/54; G01N 2800/56
    See application file for complete search history.

(56) References Cited

U.S. PATENT DOCUMENTS

| | | |
|---|---|---|
| 5,811,097 A | 9/1998 | Allison et al. |
| 5,855,887 A | 1/1999 | Allison et al. |
| 6,051,227 A | 4/2000 | Allison et al. |
| 6,682,736 B1 | 1/2004 | Hanson et al. |
| 6,984,720 B1 | 1/2006 | Korman et al. |
| 7,605,238 B2 | 10/2009 | Korman et al. |
| 7,741,345 B2 | 6/2010 | Cannizzaro et al. |
| 8,008,449 B2 | 8/2011 | Korman et al. |
| 8,552,156 B2 | 10/2013 | Takayanagi et al. |
| 8,591,900 B2 | 11/2013 | Barrett et al. |
| 9,073,994 B2 | 7/2015 | Honjo et al. |
| 9,150,905 B2 | 10/2015 | Robins et al. |
| 9,371,558 B2 | 6/2016 | Robins et al. |

(Continued)

FOREIGN PATENT DOCUMENTS

| | | |
|---|---|---|
| EP | 1141028 | 10/2001 |
| EP | 1212422 | 6/2002 |

(Continued)

OTHER PUBLICATIONS

Ahmadian et al., "Single-nucleotide polymorphism analysis by pyrosequencing," Analytical Biochemistry, Apr. 10, 2000, 280(1):103-10.

(Continued)

*Primary Examiner* — Diana B Johannsen
(74) *Attorney, Agent, or Firm* — Fish & Richardson P.C.

(57) ABSTRACT

Methods of using T cell frequency (TCFR) in melanoma, e.g., as determined by high throughput DNA sequencing of the TCRB gene, as a predictor of disease progression and survival in patients with primary melanoma, and to select and treat subjects.

7 Claims, 40 Drawing Sheets

(56) References Cited

U.S. PATENT DOCUMENTS

| | | |
|---|---|---|
| 2003/0165499 A1 | 9/2003 | Chu et al. |
| 2004/0120948 A1 | 6/2004 | Mikayama et al. |
| 2005/0048542 A1 | 3/2005 | Baker et al. |
| 2007/0148163 A1 | 6/2007 | Takahashi et al. |
| 2009/0025274 A1 | 1/2009 | Lail |
| 2011/0271358 A1 | 11/2011 | Freeman et al. |
| 2013/0011405 A1 | 1/2013 | Luqman et al. |
| 2013/0022623 A1 | 1/2013 | Karsunky et al. |
| 2015/0086574 A1 | 3/2015 | Karsunky et al. |
| 2016/0257749 A1 | 9/2016 | Lifke et al. |
| 2016/0257758 A1 | 9/2016 | Gray et al. |
| 2016/0303124 A1 | 10/2016 | Webster et al. |
| 2016/0354409 A1 | 12/2016 | Wang et al. |
| 2017/0022273 A1 | 1/2017 | Zhou et al. |
| 2017/0058033 A1 | 3/2017 | Ludwig et al. |
| 2017/0101472 A1 | 4/2017 | Ullman et al. |
| 2017/0114135 A1 | 4/2017 | Codarri-Deak et al. |
| 2017/0290914 A1 | 10/2017 | Liang et al. |
| 2017/0313783 A1 | 11/2017 | Karsunky et al. |
| 2017/0333384 A1 | 11/2017 | Desai et al. |
| 2017/0334995 A1 | 11/2017 | Zettl et al. |
| 2018/0016336 A1 | 1/2018 | Schebye et al. |
| 2018/0072804 A1 | 3/2018 | Lifke et al. |
| 2018/0230431 A1 | 8/2018 | Bi et al. |
| 2018/0251549 A1 | 9/2018 | Gray et al. |
| 2018/0251767 A1 | 9/2018 | Schroff et al. |
| 2018/0298097 A1 | 10/2018 | Schebye et al. |
| 2018/0326054 A1 | 11/2018 | Deak et al. |
| 2020/0040082 A1 | 2/2020 | Piasecki et al. |
| 2020/0062859 A1 | 2/2020 | Piasecki et al. |

FOREIGN PATENT DOCUMENTS

| | | |
|---|---|---|
| WO | WO 2002/088186 | 11/2002 |
| WO | WO 2007/124299 | 11/2007 |
| WO | WO 2011/123489 | 10/2011 |
| WO | WO 2012/062831 | 5/2012 |
| WO | WO 2012/111762 | 8/2012 |
| WO | WO 2012/149356 | 8/2012 |
| WO | WO 2013/079174 | 6/2013 |
| WO | WO 2014/070934 | 5/2014 |
| WO | WO 2014/195852 | 12/2014 |
| WO | WO 2016/007235 | 1/2016 |
| WO | WO 2016/061142 | 4/2016 |
| WO | WO 2016/071448 | 5/2016 |
| WO | WO 2017/184607 | 10/2017 |
| WO | WO 2018/102567 | 6/2018 |

OTHER PUBLICATIONS

American Joint Committee on Cancer, "Malignant melanoma of the skin," AJCC Cancer Staging Manual, 5th ed., Lippincott-Raven, 1997, 163-70.

Andrews et al., "LAG 3 (CD 223) as a cancer immunotherapy target," Immunological Reviews, Mar. 4, 2017, 276(1):80-96.

Antonia et al., "Immunotherapy: beyond anti-PD-1 and anti-PD-L1 therapies," American Society of Clinical Oncology Educational Book, May 2016, 36:e450-8.

Azimi et al., "Tumor-infiltrating lymphocyte grade is an independent predictor of sentinel lymph node status and survival in patients with cutaneous melanoma," Journal of Clinical Oncology, Jul. 20, 2012, 30(21):2678-83.

Barnhill et al., "Predicting a five-year outcome for patients with cutaneous melanoma in a population-based study," Cancer: Interdisciplinary International Journal of the American Cancer Society, Aug. 1, 1996, 78(3):427-32.

Bernard et al., "Real-time PCR technology for cancer diagnostics," Clinical Chemistry, Aug. 1, 2002, 48(8):1178-85.

Bethune et al., "T cell-mediated cancer immunotherapy: progress and challenges," Current Opinion in Biotechnology, Dec. 1, 2017, 48:142-52.

Bhatia et al., "Treatment of metastatic melanoma: an overview," Oncology, May 2009, 23(6):488-96.

Bianchi et al., "A serum circulating miRNA diagnostic test to identify asymptomatic high-risk individuals with early stage lung cancer," EMBO Molecular Medicine, Aug. 2011, 3(8):495-503.

Burton et al., "Prognostic significance of tumor infiltrating lymphocytes in melanoma," The American Surgeon, Feb. 1, 2011, 77(2):188-92.

Camisaschi et al., "Immune cells in the melanoma microenvironment hold information for prediction of the risk of recurrence and response to treatment," Expert Review of Molecular Diagnostics, Jun. 10, 2014, 14(6):643-46.

Carlson et al., "Using synthetic templates to design an unbiased multiplex PCR assay, " Nature Communications, Oct. 25, 2013, 4(1):1-9.

Cha et al., "Improved survival with T cell clonotype stability after anti-CTLA-4 treatment in cancer patients," Science Translational Medicine, May 28, 2014, 6(238):238ra70, 22 pages.

Church et al., "Tumor microenvironment and immunotherapy: the whole picture is better than a glimpse," Immunity, Oct. 20, 2015, 43(4):631-3.

Clark Jr. et al., "Model predicting survival in stage I melanoma based on tumor progression," JNCI: Journal of the National Cancer Institute, Dec. 20, 1989, 81(24):1893-904.

Clemente et al., "Prognostic value of tumor infiltrating lymphocytes in the vertical growth phase of primary cutaneous melanoma," Cancer: Interdisciplinary International Journal of the American Cancer Society, Apr. 1, 1996, 77(7):1303-10.

Diehl et al., "BEAMing: single-molecule PCR on microparticles in water-in-oil emulsions," Nature Methods, Jul. 2006, 3(7):551-9.

Donizy et al., "Paucity of tumor-infiltrating lymphocytes is an unfavorable prognosticator and predicts lymph node metastases in cutaneous melanoma patients," Anticancer Research, Jan. 1, 2015, 35(1):351-8.

Duhen et al., "Co-expression of CD39 and CD103 identifies tumor-reactive CD8 T cells in human solid tumors," Nature Communications, Jul. 13, 2018, 9(1):1-3.

Ekins et al., "Microarrays: their origins and applications," Trends in Biotechnology, Jun. 1999, 17(6):217-8.

Elith et al., "A working guide to boosted regression trees," Journal of Animal Ecology, Jul. 2008, 77(4):802-13.

Elsaeßer et al., "Prognosis of sentinel node staged patients with primary cutaneous melanoma," PLoS One, Jan. 19, 2012, 7(1):e29791, 8 pages.

EP Extended Search Report in European Appln. No. 20785366.4, dated Nov. 16, 2022, 8 pages.

Gata et al., "Tumor infiltrating lymphocytes as a prognostic factor in malignant melanoma," Review of the Literature, J. Buon, May 1, 2017, 22(3):592-8.

Gershenwald et al., "Melanoma staging: evidence-based changes in the American Joint Committee on Cancer eighth edition cancer staging manual," CA: A Cancer Journal for Clinicians, Nov. 2017, 67(6):472-92.

Harjunpää et al., "TIGIT as an emerging immune checkpoint," Clinical & Experimental Immunology, May 2020, 200(2):108-19.

Hayward et al., "Whole-genome landscapes of major melanoma subtypes," Nature, May 2017, 545(7653):175-80.

Hogan et al., "Melanoma immunotherapy: next-generation biomarkers," Frontiers in Oncology, May 29, 2018, 8:178.

Huang et al., "A single dose of neoadjuvant PD-1 blockade predicts clinical outcomes in resectable melanoma," Nature Medicine, Mar. 2019, 25(3):454-61.

Inoue et al., "Intratumoral expression levels of PD-L1, GZMA, and HLA-A along with oligoclonal T cell expansion associate with response to nivolumab in metastatic melanoma, " Oncoimmunology, Sep. 1, 2016, 5(9), 8 pages.

Keane et al., "The T-cell receptor repertoire influences the tumor microenvironment and is associated with survival in aggressive B-cell lymphoma, " Clinical Cancer Research, Apr. 2017, 23(7):1820-8.

Kirsch et al., "TCR sequencing facilitates diagnosis and identifies mature T cells as the cell of origin in CTCL," Science Translational Medicine, Oct. 7, 2015, 7(308):308ra158.

(56) References Cited

OTHER PUBLICATIONS

Kou et al., "T-cell receptor VB repertoire CDR3 length diversity differs within CD45RA and CD45RO T-cell subsets in healthy and human immunodeficiency virus-infected children" Clinical and Diagnostic laboratory Immunology, Nov. 1, 2000,7(6):953-9.
Kruper et al., "Predicting sentinel node status in AJCC stage I/II primary cutaneous melanoma," Cancer, Nov. 15, 2006, 107(10):2436-45.
Krynitz et al., "Cutaneous malignant melanoma in the Swedish organ transplantation cohort: a study of clinicopathological characteristics and mortality," Journal of the American Academy of Dermatology, Jul. 1, 2015, 73(1):106-13.
Ladányi et al., "T-cell activation marker expression on tumor-infiltrating lymphocytes as prognostic factor in cutaneous malignant melanoma," Clinical Cancer Research, Jan. 15, 2004, 10(2):521-30.
Larkin et al., "Combined nivolumab and ipilimumab or monotherapy in untreated melanoma," New England Journal of Medicine, Jul. 2, 2015, 373(1):23-34.
Lawrence et al., "Mutational heterogeneity in cancer and the search for new cancer-associated genes," Nature, Jul. 2013, 499(7457):214-8.
Leonardi et al., "Cutaneous melanoma: From pathogenesis to therapy," International Journal of Oncology, Apr. 1, 2018, 52(4):1071-80.
Luke et al., "Chemotherapy in the management of advanced cutaneous malignant melanoma," Clinics in Dermatology, May 1, 2013, 31(3):290-7.
Luke et al., "Targeted agents and immunotherapies: optimizing outcomes in melanoma," Nature Reviews Clinical oncology, Aug. 2017, 14(8):463-82.
Macbeath et al., "Printing proteins as microarrays for high-throughput function determination," Science, Sep. 8, 2000, 289(5485):1760-3.
Mandala et al., "Clinical and histopathological risk factors to predict sentinel lymph node positivity, disease-free and overall survival in clinical stages I-II AJCC skin melanoma: outcome analysis from a single-institution prospectively collected database," European Journal of Cancer, Sep. 1, 2009, 45(14):2537-45.
Månsson-Brahme et al., "Prognostic factors in thin cutaneous malignant melanoma," Cancer, May 1, 1994, 73(9):2324-32.
Matthews et al., "Epidemiology of melanoma," In Cutaneous Melanoma: Etiology and Therapy, Ward & Farma, Nov. 30, 2017, 3-22.
Mcshane et al., "Reporting recommendations for tumor marker prognostic studies (REMARK)," Journal of the National Cancer Institute, Aug. 17, 2005, 97(6):1180-4.
Miranda et al., "Nucleic acids within urinary exosomes/microvesicles are potential biomarkers for renal disease," Kidney International, Jul. 2, 2010, 78(2):191-9.
Nordström et al., "Direct analysis of single-nucleotide polymorphism on double-stranded DNA by pyrosequencing," Biotechnology and Applied Biochemistry, Apr. 2000, 31(2):107-12.
Nsengimana et al., "β-Catenin-mediated immune evasion pathway frequently operates in primary cutaneous melanomas," The Journal of Clinical Investigation, May 1, 2018, 128(5):2048-63.
Ott et al., "An immunogenic personal neoantigen vaccine for patients with melanoma," Nature, Jul. 2017, 547(7662):217-21.
Park et al., "Clinicopathological significance of intratumoral and peritumoral lymphocytes and lymphocyte score based on the histologic subtypes of cutaneous melanoma," Oncotarget, Feb. 28, 2017, 8(9):14759-69.
Pasquali et al., "Systemic treatments for metastatic cutaneous melanoma," Cochrane Database of Systematic Reviews, Feb. 2018(2), 16 pages.
Pavri et al., "Malignant melanoma: beyond the basics," Plastic and Reconstructive Surgery, Aug. 1, 2016, 138(2):330e-40e.
PCT International Preliminary Report on Patentability in International Appln. No. PCT/US2020/026455, dated Oct. 14, 2021, 8 pages.
PCT International Search Report and Written Opinion in International Appln. No. PCT/US2020/026455, dated Jun. 16, 2020, 10 pages.
Postow et al., "Peripheral T cell receptor diversity is associated with clinical outcomes following ipilimumab treatment in metastatic melanoma," Journal for Immunotherapy of Cancer, Dec. 1, 2015, 3(1):23, 7 pages.
Prieto et al., "CTLA-4 blockade with ipilimumab: long-term follow-up of 177 patients with metastatic melanoma," Clinical Cancer Research, Apr. 1, 2012, 18(7):2039-47.
Rastrelli et al., "Melanoma: epidemiology, risk factors, pathogenesis, diagnosis and classification, " In Vivo, Nov. 1, 2014, 28(6):1005-11.
Riaz et al., "Tumor and microenvironment evolution during immunotherapy with nivolumab," Cell, Nov. 2, 2017, 171(4):934-49.
Robert et al., "Distinct immunological mechanisms of CTLA-4 and PD-1 blockade revealed by analyzing TCR usage in blood lymphocytes," Oncoimmunology, Jun. 1, 2014, 3(6):e29244, 2 pages.
Robins et al., "Comprehensive assessment of T-cell receptor β-chain diversity in αβ T cells," Blood, The Journal of the American Society of Hematology, Nov. 5, 2009, 114(19):4099-107.
Rodríguez-Cerdeira et al., "Advances in immunotherapy for melanoma: a comprehensive review," Mediators of Inflammation, Jan. 1, 2017, vol. 2017, 15 pages.
Roh et al., "Integrated molecular analysis of tumor biopsies on sequential CTLA-4 and PD-1 blockade reveals markers of response and resistance," Science Translational Medicine, Mar. 1, 2017, 9(379), 13 pages.
Rosato et al., "Virus-specific memory T cells populate tumors and can be repurposed for tumor immunotherapy, " Nature Communications, Feb. 4, 2019, 10(1):1-9.
R-Project.org, "R: A language and environment for statistical computing. R Foundation for Statistical Computing," retrieved from URL=<https://www.gbif.org/tool/81287/r-a-language-and-environment-for-statistical-computing> on Sep. 2, 2019, Vienna, Austria, 2017, 2 pages.
Saldanha et al., "A novel numerical scoring system for melanoma tumour infiltrating lymphocytes has better prognostic value than standard scoring," The American Journal of Surgical Pathology, Jul. 2017, 41(7):906-14.
Scheper et al., "Low and variable tumor reactivity of the intratumoral TCR repertoire in human cancers," Nature Medicine, Jan. 2019, 25(1):89-94.
Shaikh et al., "Melanoma thickness and survival trends in the United States, 1989-2009," JNCI: Journal of the National Cancer Institute, Jan. 1, 2016, 108(1), 7 pages.
Shain et al., "From melanocytes to melanomas," Nature Reviews Cancer, Jun. 2016, 16(6):345-58.
Simoni et al., "Bystander CD8+ T cells are abundant and phenotypically distinct in human tumour infiltrates," Nature, May 2018, 557(7706):575-9.
Snyder et al., "Genetic basis for clinical response to CTLA-4 blockade in melanoma," New England Journal of Medicine, Dec. 4, 2014, 371(23):2189-99.
Storz, "Intellectual property issues of immune checkpoint inhibitors," Mabs, Jan. 2, 2016, 8(1):10-26.
Tang et al., "Primary cerebral malignant melanoma: a case report with literature review," Medicine, Jan. 2017, 96(4), 6 pages.
Tanner et al., "The humoral immune response to BCG vaccination," Frontiers in Immunology, 2019, 10:1317, 18 pages.
Tarhini et al., "CTLA-4 blockade: therapeutic potential in cancer treatments," OncoTargets and Therapy, 2010, 3:15, 25 pages.
Tarhini et al., "Neoadjuvant ipilimumab (3 mg/kg or 10 mg/kg) and high dose IFN-β2b in locally/regionally advanced melanoma: safety, efficacy and impact on T-cell repertoire," Journal for Immunotherapy of Cancer, Dec. 1, 2018, 6(1):112, 10 pages.
Taylor et al., "The origin, function, and diagnostic potential of RNA within extracellular vesicles present in human biological fluids," Frontiers in Genetics, Jul. 30, 2013, 4:142, 12 pages.
Taylor et al., "Tumor-infiltrating lymphocytes predict sentinel lymph node positivity in patients with cutaneous melanoma," Journal of Clinical Oncology, Mar. 1, 2007, 25(7):869-75.
Thomas et al., "Tumor-infiltrating lymphocyte grade in primary melanomas is independently associated with melanoma-specific

(56) References Cited

OTHER PUBLICATIONS survival in the population-based genes, environment and melanoma study," Journal of Clinical Oncology, Nov. 20, 2013, 31(33), 4252-9.

Thörn et al., "Clinical and histopathologic predictors of survival in patients with malignant melanoma: a population-based study in Sweden," JNCI: Journal of the National Cancer Institute, May 18, 1994, 86(10):761-9.

Tumeh et al., "PD-1 blockade induces responses by inhibiting adaptive immune resistance," Nature, Nov. 2014, 515(7528):568-71.

Tuthill et al., "Risk assessment in localized primary cutaneous melanoma: a Southwest Oncology Group study evaluating nine factors and a test of the Clark logistic regression prediction model," American Journal of Clinical Pathology, Oct. 1, 2002, 118(4):504-11.

Van Houdt et al., "Favorable outcome in clinically stage II melanoma patients is associated with the presence of activated tumor infiltrating T-lymphocytes and preserved MHC class I antigen expression," International Journal of Cancer, Aug. 1, 2008, 123(3):609-15.

Vasaturo et al., "T-cell landscape in a primary melanoma predicts the survival of patients with metastatic disease after their treatment with dendritic cell vaccines," Cancer Research, Jun. 15, 2016, 76(12):3496-506.

Yang et al., "Detection of tumor cell-specific mRNA and protein in exosome-like microvesicles from blood and saliva," PloS one, Nov. 14, 2014, 9(11):e110641, 10 pages.

Yang et al., "Insights into local tumor microenvironment immune factors associated with regression of cutaneous melanoma metastases by *Mycobacterium bovis* bacille Calmette-Guérin," Frontiers in Oncology, Apr. 5, 2017, 7:61, 15 pages.

Yde et al., "Mucosal melanoma: a literature review," Current Oncology Reports, Mar. 1, 2018, 20(3):28, 10 pages.

Yusko et al., "Association of tumor microenvironment T-cell repertoire and mutational load with clinical outcome after sequential checkpoint blockade in melanoma," Cancer Immunology Research, Mar. 1, 2019, 7(3):458-65.

Pruessmann et al., "Molecular analysis of primary melanoma T cells identifies patients at risk for metastatic recurrence," Nature Cancer, Feb. 2020, 1(2):197, 35 pages.

Analysis of Deviance for Predicting 5-yr PFS

Model superiority when TCFr (</≥ 20%) is added to histopathological feature

|  | Loglikelihood values | | Chi-square |
|---|---|---|---|
|  | without TCFr | with TCFr | p-value |
| Thickness | -573.12 | -564.43 | 3.08E-5 |
| Ulceration | -574.61 | -562.35 | 7.36E-7 |
| Mitotic Rate | -573.58 | -564.05 | 1.26E-5 |
| Nodal Disease | -566.97 | -556.9 | 7.24E-6 |

|  | Low TCFr | High TCFr | Discrepancy |
|---|---|---|---|
| Absent | 24 | 1 | 4% |
| Non-brisk | 73 | 29 | 28% |
| Brisk | 12 | 14 | 54% |

|  | Low TCFr | High TCFr | Discrepancy |
|---|---|---|---|
| 0 | 24 | 1 | 4% |
| 1 | 57 | 9 | 14% |
| 2 | 19 | 25 | 43% |
| 3 | 9 | 9 | 50% |

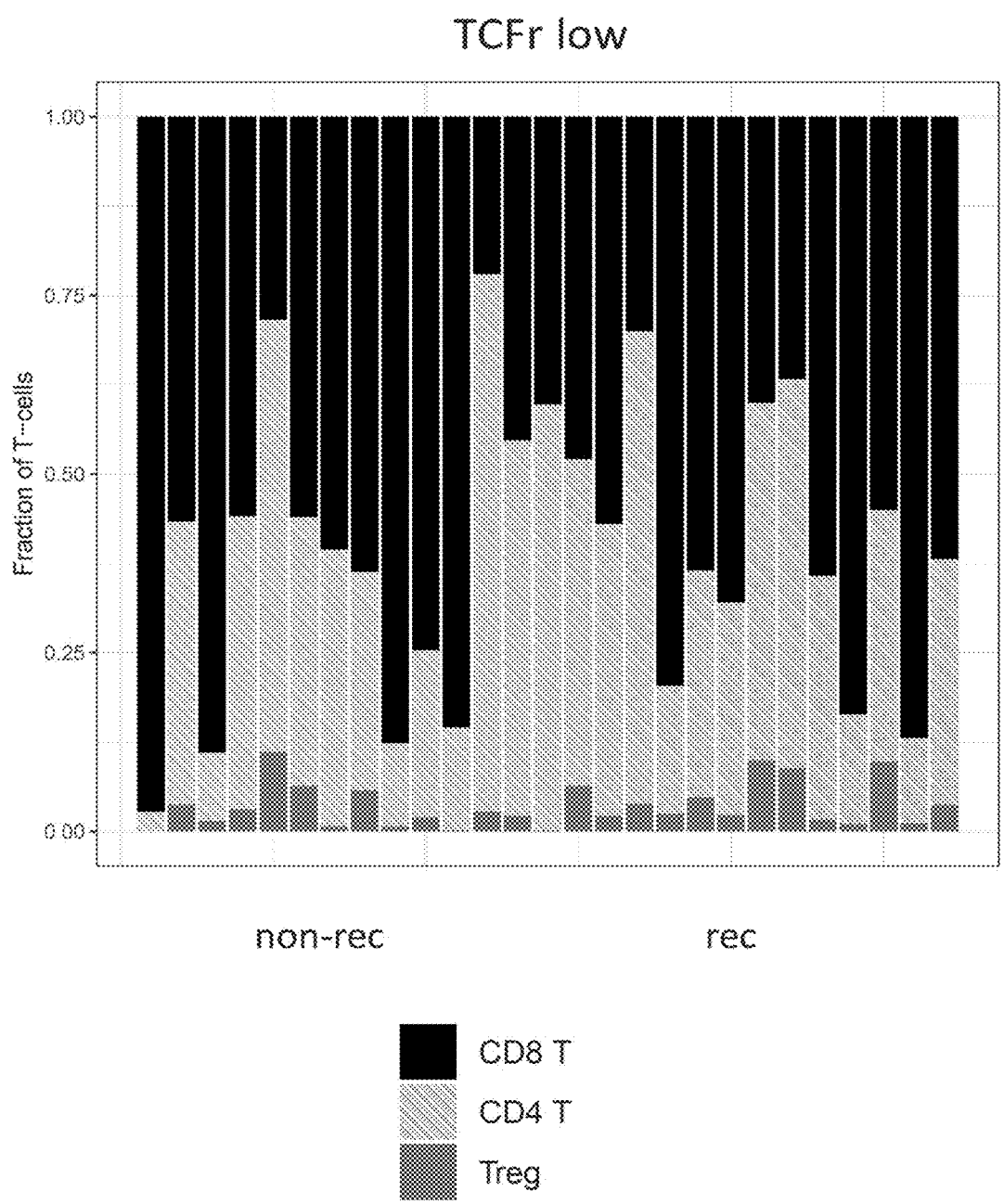
FIG. 8B, continued

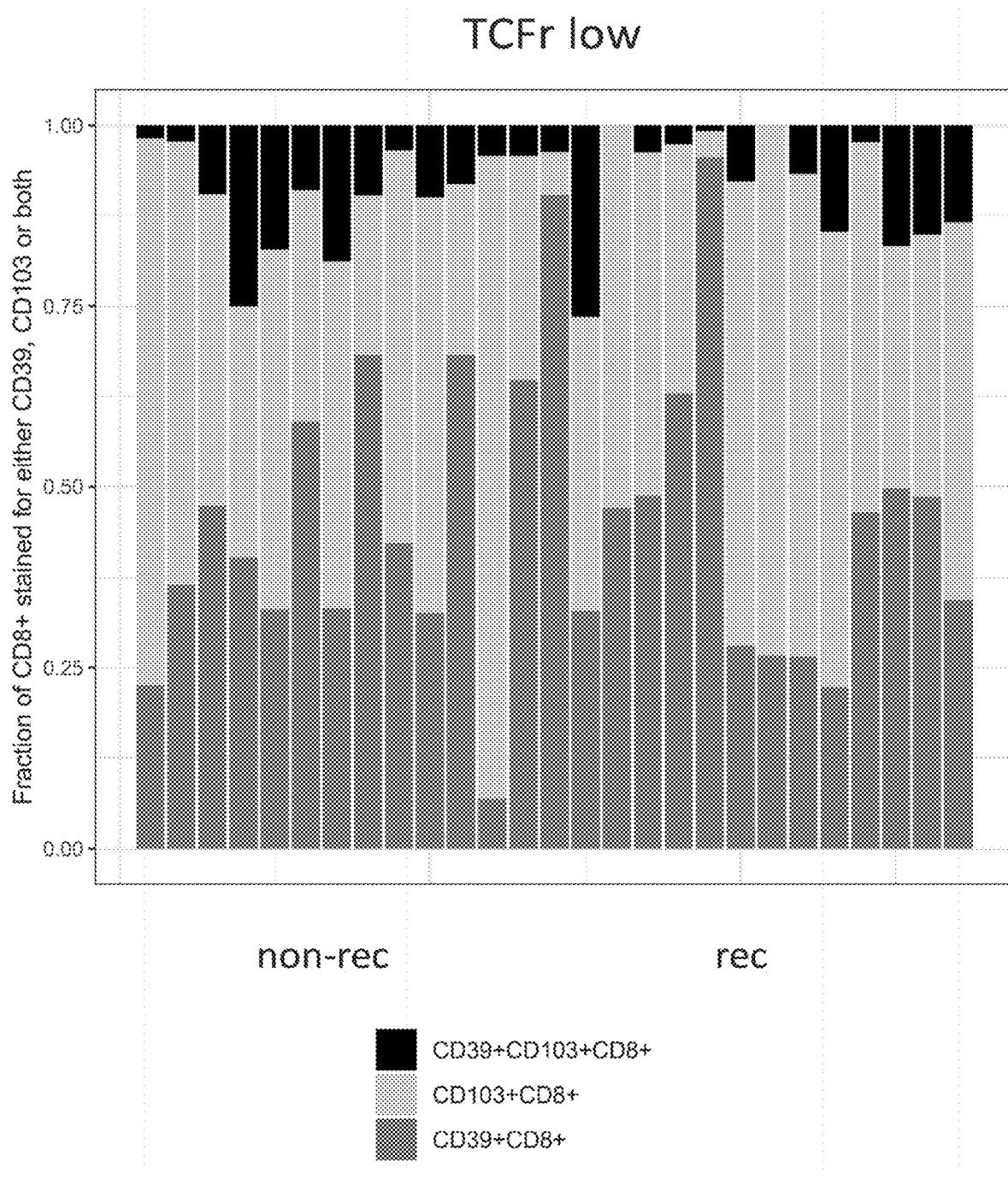
FIG. 8D, continued

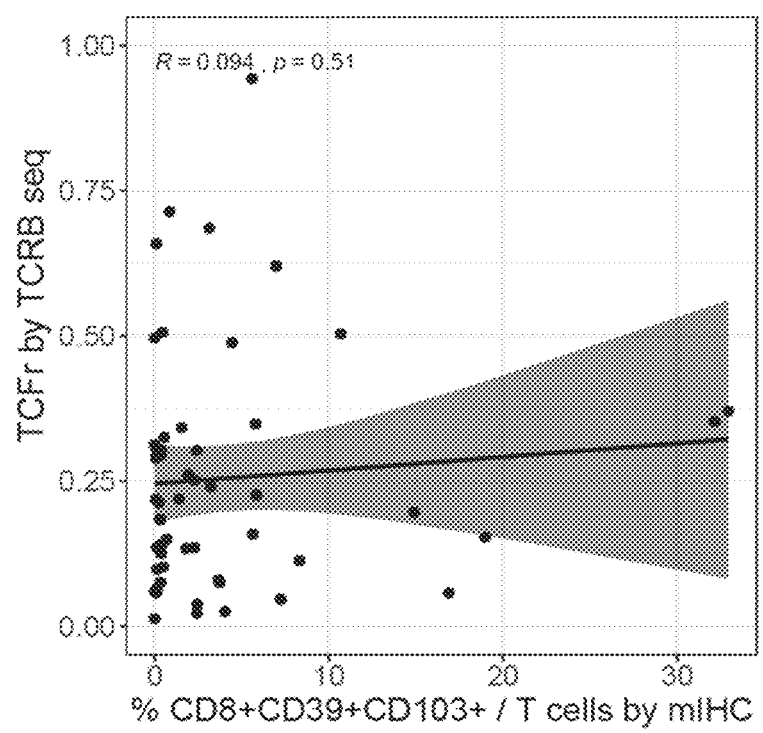
FIG. 8E, continued

| Sample_ID | Section number | % T cells/ total cells | % CD8+ T cells/ T cells | % CD4+ T cells/ T cells | % Tregs/ CD4+ T cells | % CD39+/ CD8+ T cells | % CD39+ CD103+/ CD8+ T cells |
|---|---|---|---|---|---|---|---|
| 3_63_AUS3 | 1 | 3.96 | 73.71 | 26.28 | 1.03 | 11.20 | 1.90 |
| 3_63_AUS3 | 2 | 5.54 | 74.50 | 25.49 | 6.76 | 27.26 | 13.31 |
| 3_63_AUS3 | 3 | 6.23 | 69.85 | 30.14 | 11.01 | 26.63 | 12.97 |
| P08_AUS2 | 1 | 5.45 | 34.20 | 65.79 | 0.01 | 23.89 | 9.17 |
| P08_AUS2 | 2 | 17.79 | 87.85 | 12.14 | 7.73 | 40.19 | 23.46 |
| P08_AUS2 | 3 | 13.98 | 92.72 | 7.27 | 10.30 | 26.71 | 13.13 |

FIG. 11C

METHODS FOR IDENTIFYING PROGRESSION OF A PRIMARY MELANOMA

CLAIM OF PRIORITY

This application is a continuation of U.S. application Ser. No. 16/838,926, filed on Apr. 2, 2020, which claims the benefit of U.S. Provisional Application Ser. No. 62/828,064, filed on Apr. 2, 2019. The entire contents of the foregoing are incorporated herein by reference.

FEDERALLY SPONSORED RESEARCH OR DEVELOPMENT

This invention was made with Government support under Grant Nos. CA203721 and AI127654 awarded by the National Institutes of Health. The Government has certain rights in the invention.

TECHNICAL FIELD

Described herein are methods of using T cell frequency (TCFR), e.g., as determined by high throughput DNA sequencing of the TCRB gene, as a predictor of disease progression and survival in patients with primary melanoma, and to select and treat subjects.

BACKGROUND

While recent advances in immunotherapy and targeted drug therapy for Stage IV melanoma have improved the prognosis for this disease, the management of primary melanoma has remained unchanged.[1,2] The prognosis of primary melanomas is based upon histopathological factors (thickness, ulceration) and assessment of regional nodal disease, variables that have not changed for decades.[3] Tumor thickness is used to assign a T stage (T1: ≤1.0 mm, T2: >1.0-2.0 mm, T3: >2.0-4.0 mm, T4>4.0 mm). Primary melanomas >T1 can often be cured by resection, but 13.4% of T2, 28.1% of T3, and 38.1% of T4 melanomas will recur metastatically within 5 years.[4] The ability to identify primary melanoma patients at risk for disease progression is an unmet need. Such knowledge would, for example, enable earlier use of adjuvant treatment regimens with immune checkpoint inhibitors, vaccination, or targeted drug therapies to prevent disease recurrence and improve outcomes.

SUMMARY

This invention is based on the surprising discovery that T cell frequency (TCFR), e.g., as determined by high throughput DNA sequencing of the TCRB gene, is a strong predictor of disease progression and survival in patients with primary melanoma, and can be used to select and treat subjects and stratify patients for different treatment modalities.

Described herein are methods to measure T-cell fraction (TCFr) (e.g., by high-throughput TCRB sequencing) among patients undergoing or previously having undergone treatment for melanoma, thereby greatly improving prediction of melanoma recurrence and guiding therapeutic treatment among patients identified as being at risk for melanoma progression.

In general, a T-cell fraction of less than 20% in a primary melanoma biopsy sample obtained from a human subject diagnosed with melanoma identifies a patient as a candidate for melanoma recurrence in need of treatment.

Methods of the invention can also be used to select or continue a treatment correlated with a good clinical response in a human subject having melanoma. Once a patient is predicted to be in need of treatment, a treatment correlated with a good clinical response can be selected and administered. The treatment can comprise, for example, established and/or experimental therapies for metastatic melanoma; therapeutic antibodies directed against immune checkpoint inhibitors, such as PD-1, PD-L1, CTLA-4, Lag-1, TIGIT, Tim 3, alone or in combinations (e.g., pembrolizumab, nivolumab or ipilimumab); targeted drug therapies for patients with BRAF mutations, including BRAF inhibitors (e.g., vemurafantib) and MEK inhibitors (e.g., trametinib); interferon α alone or in combination with the above. Other therapies could include experimental vaccines and other current experimental approaches to metastatic melanoma.

Thus provided herein are methods for treating a subject who has primary melanoma. The methods include obtaining a biopsy sample from the primary melanoma; determining the T cell frequency (TCFr) of said sample; and treating said subject with an aggressive treatment when the TCFr is greater than a reference level.

Also provided are methods for selecting a subject with primary melanoma for aggressive treatment. The methods include obtaining a biopsy sample from the primary melanoma; determining the T cell frequency (TCFr) of said sample; and selecting a subject who has a TCFr below a reference level for aggressive treatment.

Additionally provided are methods for predicting whether a subject with primary melanoma is likely to progress to metastatic melanoma. The methods include obtaining a biopsy sample from the primary melanoma; determining the T cell frequency (TCFr) of said sample; and identifying a subject who has a TCFr below a reference level as likely to progress to metastatic melanoma.

In some embodiments, the primary melanoma is cutaneous melanoma.

In some embodiments, the primary melanoma is 1-4 mm thick.

In some embodiments, the primary melanoma is stage I to IIC.

In some embodiments, determining the T cell frequency (TCFr) of said skin sample comprises analyzing T-cell receptor beta (TCR β) gene sequences in substantially every T cell in the sample, quantitating total nucleated cells and calculating the proportion of T cells in the sample relative to its total number of nucleated cells. In some embodiments, said analyzing is performed by high-throughput DNA sequencing.

In some embodiments, the aggressive treatment is targeted treatment, immunotherapy, chemotherapy, and/or radiation, or a combination thereof.

In some embodiments, the chemotherapy comprises administration of one or more nitrosoureas; alkylating agents; microtubule targeting agents; or platinum-containing agents.

In some embodiments, the targeted treatment comprises a BRAF inhibitor and/or a MEK inhibitor.

In some embodiments, the immunotherapy comprises administration of a checkpoint inhibitor.

In some embodiments, the immunotherapy comprises administration of a vaccines targeting melanoma cells, peptide-based vaccine, viral vector-based vaccine, or dendritic cell vaccine.

In some embodiments, wherein the reference level is 20%.

In some embodiments, the methods also include determining one or more of Breslow thickness; ulceration status; levels of mitoses/mm$^2$; and nodal disease in the sample, and determining prognosis or selecting therapy based on TCFr and Breslow thickness; ulceration status; levels of mitoses/mm$^2$; and/or nodal disease in the sample.

Provided herein are methods of selecting a treatment correlated with a good clinical response in a human subject diagnosed with melanoma, said methods comprising the steps of: determining whether there is a T-cell fraction of less than 20% in a primary melanoma biopsy sample obtained from the human subject, and selecting a treatment comprising an immune checkpoint inhibitor, vaccination, or a targeted drug therapy to administer to the human subject, thereby selecting a treatment correlated with a good clinical response in the human subject diagnosed with melanoma.

In some embodiments, methods of the invention further comprise determining that Breslow's thickness in a primary melanoma of the subject is between about 1 mm to about 4 mm thick.

In some embodiments, the good clinical response is progression free survival for a duration of at least two years.

In some embodiments, the T-cell fraction is determined by high throughput sequencing comprising amplifying the T Cell Receptor Beta gene, quantitating the total nucleated cells and calculating the proportion of T cells in a sample relative to its total number of nucleated cells.

In some embodiments, the immune checkpoint inhibitor is pembrolizumab, nivolumab or ipilimumab.

In some embodiments, the targeted drug therapy is vemurafenib or trametinib.

Also provided herein are methods of identifying a human subject diagnosed with melanoma as a candidate for melanoma recurrence, said methods comprising the steps of: determining whether there is a T-cell fraction of less than 20% in a sample obtained from the human subject, wherein said level or levels are compared to a reference level or levels; and identifying the human subject as a candidate for melanoma recurrence.

In some embodiments, the methods further comprise determining that Breslow's thickness in a primary melanoma of the subject is between about 2 mm to about 4 mm thick.

In some embodiments, the T-cell fraction is determined by high throughput sequencing comprising amplifying the T Cell Receptor Beta gene, quantitating the total nucleated cells and calculating the proportion of T cells in a sample relative to its total number of nucleated cells.

In some embodiments, the reference level or levels are determined from a sample previously obtained from the human subject.

Definitions

Unless otherwise defined, all technical and scientific terms used herein have the same meaning as commonly understood by one of ordinary skill in the art to which this invention belongs. In case of conflict, the present application, including definitions will control.

A "subject" is a vertebrate, including any member of the class mammalia, including humans, domestic and farm animals, and zoo, sports or pet animals, such as mouse, rabbit, pig, sheep, goat, cattle and higher primates.

A "T-cell fraction" or "TCFr" is a proportion of nucleated cells that are T cells.

As used herein, the terms "treat," "treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

As used herein, "Breslow thickness" refers to a measure, in millimeters, of the distance between the upper layer of the epidermis and the deepest point of melanoma tumor penetration. The thinner the melanoma, the better the chance of long term survival as well as a good clinical response to therapy.

As used herein, the term "progression-free survival" refers to the time from the first administration or application of a melanoma therapy to the first documented evidence of progressive disease, if any. The term "overall survival" is defined as the time from the first administration or application of a melanoma therapy to the date of death, regardless of cause.

Unless specifically stated or clear from context, as used herein, the term "about" is understood as within a range of normal tolerance in the art, for example within 2 standard deviations of the mean. "About" is understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 (as well as fractions thereof unless the context clearly dictates otherwise).

As used herein, the term "reference level" refers to the level of T-cell fraction in a known sample against which another test sample is compared. A reference level can be obtained, for example, from a known sample from a different individual (e.g., not the individual being tested), either having or not having melanoma. The reference level may be determined before and/or after treatment and optionally, from samples obtained from the same subject before and/or treatment.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Other definitions appear in context throughout this disclosure.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 11A-C. Composition of T cell infiltrate. (a) Boxplot illustrating the higher median TCFr measured by TCRB sequencing in comparison to multiplex immunohistochemistry (mIHC), medianHTS=0.21 vs medianmIHC=0.05. Two-sided Wilcoxon Rank Sum Test; TCRseq, n=199 primary melanoma patients; mIHC, n=57. Box plots: the bold line indicates the median; box illustrates lower and upper quartiles; whiskers show the lowest and highest data points still within 1.5× of interquartile range from lower or upper quartile, respectively; dots are data points. (b) Overall, the TCFr determined by TCRB sequencing correlates with the fraction of CD3+/DAPI (all) cells by mIHC. Line=regression line, grey shading=95% confidence interval, Spearman's correlation test; n=57 primary melanoma samples. (c) The percentage of CD3+ cells as well as of CD8+, CD4+, Tregs and tumor antigen specific CD8+ T cells (CD8+CD39+ and CD8+CD39+CD103+) varies greatly if multiple (sequential) sections of one tumor were analyzed.

DETAILED DESCRIPTION

Figure 1:
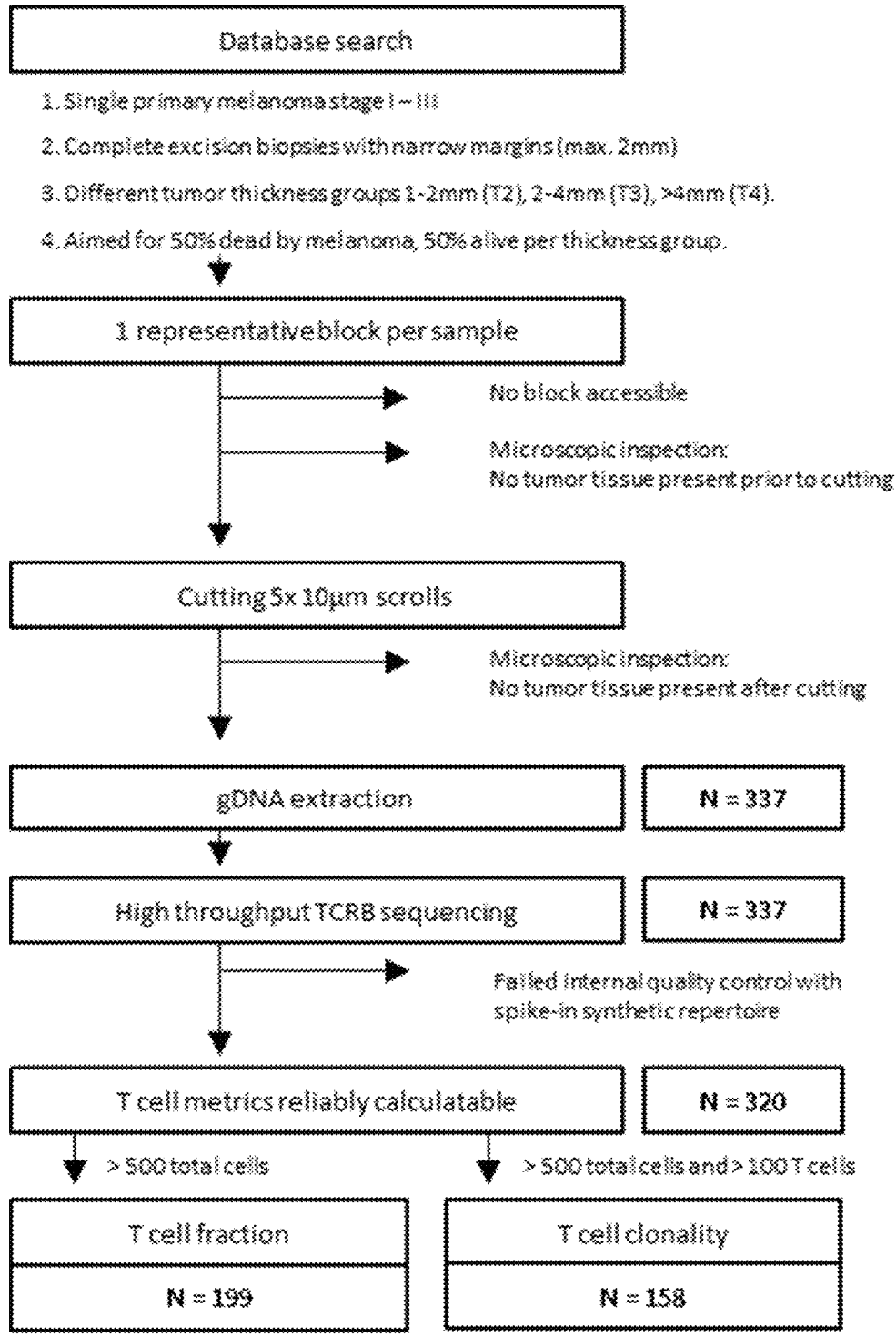
FIG. 1. Study Design. This flow diagram illustrates the selection and processing of primary melanoma cases included in this study.

Melanomas have a high mutation burden[5,6] and generate an adaptive immune response via their mutation-derived neoantigens.[7] Several studies have demonstrated the association of lymphocyte infiltration of melanomas with longer progression-free and overall survival[8,9,10-15] and other groups have studied "tumor infiltrating lymphocytes," reporting an inverse correlation between TIL grade and presence of sentinel lymph node metastases.[10,16-20] However, some reports have found a lack of association between TILs and survival rates.[16,18,19,21-23] Routine histopathological evaluation of TILs cannot distinguish between T cells, B cells, and NK cells. Currently, neither current AJCC staging nor NCCN guidelines include TILs in their prognostic algorithm.

Recently, targeted drug and immunotherapies have improved survival in metastatic melanoma; however, these therapies are only effective for subsets of patients.[24,25] Several studies have been conducted to identify factors that predict response to immunotherapy[26] and several have used T-cell receptor (TCR) profiling of blood T cells[27-29] or T cells in metastases.[30-33] The "clonality" of the T-cell repertoire in metastatic lesions, as measured by high-throughput sequencing of the TCR beta-chain (TCRB), has been useful as a biomarker of response to anti PD-1 therapy.[30] In the present study, we sought to determine whether features of the T-cell repertoire predicted recurrence in patients with resected primary melanomas.

Using high-throughput TCRB sequencing, we calculated T-cell fraction (TCFr, proportion of nucleated cells that are T cells) and T-cell clonality in patients with surgically resected primary melanomas (T2-T4). Our goal was to identify a clinically translatable TCFr value that predicted recurrent disease in comparably-sized training and test patient cohorts.

Using a collection of surgically resected primary melanomas >1 mm thickness, the present study established that T-cell fraction (TCFr), as measured by high-throughput TCRB sequencing, improved the accuracy of prediction of melanoma recurrence. We found that a 20% TCFr was the best threshold to identify patients at risk for disease progression, with patients below 20% TCFr 2.5 times more likely to progress than patients >20% TCFr. As a prognostic marker, TCFr offers advantages over existing tools. TCFr is completely independent of tumor thickness (and any other clinical or histological variable) and does not depend upon visual inspection. For more accurate T staging, adding TCFr to tumor thickness was superior to adding any other predictive histopathological factor. Furthermore, TCFr appeared to be the second most powerful factor after tumor thickness in its relative influence on predicting recurrence.

T cells have been studied most frequently in the context of metastatic melanoma, with only a limited number of studies investigating primary melanomas. 26,27,29,31,32 Primary melanomas are typically diagnosed by dermatologists or general practitioners, and patients with completely resected disease are often not followed in cancer centers. van Houdt et al. characterized the infiltration of different lymphocyte subpopulations in the diagnostic biopsy of Stage II melanoma patients, finding a favorable clinical outcome was associated with the presence of Granzyme B+ T cells.[13] Vasaturo et al. studied patients who underwent dendritic cell vaccination therapy and showed that a high density of T cells within the primary tumor was a strong predictor of response.[38] A recent transcriptomic study of primary melanomas identified six distinct subgroups based on their expression of immune-related, keratin, and □-catenin pathway genes.[39] Patients with a low immune but high β-catenin score (CIC4) had the poorest overall survival. The five other subgroups had similar survival rates.

In the present study, TCFr high and TCFr low samples had comparable numbers of CD4+, CD8+ and putative antigen specific CD8+CD39+ and CD8+CD39+CD103+ T cells. There was no predominance of CD8+ or CD4+ T cells. Interestingly, TCFr high samples that did not recur had the lowest number of infiltrating T regulatory cells. None of the T cell subsets was predictive of 5-year progression-free survival, although mIHC was only performed on ~25% of the TCRB HTS cohort. "Tumor specific" CD8+ T cells were found in low percentages, which is consistent with previous findings that reported most tumor infiltrating T cells to be bystanders.[40,41] Infiltration of T cells into a tumor is governed less by antigen and more by trafficking/adhesion molecules and chemokines in an antigen-independent fashion. Once in the tumor, T cells that are specific for tumor antigens have the potential to become activated. However, higher clonality was not associated with improved PFS, suggesting that there was limited expansion of tumor specific T cells. It is possible that the TCFr is governed principally by the ability of the tumor to recruit or exclude circulating T cells.

The prognostic accuracy of molecular TCFr by HTS was superior to TIL assessment by histopathology. While TCFr correlated with both conventional and MIA TIL grading approaches, clinically important discrepancies occurred at higher grades (brisk and MIA 2/3). Similarly, CD3 counts by IHC correlated with TCFr, but significant variability (>3-fold) was seen with CD3 counts on sequential sections of the same tumor. Histopathological TIL infiltration is assessed microscopically on a single slide by visual inspection using an interpretative scoring system, and the classification of lymphocytes as either "infiltrating" or "not infiltrating" the tumor nest is subjective.[42] TCFr, by contrast, utilizes 5×10 μm FFPE scrolls, capturing a larger portion of the primary tumor and its microenvironment. Finally, histopathological assessments only count intratumoral TILs in direct contact with melanoma cells, while TCFr measures T cells regardless of their location in the tumor specimen. For these reasons, TCFr has clear advantages over TIL count by H&E or CD3 count by IHC. Interestingly, a recent study described an increased peritumoral density of T-cell activation markers OX40 (CD134) and CD25 (interleukin 2Rα) on primary melanomas to be beneficial for survival, while intratumoral levels were not predictive.[43] In support of this observation, data derived from a study evaluating peritumoral versus intratumoral TILs of primary melanomas showed that high peritumoral lymphocyte scores were inversely associated with tumor thickness, Clark level, and mitotic rate, and tended to have a longer PFS.[44]

Huang and colleagues gave a single dose of pembrolizumab to 27 patients with Stage III/IV melanoma patients 3 weeks prior to definitive surgical resection (additional adjuvant pembrolizumab was subsequently given). In 8 patients, significant to complete immune mediated tumor lysis was seen in the primary melanoma at the time of resection (3 weeks), and an increase of intratumoral CD8+ T cells expressing exhaustion markers (PD-1, Tim-3, CTLA-4, LAG3, TIGIT, and CD39) was observed.[45] The authors interpreted the response as having been mediated by T cells in the primary tumor, despite all but one of the patients having "non-brisk" infiltrates initially. Our data are also consistent with an adaptive immune response to melanoma being present in primary tumors. The fact that PFS is greatly improved in our patients with >20% TCFr in their primary tumors suggests that this antitumor response is often successful. It would be interesting to compare the response to anti-PD-1 blockade in our patients with Stage II and III disease with high and low TCFr.

In terms of practical clinical use, a major advantage of analyzing the TCFr in primary tumors is that it can identify patients at high risk of metastatic disease for potential adjuvant therapy.[38] The TCRB HTS assay works reliably on FFPE samples<1-2 years old, is already commercially available for research use, and could be easily translated for clinical testing, subject to regulatory requirements. The relatively favorable prognosis of patients with >20% TCFr might be further improved by the use of immune checkpoint inhibitor therapy. Patients with low TCFr and higher risk for recurrence may have some benefit,[45] but will likely require additional adjuvant therapeutic interventions (e.g. vaccination) to prevent disease progression. In this fashion, measuring the TCFr of primary melanomas could help move the field towards individualized tumor treatment by matching patients with their optimal immunotherapeutic approach.

Melanoma

The present disclosure provides methods for diagnosing and treating subjects with primary melanoma, a tumor produced by the malignant transformation of melanocytes, including superficial spreading melanoma, nodular melanoma, lentigo maligna melanoma, and acral lentiginous melanoma. Melanomas are typically on skin (cutaneous melanoma) but can also arise in mucosal tissues (Mucosal melanoma), brain (cerebral melanoma), and in the eyes (ocular melanoma). Mucosal melanoma can appear in respiratory tract; nasal cavity; paranasal sinuses; oral cavity; gastrointestinal tract; transitional zone of anal canal (the line where the normal skin meets the mucous membrane); genitourinary tract; vulva; and vagina. See, e.g., Tang et al., Medicine (Baltimore). 2017 January; 96(4): e5805; Yde et al., Curr Oncol Rep. 2018 Mar. 23; 20(3):28; Rastrelli et al., In Vivo. 2014 November-December; 28(6):1005-11; Pavri et al., Plast Reconstr Surg. 2016 August; 138(2):330e-40e; Shain and Bastian, Nat Rev Cancer. 2016 June; 16(6):345-58.

Classification or staging of melanomas can be done using, e.g., Breslow classification; TNM (tumor, node, metastasis) system for clinical staging as designated by the American Joint Committee on Cancer (AJCC) staging system; American Joint Committee on Cancer. *Malignant melanoma of the skin*. IN: American Joint Committee on Cancer: AJCC Cancer Staging Manual. 5th ed. Philadelphia, Pa: Lippincott-Raven; 1997. 163-70); or Clark levels (e.g., for thin (t1) melanomas).

TABLE A

Exemplary Melanoma Staging Scheme

| | |
|---|---|
| Stage 0 (pTis, N0, M0) | The melanoma is in situ, meaning that it involves the epidermis but has not spread to the dermis (lower layer). |
| Stage IA (pT1a, N0, M0) | The melanoma is less than 1 mm in thickness and Clark level II or III. It is not ulcerated, appears to be localized in the skin, and has not been found in lymph nodes or distant organs. |
| Stage IB (pT1b or pT2a, N0, M0) | The melanoma is less than 1 mm in thickness and is ulcerated or Clark level IV or V, or it is 1.01-2 mm and is not ulcerated. It appears to be localized in the skin and has not been found in lymph nodes or distant organs. |
| Stage IIA (pT2b or pT3a, N0, M0) | The melanoma is 1.01-2 mm in thickness and is ulcerated, or it is 2.01-4 mm and is not ulcerated. It appears to be localized in the skin and has not been found in lymph nodes or distant organs. |
| Stage IIB (pT3b or pT4a, N0, M0) | The melanoma is 2.01-4 mm in thickness and is ulcerated, or it is thicker than 4 mm and is not ulcerated. It appears to be localized in the skin and has not been found in lymph nodes or distant organs. |
| Stage IIC (pT4b, N0, M0) | The melanoma is thicker than 4 mm and is ulcerated. It appears to be localized in the skin and has not been found in lymph nodes or distant organs. |
| Stage III (any pT, N1-3, M0) | The melanoma has spread to lymph nodes near the affected skin area. No distant spread is present. The thickness of the melanoma is not a factor, although it is usually thick in people with stage III melanoma. |
| Stage IV (any pT, any N, any M1) | The melanoma has spread beyond the original area of skin and nearby lymph nodes to other organs, such as the lungs, liver, or brain, or to distant areas of the skin or lymph nodes. Neither the lymph node status nor thickness is considered, but in general, the melanoma is thick and has spread to lymph nodes. |

TABLE B

Breslow's depth

| Stage | Depth |
|---|---|
| Stage I | 0.75 mm or less |
| Stage II | 0.76 mm-1.50 mm |
| Stage III | 1.51 mm-2.25 mm |
| Stage IV | 2.26 mm-3.0 mm |
| Stage V | 3.0 mm or more |

In some embodiments, the present methods can be used on melanomas that have not metastasized, preferably stage 0 up to stage IIC (see Table A), with less than 4 mm thickness.

The present methods can be used, e.g., in addition to staging or prognostic methods based on staging or thickness.

The present disclosure provides methods for identifying subjects having a high likelihood of developing metastatic cancer, and optionally treating subjects identified using a method described herein. In some embodiments, this disclosure provides methods for diagnosing and treating subjects with primary melanoma, e.g., melanomas of up to 4 mm thickness, e.g., 1-4 mm or 2-4 mm.

Methods of Prognosis

Risk stratification is one of the goals of precision oncology, and there is great interest in biomarkers that predict aggressive disease in malignancies in which a majority of patients have indolent disease, while a smaller subset develop aggressive disease. Identifying patients at risk for disease progression is particularly important in melanoma, a disease in which two patients with similar physical exams and histopathological morphology can have markedly different outcomes. High-throughput sequencing of the TCRB gene provides a precise and quantitative measurement of the T cell fraction in melanoma lesions.

Thus, included herein are methods for predicting whether a subject with a primary melanoma, e.g., a presently apparently non-malignant melanoma, will develop aggressive disease. The methods include obtaining a sample from a subject, and evaluating the T Cell Frequency (TCFr) in the sample.

T-cell fraction can be determined, for example, by high throughput sequencing comprising amplifying the T Cell Receptor Beta gene, quantitating the total nucleated cells and calculating the proportion of T cells in a sample relative to its total number of nucleated cells.

The quantification of tumor infiltrating lymphocytes (TILs) reliably measures the patient's "immunocompetence," specifically against that tumor, predicting the response to immune-modulating cancer therapies. Assessment of TIL quantity and clonality can be achieved by next generation sequencing of T-Cell receptor (TCR) DNA (genomic) sequences (e.g. ImmunoSEQ™ Assay by Adaptive Biotechnologies, Seattle, WA) which uses optimized PCR primers and a synthetic immune repertoire with computational algorithms to sequence T cell receptor (TCR) genomic sequences, see e.g., U.S. Pat. Nos. 9,150,905 and 9,371,558). The TCR receptor family comprises 4 receptor chains: the TCR alpha, beta, gamma and delta chains. The loci for the alpha, beta and gamma chains encoding these TCRs are located respectively at the chromosomal positions 14q11-12, 7q32-35, 7p15. The delta chain gene locus is co-situated within the alpha gene locus at 14q1 1-12. Next-generation sequencing of the TCR loci involves preliminary construction of a sequencing library which itself depends on the ability to PCR amplify the TCR gene sequence. The size of the PCR amplicon required for construction of informative sequencing libraries ranges between about 50 and about 200 base pairs.

In some embodiments, the methods rely on detection and quantification of sequences of TCRB in substantially every T cell in the sample to determine numbers of T cell. In some embodiments, the sequence of the TCRB or CD3 region is determined. In some embodiments, the methods include calculating T-cell fraction as the proportion of T cells in a sample relative to its total number of nucleated cells.

As used herein the term "sample", when referring to the material to be tested for the presence of a biological marker using the method of the invention, preferably includes a sample comprising lesional (affected) skin, e.g., obtained by a biopsy. Various methods are well known within the art for the identification and/or isolation and/or purification of a biological marker from a sample. An "isolated" or "purified" biological marker is substantially free of cellular material or other contaminants from the cell or tissue source from which the biological marker is derived i.e. partially or completely altered or removed from the natural state through human intervention. For example, nucleic acids contained in the sample are first isolated according to standard methods, for example using lytic enzymes, chemical solutions, or isolated by nucleic acid-binding resins following the manufacturer's instructions.

A level of a TRB (TCRB) nucleic acid sequence, e.g., a CDR3 sequence, can be evaluated using methods known in the art, e.g., using Immunosequencing, polymerase chain reaction (PCR), reverse transcriptase polymerase chain reaction (RT-PCR), quantitative or semi-quantitative real-time RT-PCR, digital PCR i.e. BEAMing ((Beads, Emulsion, Amplification, Magnetics) Diehl (2006) Nat Methods 3:551-559); RNAse protection assay; Northern blot; various types of nucleic acid sequencing (Sanger, pyrosequencing, Next-Generation Sequencing); fluorescent in-situ hybridization (FISH); or gene array/chips) (Lehninger Biochemistry (Worth Publishers, Inc., current addition; Sambrook, et al, Molecular Cloning: A Laboratory Manual (3. Sup.rd Edition, 2001); Bernard (2002) Clin Chem 48(8): 1178-1185; Miranda (2010) Kidney International 78:191-199; Bianchi (2011) EMBO Mol Med 3:495-503; Taylor (2013) Front. Genet. 4:142; Yang (2014) PLOS One 9(11):e110641); Nordstrom (2000) Biotechnol. Appl. Biochem. 31(2):107-112; Ahmadian (2000) Anal Biochem 280:103-110. In some embodiments, high throughput methods, e.g., protein or gene chips as are known in the art (see, e.g., Ch. 12, Genomics, in Griffiths et al., Eds. *Modern genetic Analysis*, 1999, W. H. Freeman and Company; Ekins and Chu, Trends in Biotechnology, 1999, 17:217-218; MacBeath and Schreiber, Science 2000, 289(5485):1760-1763; Simpson, *Proteins and Proteomics: A Laboratory Manual*, Cold Spring Harbor Laboratory Press; 2002; Hardiman, *Microarrays Methods and Applications: Nuts & Bolts*, DNA Press, 2003), can be used to detect the TCFr. Measurement of the level of a biomarker can be direct or indirect. For example, the abundance levels of TCRB can be directly quantitated and used to calculate TCFr. Alternatively, the amount of a biomarker can be determined indirectly by measuring abundance levels of cDNA, amplified RNAs or DNAs, or by measuring quantities or activities of RNAs, or other molecules that are indicative of the expression level of the biomarker. In some embodiments a technique suitable for the detection of alterations in the structure or sequence of nucleic acids, such as the presence of deletions, amplifications, or substitutions, can be used for the detection of biomarkers of this invention.

RT-PCR can be used to determine the expression profiles of biomarkers (U.S. Patent No. 2005/0048542A1). The first step in expression profiling by RT-PCR is the reverse transcription of the RNA template into cDNA, followed by its exponential amplification in a PCR reaction (Ausubel et al (1997) Current Protocols of Molecular Biology, John Wiley and Sons). To minimize errors and the effects of sample-to-sample variation, RT-PCR is usually performed using an internal standard, which is expressed at constant level among tissues, and is unaffected by the experimental treatment.

Gene arrays are prepared by selecting probes which comprise a polynucleotide sequence, and then immobilizing such probes to a solid support or surface. For example, the probes may comprise DNA sequences, RNA sequences, co-polymer sequences of DNA and RNA, DNA and/or RNA analogues, or combinations thereof. The probe sequences can be synthesized either enzymatically in vivo, enzymatically in vitro (e.g. by PCR), or non-enzymatically in vitro.

High throughput sequencing can be used to determine the abundance of sequence in a sample (3, 31, 32, 33, and US 2015-0141261 A1). For example, the abundance of a particular CDR3 sequence of a TCRB gene from a malignant T cell in a sample can be measured, e.g., using high throughput sequencing, Immunosequencing, or other methods. See, e.g., Kou et al., Clin Diagn Lab Immunol. 2000 November; 7(6): 953-959; Kirsch et al., Sci. Transl. Med. 7, 308ra158 (2015); Robins et al., Blood 114, 4099-4107 (2009); Keane et al., Clin Cancer Res. 2017 Apr. 1; 23(7):1820-1828. A reference sequence of TCRB is at GenBank Ref. no. NG_001333.2. In some embodiments, in place of or in addition to TCRB, TCRG is used; a reference sequence of TCRG is at GenBank Ref. no. NG_001336.2.

In some embodiments, the TCFr, and optionally the lesion thickness, is used to predict risk of metastasis of a melanoma. In some embodiments, once it has been determined by a method described herein that a person has a risk of developing metastatic melanoma, then a treatment, e.g., as known in the art or as described herein, can be administered. In some embodiments, a subject who has an increased risk is a subject who has a level of TCFr≤20%, compared to a subject in a reference cohort who has a TCFr>20%, and therefore does not have a significant risk of developing aggressive disease, e.g., within one, two, five, or ten years.

Suitable reference values can be determined using methods known in the art, e.g., using standard clinical trial methodology and statistical analysis. The reference values can have any relevant form. In some cases, the reference comprises a predetermined value for a meaningful level of TCFr, e.g., a control reference level that represents a normal level of TCFr, e.g., a level in a subject who is not at risk (or who has a normal risk) of developing metastatic disease described herein, and/or a disease reference that represents a level of the TCFr associated with increased risk of developing metastatic melanoma. g., a level in a subject who has or who later develops metastatic melanoma (e.g., stage III or IV in Table A).

The predetermined level can be a single cut-off (threshold) value, such as a median or mean, or a level that defines the boundaries of an upper or lower quartile, tertile, or other segment of a clinical trial population that is determined to be statistically different from the other segments. It can be a range of cut-off (or threshold) values, such as a confidence interval. It can be established based upon comparative groups, such as where association with risk of developing disease or presence of disease in one defined group is a fold higher, or lower, (e.g., approximately 2-fold, 4-fold, 8-fold, 16-fold or more) than the risk or presence of disease in another defined group. It can be a range, for example, where a population of subjects (e.g., control subjects) is divided equally (or unequally) into groups, such as a low-risk group, a medium-risk group and a high-risk group, or into quartiles, the lowest quartile being subjects with the lowest risk and the highest quartile being subjects with the highest risk, or into n-quantiles (i.e., n regularly spaced intervals) the lowest of the n-quantiles being subjects with the lowest risk and the highest of the n-quantiles being subjects with the highest risk.

In some embodiments, the predetermined level is a level or occurrence in the same subject, e.g., at a different time point, e.g., an earlier time point.

In some embodiments, the predetermined reference level is 20% TCFr. Subjects associated with predetermined values are typically referred to as reference subjects. For example, in some embodiments, a control reference subject has primary melanoma, but does not have an increased risk of developing (or does not later develop) metastatic melanoma.

A disease reference subject is one who has an increased risk of developing (or who later develops) metastatic melanoma. An increased risk is defined as a risk above the risk of subjects in the general population.

Thus, in some cases the level of TCFr in a subject being less than or equal to a reference level of TCFr is indicative of a clinical status (e.g., indicative of a disorder as described herein, e.g., risk of developing metastatic melanoma. In other cases the level of TCFr in a subject being greater than or equal to the reference level of TCFr is indicative of the absence of risk or normal risk of metastatic melanoma. In some embodiments, the amount by which the level in the subject is the less than the reference level is sufficient to distinguish a subject from a control subject, and optionally is a statistically significantly less than the level in a control subject. In cases where the level of TCFr in a subject being equal to the reference level of TCFr, the "being equal" refers to being approximately equal (e.g., not statistically different).

The predetermined value can depend upon the particular population of subjects (e.g., human subjects) selected. Accordingly, the predetermined values selected may take into account the category (e.g., sex, age, health, risk, presence of other diseases) in which a subject (e.g., human subject) falls. Appropriate ranges and categories can be selected with no more than routine experimentation by those of ordinary skill in the art.

In some embodiments, a TCFr below about 15%, 16%, 17%, 18%, 19%, 20%, 21%, 22%, 23%, 24%, 25%, 26%, 27%, 28%, 29%, or 30% is used to identify a subject as at risk of metastatic melanoma. In some embodiments, a TCFr below or equal to about 15%, 16%, 17%, 18%, 19%, 20%, 21%, 22%, 23%, 24%, 25%, 26%, 27%, 28%, 29%, or 30% is used to identify as subject as at risk of developing metastatic melanoma. In some embodiments, a TCFr of about 15%, 16%, 17%, 18%, 19%, 20%, 21%, 22%, 23%, 24%, 25%, 26%, 27%, 28%, 29%, or 30% is used to identify as subject as at risk of developing metastatic melanoma.

In characterizing likelihood, or risk, numerous predetermined values can be established.

In some embodiments, TCFr plus one or more other parameters of disease are used, e.g., TCFr plus one or more of Breslow thickness; ulceration status; levels of mitoses/$mm^2$; nodal disease (tumor-positive regional lymph nodes at initial diagnosis). Thus, for example, a high Breslow (e.g., 2-4 mm thick) melanoma with high TCFr (20% or above) does as well or better than a lower Breslow (e.g., 1-2 mm) melanoma with low TCFr (below 20%). A melanoma with a high Breslow score (2-4 mm or thinker) and a low TCFr (below 20%) has the worst prognosis/highest likelihood of metastasis, while a melanoma with a low Breslow score (1-2 mm or less) and a high TCFr (20% or above) has the best prognosis/lowest likelihood of metastasis. The same holds true for the other parameters, providing for more nuanced understanding of prognosis.

Methods of Treatment

The methods described herein include methods for the treatment of subjects identified as at risk of developing metastatic melanoma. In some embodiments, the subject has primary melanoma. Generally, the methods include administering a treatment, e.g., a treatment for malignant melanoma, to a subject who is in need of, or who has been determined to be in need of, such treatment. In some embodiments the methods include targeted treatments, immunotherapy, chemotherapy, and/or radiation.

As used in this context, to "treat" means to ameliorate at least one symptom of the metastatic melanoma and/or reduce risk of developing metastatic melanoma. Often, metastatic melanoma results in metastasis of tumors in distal tissues, e.g., tissue under the skin; lymph nodes; lungs; liver; and brain; thus, a treatment can result in a reduction in tumor burden, or a reduction in risk of metastasis. Other symptoms that may be ameliorated include hardened lumps under the skin; swollen or painful lymph nodes; dyspnea or trouble breathing, or a persistent cough; hepatic swelling; loss of appetite; bone pain or broken bones; headaches, seizures, or limb weakness or numbness; weight loss; and/or fatigue.

In some embodiments, the TCFr is used to recommend administering a method of treatment for metastatic melanoma to a subject who does not have metastatic melanoma, but who has been identified using a method described herein as being at risk of developing metastatic melanoma. In some embodiments, the method of treatment includes radiotherapy, complete resection, targeted therapy with signal transduction inhibitors, immunotherapy, single agent chemotherapy, and/or Multiagent chemotherapy.

Radiation therapy can include electron beam radiation therapy, surface brachytherapy, UVB, PUVA, or other forms of ionizing radiation. In some embodiments, the radiation therapy is total skin therapy. In some embodiments, the radiation therapy is local skin therapy. In some embodiments, the radiation therapy is to the nodal basin.

Resection can include wide local excision of the primary tumor with 2-cm margins.

Targeted therapies can include administration of agents that target a genetic driver of a specific tumor, e.g., BRAF, NRAS, NF1 and KIT genomic deregulations, e.g., BRAF inhibitors (e.g., encorafenib, vemurafenib, or dabrafenib) alone and/or in combination with MEK inhibitors (e.g., binimetinib, cobimetinib, or trametinib). Trametinib is a MEK inhibitor indicated for melanoma with BRAF V600E or V600K mutations. Dabrafenib is a BRAF protein kinase inhibitor indicated for melanoma with BRAF V600E mutation. Thus the methods can include detecting the presence of one or more genetic mutations in the tumor as well and selecting a therapeutic regimen that includes targeted agents. For subjects with a BRAF mutation, the methods can include using targeted combination therapy with dabrafenib/trametinib or vemurafenib/cobimetinib.

Chemotherapy can include administration of one or more nitrosoureas (e.g., fotemustine, carmustine (BCNU), or lomustine (CCNU)); alkylating agents (e.g., melphalan, dacarbazine (DTIC) or temozolomide (TMZ)); or microtubule targeting agents (e.g., vinca alkaloids such as indesine/vinblastine, vincristine, or vinorelbine; or taxanes such as paclitaxel or docetaxel). In some embodiments is used. In some embodiments a platinum-containing agent (e.g., cisplatin, or carboplatin) is used.

The present methods can include administering an immunotherapy comprising a checkpoint inhibitor, e.g., an inhibitor of PD-1 signaling, e.g., an antibody that binds to PD-1, CD40, or PD-L1, or an inhibitor of Tim3 or Lag3, e.g., an antibody that binds to Tim3 or Lag3, or an antibody that binds to CTLA-4, or an antibody that binds to T-cell immunoglobulin and ITIM domains (TIGIT).

Exemplary anti-PD-1 antibodies that can be used in the methods described herein include those that bind to human PD-1; an exemplary PD-1 protein sequence is provided at NCBI Accession No. NP 005009.2. Exemplary antibodies are described in U.S. Pat. Nos. 8,008,449; 9,073,994; and US20110271358, including PF-06801591, AMP-224, BGB-A317, BI 754091, JS001, MEDI0680, PDR001, REGN2810, SHR-1210, TSR-042, pembrolizumab, nivolumab, avelumab, pidilizumab, and atezolizumab.

Exemplary anti-CD40 antibodies that can be used in the methods described herein include those that bind to human CD40; exemplary CD40 protein precursor sequences are provided at NCBI Accession No. NP_001241.1, NP_690593.1, NP_001309351.1, NP_001309350.1 and NP_001289682.1. Exemplary antibodies include those described in WO2002/088186; WO2007/124299; WO2011/123489; WO2012/149356; WO2012/111762; WO2014/070934; US20130011405; US20070148163; US20040120948; US20030165499; and U.S. Pat. No. 8,591,900, including dacetuzumab, lucatumumab, bleselumab, teneliximab, ADC-1013, CP-870,893, Chi Lob 7/4, HCD122, SGN-4, SEA-CD40, BMS-986004, and APX005M. In some embodiments, the anti-CD40 antibody is a CD40 agonist, and not a CD40 antagonist.

Exemplary CTLA-4 antibodies that can be used in the methods described herein include those that bind to human CTLA-4; exemplary CTLA-4 protein sequences are provided at NCBI Acc No. NP_005205.2. Exemplary antibodies include those described in Tarhini and Iqbal, Onco Targets Ther. 3:15-25 (2010); Storz, MAbs. 2016 January; 8(1):10-26; US2009025274; U.S. Pat. Nos. 7,605,238; 6,984,720; EP1212422; U.S. Pat. Nos. 5,811,097; 5,855,887; 6,051,227; 6,682,736; EP1141028; and U.S. Pat. No. 7,741,345; and include ipilimumab, Tremelimumab, and EPR1476.

Exemplary anti-PD-L1 antibodies that can be used in the methods described herein include those that bind to human PD-L1; exemplary PD-L1 protein sequences are provided at NCBI Accession No. NP_001254635.1, NP_001300958.1, and NP_054862.1. Exemplary antibodies are described in US20170058033; WO2016/061142A1; WO2016/007235A1; WO2014/195852A1; and WO2013/079174A1, including BMS-936559 (MDX-1105), FAZ053, KN035, Atezolizumab (Tecentriq, MPDL3280A), Avelumab (Bavencio), and Durvalumab (Imfinzi, MEDI-4736).

Exemplary anti-Tim3 (also known as hepatitis A virus cellular receptor 2 or HAVCR2) antibodies that can be used in the methods described herein include those that bind to human Tim3; exemplary Tim3 sequences are provided at NCBI Accession No. NP_116171.3. Exemplary antibodies are described in WO2016071448; U.S. Pat. No. 8,552,156; and US PGPub. Nos. 20180298097; 20180251549; 20180230431; 20180072804; 20180016336; 20170313783; 20170114135; 20160257758; 20160257749; 20150086574; and 20130022623, and include LY3321367, DCB-8, MBG453 and TSR-022.

Exemplary anti-Lag3 antibodies that can be used in the methods described herein include those that bind to human Lag3; exemplary Lag3 sequences are provided at NCBI Accession No. NP_002277.4. Exemplary antibodies are described in Andrews et al., Immunol Rev. 2017 March; 276(1):80-96; Antoni et al., Am Soc Clin Oncol Educ Book. 2016; 35:e450-8; US PGPub. Nos. 20180326054; 20180251767; 20180230431; 20170334995; 20170290914; 20170101472; 20170022273; 20160303124, and include BMS-986016.

Exemplary anti-TIGIT antibodies that can be used in the methods described herein include those that bind to human TIGIT; an exemplary human TIGIT sequence is provided at NCBI Accession No. NP_776160.2. Exemplary antibodies include AB154; MK-7684; BMS-986207; ASP8374; Tiragolumab (MTIG7192A; RG6058); (Etigilimab (OMP-313M32)); 313R12. See, e.g., Harjunpaa and Guillerey, Clin Exp Immunol 2019 Dec. 11[Online ahead of print], DOI: 10.1111/cei.13407; 20200062859; and 20200040082.

Interferon alfa-2b, e.g., Peginterferon alfa-2b, can also be used.

In some embodiments, talimogene laherparepvec (a genetically modified oncolytic viral therapy) is used.

See, e.g., Luke and Schwartz, Clin Dermatol. 2013 May-June; 31(3): 290-297; Luke et al., Nat Rev Clin Oncol, 14 (8), 463-482 (2017); Leonardi et al., Int J Oncol. 2018 April; 52(4): 1071-1080; Bhatia et al., Oncology (Williston Park). 2009 May; 23(6): 488-496.

In some embodiments, for subjects with a TCFr below the reference level, a vaccine that increases TCFr can be used. For example, immunostimulants such as growth factors (e.g. granulocyte and macrophage colony stimulating factor (GM-CSF)) and bioproducts from bacteria (e.g. Bacillus Calmette-Guérin (BCG) and *Corynebacterium parvum*); vaccines targeting melanoma cells directly, neoantigen or peptide-based vaccines, viral vector-based vaccines, and dendritic cell vaccines can be used; see, e.g., Rodríguez-Cerdeira et al., Mediators Inflamm. 2017; 2017: 3264217; Pasquali et al., Cochrane Database Syst Rev. 2018 February; 2018(2): CD011123; Yang et al., Front Oncol. 2017; 7: 61; Tanner et al., Front Immunol. 2019; 10: 1317. In preferred embodiments, a neoantigen vaccine is used, e.g., as described in Ott et al., Nature. 2017 July 13; 547(7662): 217-221. These can be administered systemically or intratumorally (e.g., into a site where the tumor was after excision).

EXAMPLES

The invention is further described in the following examples, which do not limit the scope of the invention described in the claims.

Materials and Methods

The following materials and methods were used in the Examples below.

Melanoma Samples

Utilizing institutional databases, we identified archival primary melanomas with a tumor thickness>1 mm. All melanomas were complete excision biopsies with narrow (2 mm) margins, none were partial biopsies or re-excision specimens. Samples were formalin-fixed and paraffin-embedded (FFPE) for routine histopathological examination and had been stored for 2-19 years. After surgery, patients were monitored for disease recurrence. When selecting patients, we matched the number of patients who died related to melanoma and who were alive per thickness group (T2 (1-2 mm), T3 (2-4 mm), T4 (>4 mm)) after five years. Samples were derived from the Melanoma Institute Australia, Sydney, Australia, n=271; Brigham and Women's Hospital, Boston, USA, n=18; and Zealand University Hospital, Roskilde, Denmark n=48.

All patients provided written informed consent prior to their inclusion in the study. Ethics approval was obtained from the institutional review boards at all three collection center.

gDNA Extraction

Total genomic DNA was extracted from 5×10 µm sequential scrolls of archival FFPE samples with the QIAamp DNA Micro Kit (Qiagen). Blocks were carefully inspected prior to the cutting of scrolls to ensure that the tumor, rather than normal surrounding tissue, was sampled. Paraffin was dissolved by adding 1000 µl xylene and afterwards 2×1000 µl 100% ethanol to the samples. Samples were incubated in buffer ATL and 40 ul Proteinase K at 56° C. overnight. Further lysis of samples in buffer AL was carried out at 70° C. for 10 min, before 400 µl of 100% ethanol was added. Between each incubation step samples were centrifuged at full speed (20,000×g). Lysates were then transferred to QIAamp MinElute Columns and all further processing steps followed manufacturer instructions.

TCR Sequencing

Next-generation sequencing of the TCRB gene was performed using the immunoSEQ® Assay (Adaptive Biotechnologies) optimized for FFPE samples. As previously described in detail,[46,47] TCRB CDR3 regions were amplified by a multiplex, bias-controlled PCR with a pool of primer pairs targeting the V and J genes of T cells as well as primers targeting reference genes to quantitate the total nucleated cells in each sample. PCR products were sequenced on an Illumina NextSeq.

For analytical robustness, samples were analyzed for their T-cell fraction if they had a minimum of 500 total nucleated cells (n=199) and were also analyzed for their repertoire clonality if they also had a minimum of 100 T cells (n=158). T-cell fraction was calculated as the proportion of T cells in a sample relative to its total number of nucleated cells. Simpson clonality was calculated according to equation (1):

$$\text{Simpson clonality} = \sqrt{\Sigma p_i^2} \quad (1)$$

where $p_i$ is the proportional abundance of clone i in a sample's repertoire and ranges in value from 0 to 1; a value closer to 0 indicates a highly polyclonal repertoire and a value closer to 1 indicates a highly oligoclonal repertoire.

T-Cell Fraction (TCFr) Cut-Off Optimization

Figure 4A:
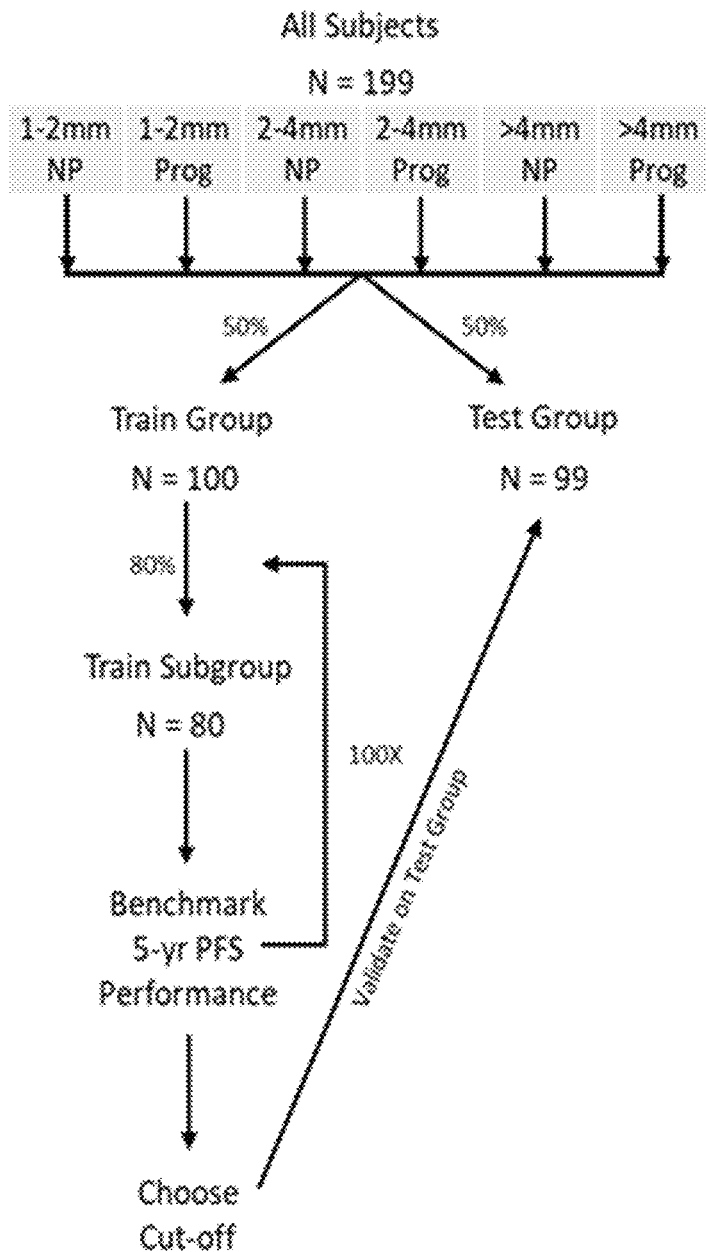
FIGS. 4A-J. T-cell fraction cut-off optimization and validation. (a) Flowchart illustrating the data partitioning and subsampling approach to first optimize and then internally validate a TCFr cut-off that identifies patients at risk for disease recurrence. (b) Precision-Recall F-score and (d) true positive rate (TPR: proportion of patients below the cut-off who experienced disease recurrence) for seven different TCFr cut-off values as measured by bootstrapping the training group 100 times. Each dot represents one bootstrap per TCFr value. (c) Precision-Recall Curve of 100 training cohort bootstraps colorized by TPR. (e) Second order derivates of F-score versus TCFr cut-off colorized by the TPR; each dot represents one bootstrap per TCFr value, which were fitted with a LOESS curve. The lowest TCFr where the F-score and TPR approximates zero is at 0.2 (=20%), highlighted by the orange box. (f) Among high and low TCFr samples, no difference is detected between thickness groups. Kruskal-Wallis Test and post-hoc Kruskal-Dunn Test, $p_{KW}$ TCFr high=0.299, $p_{KW}$ TCFr low=0.378. (g) Simpson's clonality is comparable for all thickness groups ($p_{KW}$=0.255) and has a small but significant difference between low and high TCFr samples (two-sided Wilcoxon Rank Sum Test, $median_{Low}$=0.118 vs $median_{High}$=0.0978). (f,g) Group sizes: TCFr high: 1-2 mm, n=25; 2-4 mm, n=26; >4 mm, n=19. TCFr low: 1-2 mm, n=27; 2-4 mm, n=49; >4 mm, n=53. (h) This primary melanoma cohort has a higher median TCFr in comparison to TCFr of published metastatic melanomas. Two-sided Wilcoxon Rank Sum Test; primary, n=199; metastatic, n=106. (i,j) Kaplan-Meier curves of (i) PFS for test cohort and (j) OS for combined metastatic cohort stratified by the 20% TCFr cut-off. Cox regression estimates; p-values by two-sided Z-Test and Likelihood ratio test (LRT). (a-j) For all box plots: the bold line indicates the median; box illustrates lower and upper quartiles; whiskers show the lowest and highest data point still within 1.5× of interquartile range from lower or upper quartile, respectively.
Figure 4B:
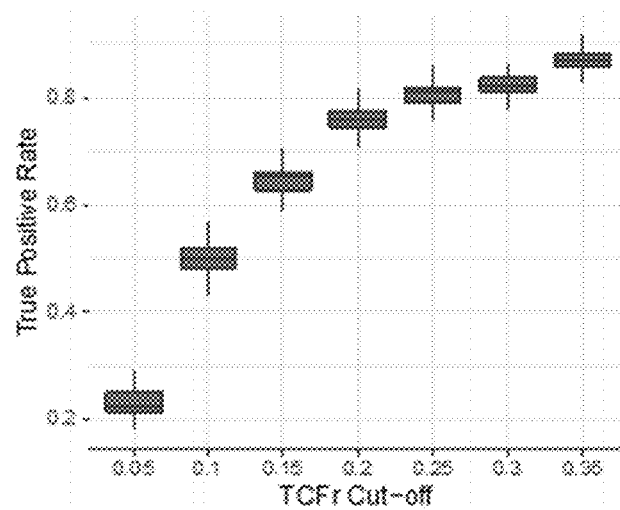
Figure 4C:
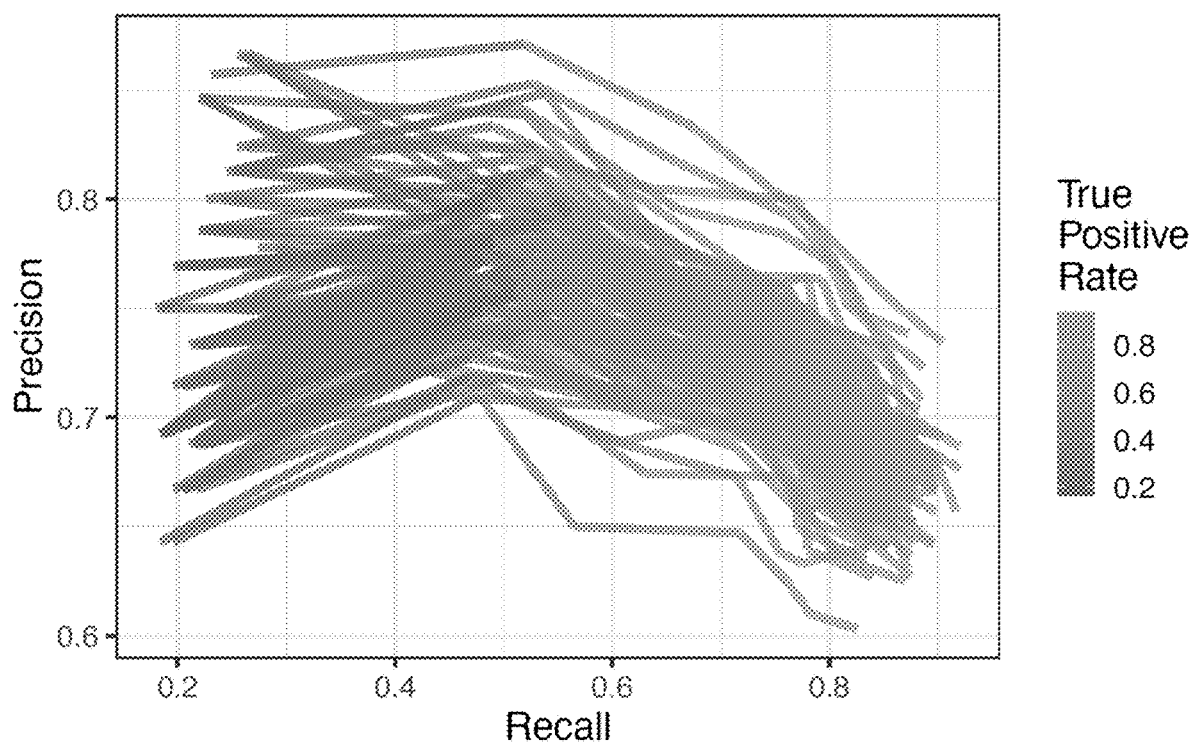
Figure 4D:
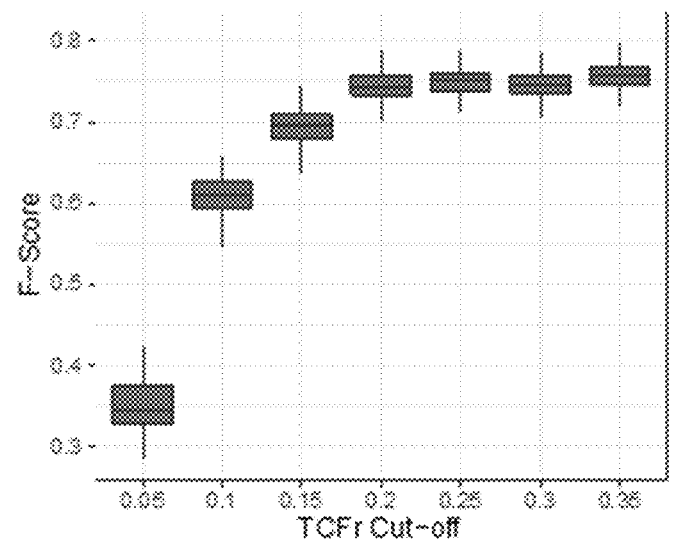

To reduce bias in selecting a TCFr that optimally identifies patients at risk for recurrence, we implemented a number of data partitioning methods (FIG. 4a). First, the cases were randomly partitioned into two groups, training (n=100) and testing (n=99), in a manner that preserved the proportions of tumor thickness and progressors in the aggregated collection of cases. We then bootstrapped the training group by randomly subsampling 80% of the data 100×. For each subsample, a grid search was performed across seven TCFr values (0.05, 0.1, 0.15, 0.2, 0.25, 0.3, 0.35) and the precision-recall F-score, true-positive rate (TPR: proportion of patients below the cut-off who experienced disease recurrence), and true-negative rate (TNR: proportion of patients above the cut-off who remain disease-free) were calculated for predicting disease progression at five years post-resection. The precision-recall F-score was chosen over the area under the receiver-operator curve due to its robustness against imbalanced data labels. The TPR (and not the TNR) was prioritized alongside the F-score as part of our heuristic for cutoff selection to ensure at-risk patients are identified. We then calculated the first and second order derivatives of the F-score and TPR versus the TCFr cut-off and selected the first (i.e., lowest) cutoff where the second order derivatives approximated zero. The chosen cutoff was then applied to the test group and considered valid if the Cox proportional-hazard model yielded a p-value≤0.05, indicating a significant difference in progression-free survival intervals between patients above versus below the cutoff.

TIL Grading

All samples with usable TCRB HTS results were regraded for tumor infiltrating lymphocytes (TILs) by an experienced dermatopathologist (MCM) who was "blinded" to the identity of the samples. One diagnostic H+E stained slide was used and two different grading systems applied: (a) TIL briskness assessment originally proposed by Clark et al.[9] which differentiates between absent, non-brisk and brisk TIL infiltration (n=199); (b) a recently proposed grading by the Melanoma Institute Australia which distinguishes four grades (0 to 3) based on density (mild, moderate or marked) and distribution (focal, multifocal or diffuse) of lymphocytes in the dermal tumor component (n=153).[10]

Immunofluorescence Staining

FFPE slides were baked at 58° C. for 20 min, deparaffined in Xylene for 30 min plus 10 min, and rehydrated in serial passage through declining graded ethanol. Heat-induced epitope retrieval was performed at 110° C. for 15 min with 1× Target Retrieval Solution (catalog number 51699, Dako) in a decloaking chamber (BioCare Medical). Slides were then blocked with serum-free protein block (X0909, Dako) for 20 min at RT and incubated with rabbit anti-CD3 antibody (1:150, A0452, Dako) and mouse (mIgG1) anti-Sox10 antibody (1:25, ACI3099, BioCare Medical) for 1 hour at RT. After washing, immunofluorescent signal was visualized with Alexa Fluor 594 conjugated goat anti-rabbit IgG antibody (1:1000, A11012, Invitrogen) and Alexa Fluor 488 conjugated goat anti-mIgG1 antibody (1:1000, A21121, Invitrogen) for 30 min at RT followed by another washing step. Slides were covered with DAPI mounting medium (H-1500, Vector Laboratories). The staining was reviewed using Mantra Quantitative Pathology Image System (PerkinElmer).

Multiplex Immunohistochemistry

Formalin-fixed paraffin-embedded (FFPE) tissue were cut at 3 µm thickness; tissue sections were taken from the matching FFPE tissue that was used for TCRB HTS. Slides were heated at 65° C. for 30 minutes then deparaffinized in xylene for 5 minutes (×2), and rehydrated sequentially through declining graded ethanol. Slides were then rinsed in $H_2O$ and placed in tris-buffered saline tween buffer (TBST). Antigen retrieval was performed in a Biocare Decloaking Chamber (Biocare Medical) for 10 minutes at 110° C. using AR9 buffer (Perkin Elmer). Slides were cooled to room temperature in a water bath before staining. All staining was performed using an intelliPATH FLX® Automated Slide Stainer (Biocare Medical). Slides were blocked with 3% $H_2O_2$ (Sigma Aldrich) diluted in TBST for 5 minutes. Then, slides were incubated with the primary antibody for FoxP3 (Abcam, 236A1E7, 1:1000), CD103 (Abcam, EPR4166(2), 1:800), CD8 (Dako, C8/144B, 1:1000), CD4 (Biocare Medical, 4B12, 1:400), CD3 (Cell Marque, MRQ-39, 1:2000) or CD39 (Abcam, EPR20627, 1:2000), made up in either Da Vinci Green (Biocare Medical), Antibody Diluent/Block (Perkin Elmer) or Van Gough Yellow (Biocare Medical), for 30 minutes. Slides were then incubated with either Opal Polymer HRP Ms+Rb (Perkin Elmer) for 30 minutes, or Mach 3 Mouse probe antibody (Biocare Medical) for 5 minutes and Mach 3 Mouse HRP antibody (Biocare Medical) for 5 minutes. Afterwards slides were incubated with Opal fluorophore diluted in TSA (Perkin Elmer, 1:100), then staining was repeated from antigen retrieval onwards to remove the previous antibody and add subsequent antibodies in the panel. Single colour control slides were stained alongside the test panel to determine background staining and to create a library for later spectral unmixing. After staining the final antibody, slides were incubated with Spectral DAPI (Perkin Elmer, 1:2000) diluted in TBST for 5 minutes and coverslipped in Prolong Diamond Antifade Mountant (Thermo Fisher Scientific).

Multispectral Imaging and Analysis

All imaging was performed using the Vectra 3.0.5 Automated Quantitative Pathology Imaging system (Perkin Elmer). 20× multispectral images covering the entire tumour for each tissue were acquired using the DAPI, FITC, Cy3, Texas Red and Cy5 fluorescent channels. Spectral unmixing of multispectral images was performed in inForm v2.4.2 (Akoya Biosciences) based on signals acquired from single colour controls.

Multispectral images were exported for image analysis in HALO v2.3 (Akoya Biosciences) and stitched together to create a single high-resolution multispectral image for each tumour, upon which image analysis was performed. An algorithm was developed to detect individual cells based on nuclear DAPI staining. Positivity thresholds were set for each marker based on staining intensity. Data for each cell, including marker expression, was exported for secondary analysis in TIBCO Spotfire v7.8. Cell phenotyping was performed based on cell marker expression as outlined in the table below, and total cell counts as well as cell counts for each phenotype were exported from TIBCO Spotfire.

| Cell type | Phenotype |
| --- | --- |
| CD4+ T cells | DAPI+ CD3+ CD4+ CD8− |
| CD8+ T cells | DAPI+ CD3+ CD8+ CD4− |
| T cells | |
| CD4+ T cells | DAPI+ CD3+ CD4+ CD8− |
| CD8+ T cells | DAPI+ CD3+ CD8+ CD4− |
| Tregs | DAPI+ CD3+ CD4+ CD8− FoxP3+ |
| CD39+ CD8+ T cells | DAPI+ CD3+ CD8+ CD4− CD39+ |
| CD103+ CD8+ T cells | DAPI+ CD3+ CD8+ CD4− CD103+ |
| CD39+ CD103+ CD8+ T cells | DAPI+ CD3+ CD8+ CD4− CD39+ CD103+ |

Statistics and Reproducibility

Analyses were performed using the immunoSEQ Analyzer 3.0 and R 3.5.1.[48] Associations between categorical and numeric variables were tested using a Wilcoxon Rank Sum Test (two categorical groups) or a Kruskal-Wallis Test (three or more categorical groups). Associations between two categorical variables were tested using Fisher's Exact Test. Associations between two numeric variables were tested using Spearman's Rank-Order Correlation. To measure the impact of individual covariates on progression-free survival (PFS) following melanoma resection, univariate Cox proportional-hazard models were generated and assessed for statistical significance by Likelihood ratio tests. An analysis of deviance was performed to determine superiority between two Cox models, which uses a Chi-square test to compare the models' log-likelihood values. The relative importance of five histopathological features, including molecular TCFr, in predicting patient outcomes was estimated by a gradient boosted model (n=193) with a Cox proportional-hazards distribution, 1000 trees, a learning rate of 0.01, and 5-fold cross-validation. P-values≤0.05 were considered statistically significant unless otherwise specified.

At least 150 FFPE samples were required to achieve ≥80% statistical power with a type I error probability of 5% for a range of potential effect sizes (HR: 0.5-0.8). An interim analysis found that the success of TCRB sequencing depended on the age of the FFPE sample, and many of our samples dated back almost two decades (median 9 years). We therefore conservatively estimated that 30-50% might fail TCR sequencing quality controls for sample adequacy and targeted a total collection of 300 primary melanomas, ultimately collecting 337. 313 cutaneous, 22 acral lentiginous and 2 mucosal melanomas were included in this study.

The study was designed in accordance with the REMARK guideline (reporting recommendations for tumor prognostic studies).[49]

Example 1. Patients

We performed high-throughput TCRB sequencing in 337 archival FFPE primary melanomas with a tumor thickness of at least 1 mm. All tumors had been surgically resected as complete excisional biopsies for diagnosis with narrow (max. 2 mm) margins (FIG. 1). No patient received any neoadjuvant therapies, and patients underwent subsequent surgery with intent to cure at a later time point. If patients presented with positive regional lymph nodes at initial diagnosis, these were also completely resected. After surgery with intent to cure, all patients were classified as disease-free.

After quality control, TCRB repertoire metrics could be analyzed in 209 (62%) of the FFPE samples and 199 of these had available PFS metadata (FIG. 1). Sample adequacy for analysis depended primarily on the age of the FFPE sample; while >90% of 1-3 year old samples were analyzable, 60-75% of 3+ year old samples could be included (Extended Data FIG. 1a,b). The median age of FFPE samples was 9 years (range: 1-19). Patients were partitioned by random selection into training (n=100) and test (n=99) cohorts, controlling only for similar representations of T stages and rates of disease progression. Patients were followed up for a median of 54 months (range: 2-218 mos), and 92 patients (46.2%) experienced recurrence of disease, while 75 (37.7%) died due to melanoma. The rate of disease progression appeared to have two inflection points, at two and five years (0-2 yrs 18.5%, 2-5 yrs 3.7%, >5 yrs 0.5% progressions per year).

Figure 2A:
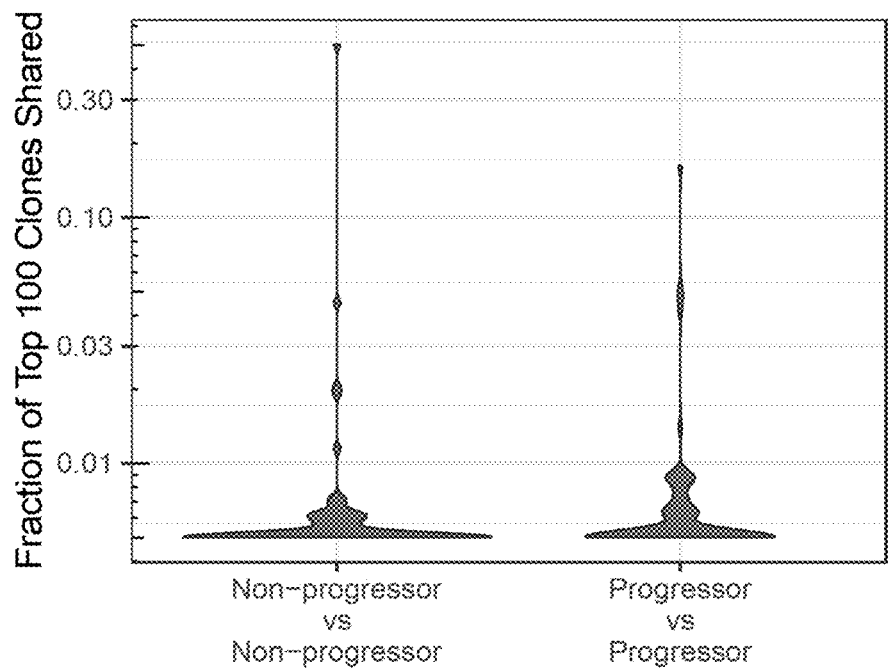
FIGS. 2A-I. TCRB CDR3 repertoire sharing and distribution of insertions and deletions. (a,b) Analyses of TCRB repertoire sharing within subgroups of non-progressors and progressors reveals comparably low fractions of shared clones between two or more patients. (a) illustrates the fraction of clones shared among the top 100 clones for each sample (i.e., Jaccard Index). (b) illustrates the fraction of T cells shared among these top 100 clones. (c) Distribution of TCRB CDR3 length (in nucleotides) does not differ between the repertoires of progressors and non-progressors. (d-i) Frequency distributions of the number of deletions or insertions per site. (d) Vdels, (e) Jdels, (f) D5dels, (g) D3dels, (h) N1ins, (i) N2ins do not differ between progressors and non-progressors. (a-i) Non-Progressors, n=107 primary melanoma samples; Progressors, n=92. Violin plots show distribution of the data, dots represent data points. For all box plots, the bold line indicates the median; box illustrates lower and upper quartiles; whiskers show the lowest and highest data point still within 1.5× of interquartile range from lower or upper quartile, respectively; all dots are outliers.
Figure 2B:
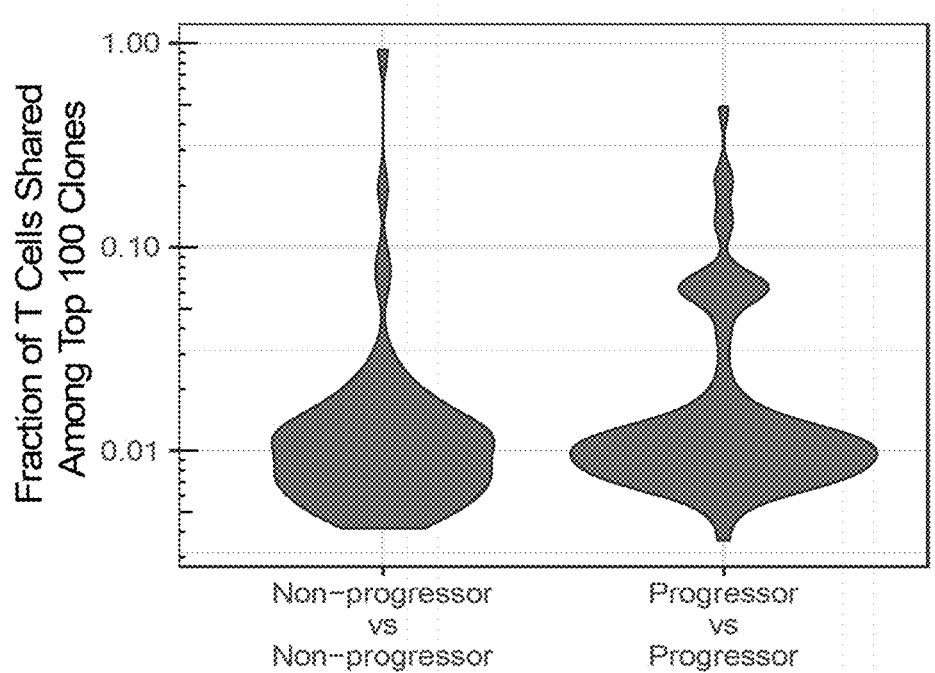
Figure 2C:
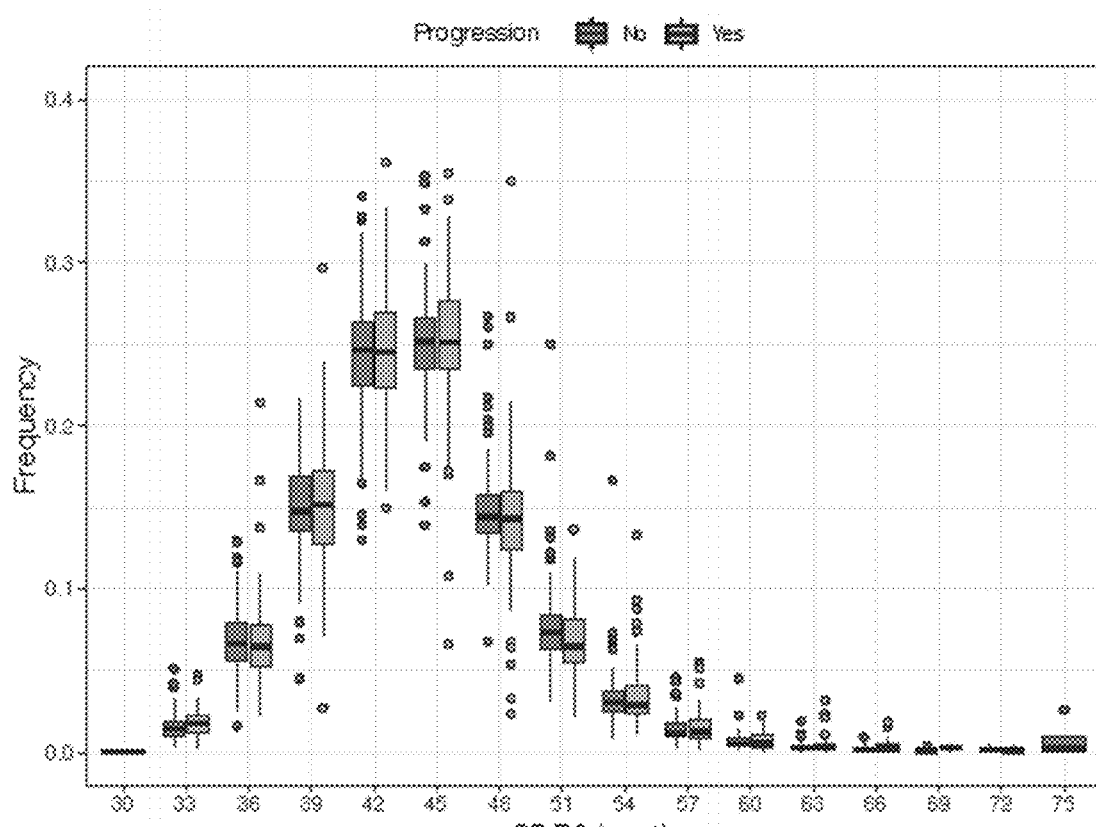
Figure 2D:
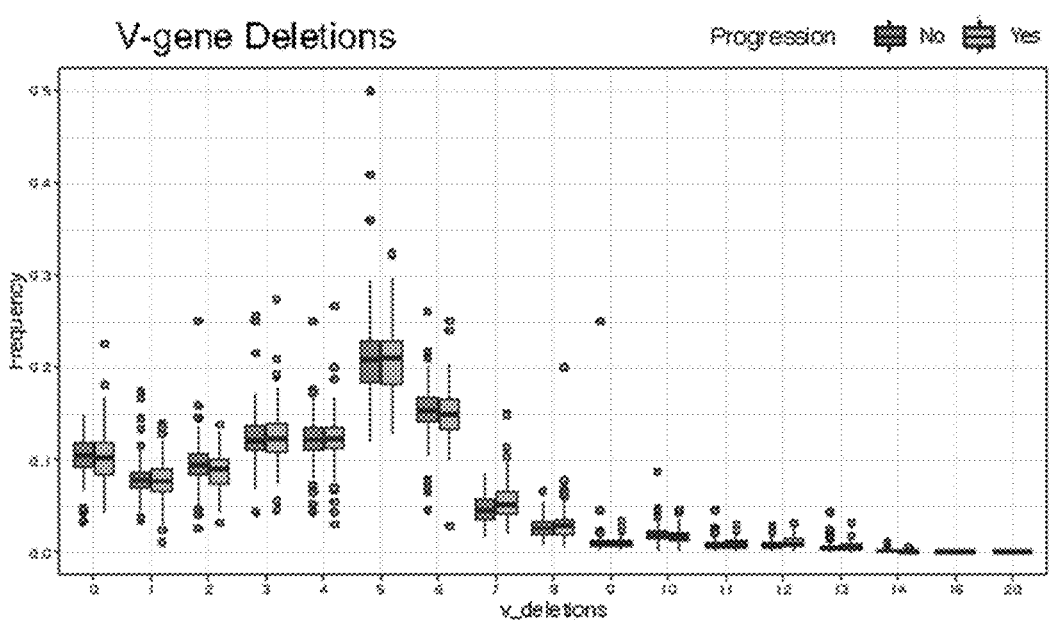
Figure 2E:
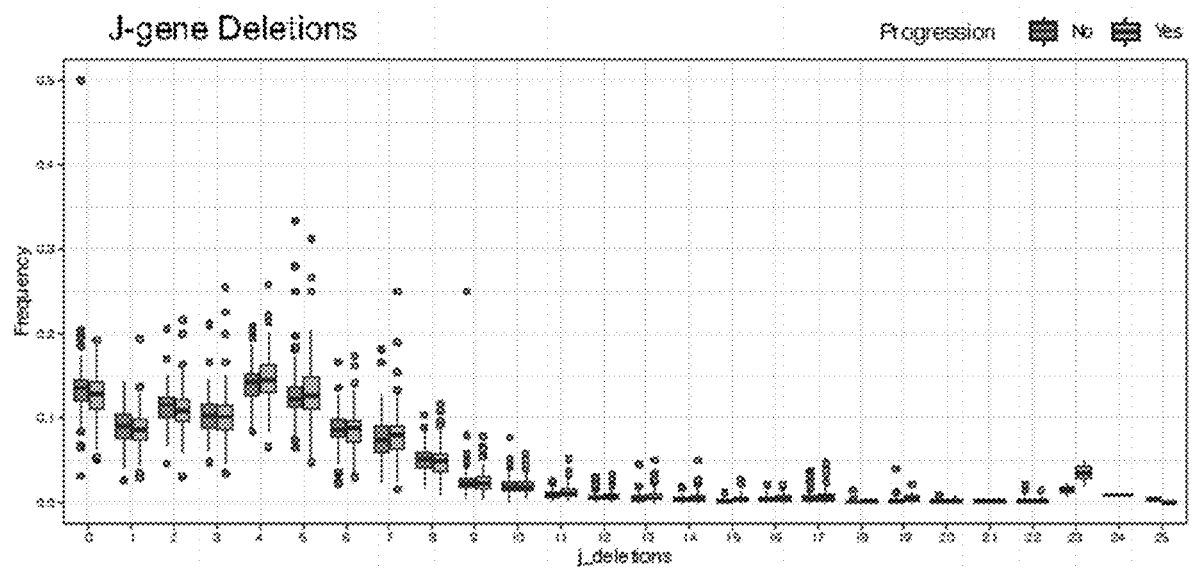
Figure 2F:
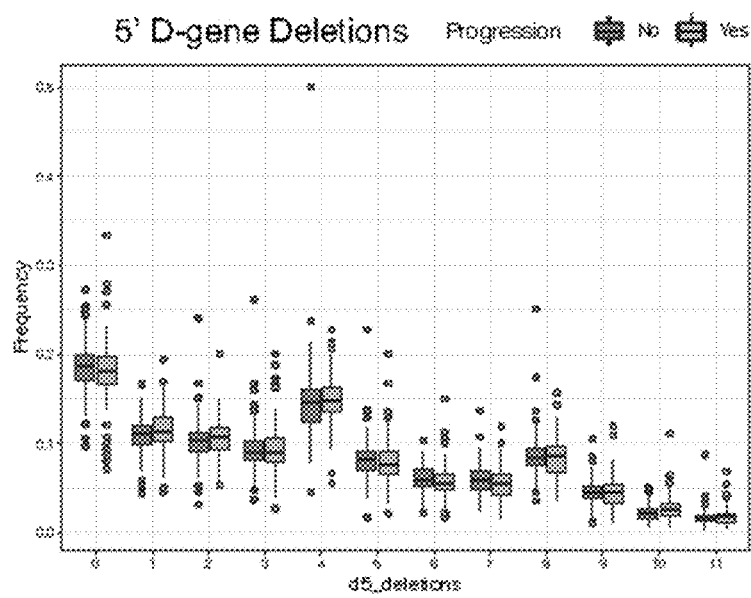
Figure 2G:
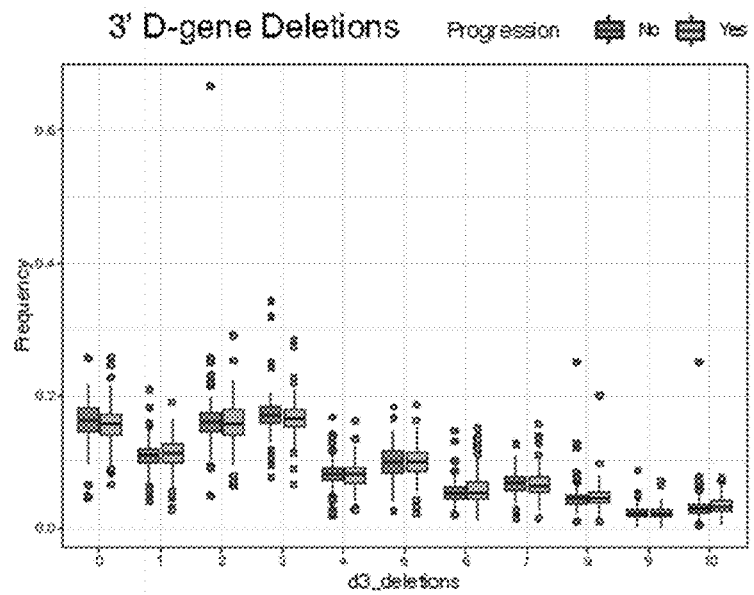
Figure 2H:
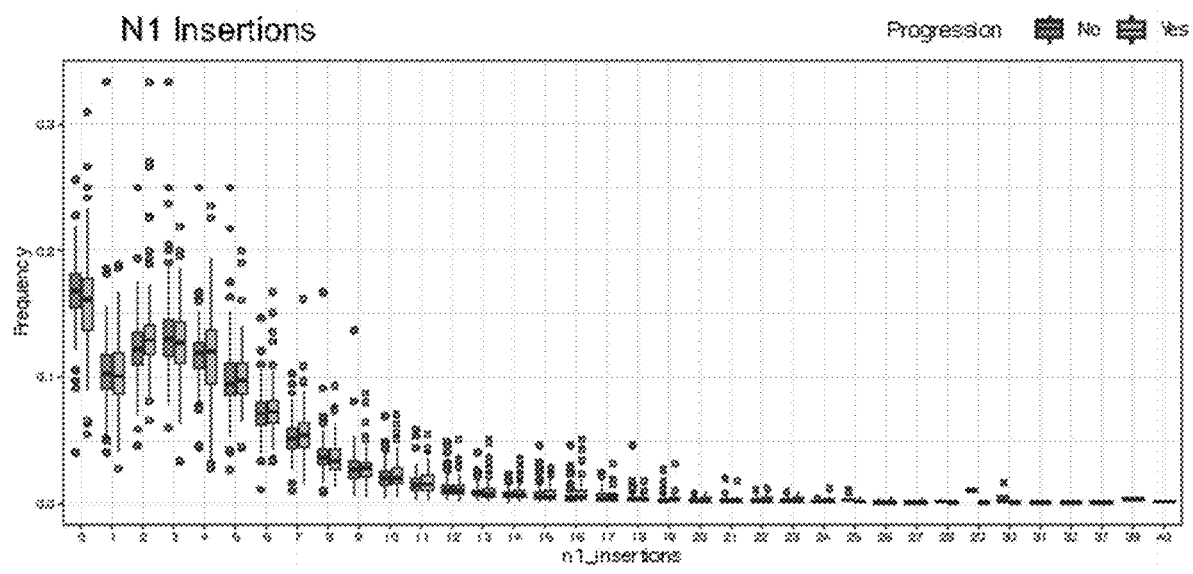
Figure 2I:
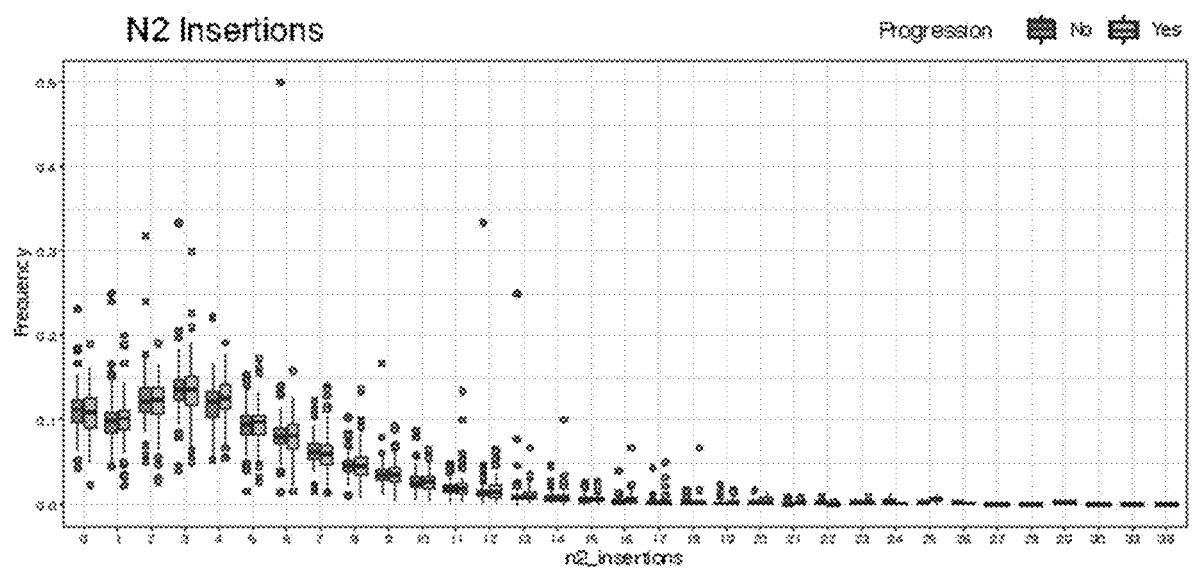

Example 2. Infiltrating T Cells are Polyclonal and Unique for Each Patient's Primary Melanoma The TCRB repertoire was largely unique to each melanoma patient with only 2% of CDR3 sequences shared between at least two patients. Progressors and non-progressors had equally low fractions of T cells shared among the top 100 clones per patient (FIG. 2a,b). Repertoire clonality of the tumor T-cell infiltrate did not differ between progressors and non-progressors. Consistent with this finding, we did not detect any difference in CDR3 length, in numbers of deletions or insertions at any of the six re-combinatorial sites, nor TCRB-V-family or TCRB-J-gene usage (FIG. 2c-i).

Example 3. T-Cell Fraction (TCFr) is an Independent Predictor of PFS

Figure 3A:
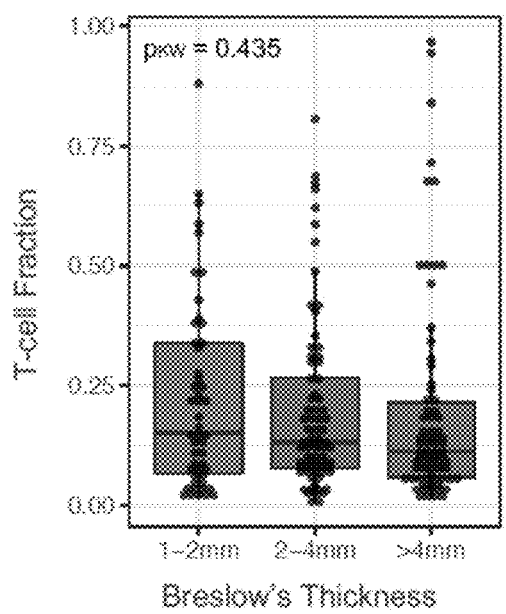
FIGS. 3A-D. T-cell fraction is not associated with other clinical or histopathological factors. (a) TCFr is similar among all tested thickness groups. Kruskal-Wallis Test; 1-2 mm, n=50 independent samples; 2-4 mm, n=75; >4 mm, n=74. Box plots: the bold line indicates the median; box illustrates lower and upper quartiles; whiskers show the lowest and highest data point still within 1.5× of interquartile range from lower or upper quartile, respectively; all dots are data points. (b) TCFr is not correlated with tumor thickness; n=199, Spearman's correlation test (Rho and p-value listed in plot). (c) TCFr is completely independent of any other relevant clinical and histopathological feature; n=199. P-values for associations between pairwise combinations of continuous and discrete variables; associations were tested with Spearman's correlation test, two-sided Wilcoxon Rank Sum or Kruskal-Wallis Test, or two-sided Fisher's exact test, as appropriate and post-hoc corrected for multiple testing with Benjamini-Hochberg. Statistically significant associations are highlighted in green. (d) Relationship between Simpson's clonality and T cell fraction by thickness group. Clonality is weakly correlated with T cell fraction. Spearman's correlation test, Rho and p-values listed in plots; 1-2 mm, n=42 independent samples; 2-4 mm, n=59; >4 mm, n=57.
Figure 3B:
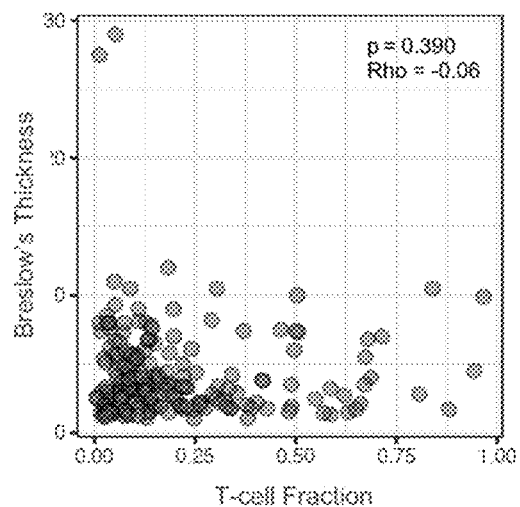

T-cell fraction and repertoire clonality were similar for all melanoma T categories and had an orthogonal relationship to tumor thickness (FIG. 3a,b). Univariate Cox regression revealed that TCFr was a significant predictor of PFS (HR=0.81 per 0.1 increase, p=2.07E-4, LRT p=2.33E-5), while Simpson clonality was not (Table 2a). TCFr was also predictive of overall survival (HR=0.80 per 0.1 increase, p=1.83E-4, LRT p=1.61E-5; Table 2b). Tumor thickness was the strongest predictor of PFS (HR=1.08 per 1 mm increase, p=1.62E-4, LRT p=0.00133). Other covariates identified as predictors of PFS included mitotic rate, ulceration, positive regional LN, and patient age (Tables 2a,b).

variability in other clinical factors), both TCFr HR ratios were within each other's 95% confidence interval (train group: HR 0.84 per 0.1 increase, CI 0.73-0.97, p=0.0227, LRT p=0.01; test group: HR 0.77 per 0.1 increase, CI 0.65-0.92, p=0.00339, LRT p=6.00E-4). This robustness and orthogonality underlines TCFr's unique importance in contributing new prognostic information to PFS models.

TABLE 2a 5-year PFS Hazard Ratios

| Variable | HR | Lower CI | Upper CI | Per Unit Increase | P-value | LRT P-value |
|---|---|---|---|---|---|---|
| Thickness | 1.08 | 1.04 | 1.13 | 1 mm | 0.000162 | 0.00133 |
| Age | 1.02 | 1.01 | 1.03 | 1 year | 0.00541 | 0.00444 |
| Sex: M (vs F) | 0.87 | 0.61 | 1.26 | — | 0.46 | 0.462 |
| Nodal Disease: Present (vs Absent) | 2.44 | 1.70 | 3.49 | — | 1.07E-06 | 1.39E-06 |
| Ulceration: Present (vs Absent) | 1.69 | 1.18 | 2.43 | — | 0.00433 | 0.00435 |
| Mitotic Rate | 1.03 | 1.01 | 1.05 | 1 mitosis/mm$^2$ | 0.00167 | 0.000413 |
| Location: Extremities (vs Head and Neck) | 1.07 | 0.71 | 1.62 | — | 0.72112 | 0.03451 |
| Location: Other (vs Head and Neck) | 0.73 | 0.10 | 5.36 | — | 0.76287 | 0.03451 |
| Location: Trunk (vs Head and Neck) | 0.57 | 0.34 | 0.93 | — | 0.02584 | 0.03451 |
| Simpson's Clonality | 0.96 | 0.76 | 1.21 | 0.1 | 0.751 | 0.748 |
| T-cell Fraction (continuous) | 0.81 | 0.72 | 0.91 | 0.1 | 0.000207 | 2.33E-05 |
| T-cell Fraction: ≥20% (vs <20%) | 0.39 | 0.25 | 0.59 | — | 1.28E-05 | 3.00E-06 |

Abbreviations: HR-Hazare Ration, CI-95% Confidence Interval, p-value by two-sided Z-Test, LRT-Likelihood-ratio test. N = 199.

TABLE 2b 5-year OS Hazard Ratios

| Variable | HR | Lower CI | Upper CI | Per Unit Increase | P-value | LRT P-value |
|---|---|---|---|---|---|---|
| Thickness | 1.05 | 1.00 | 1.10 | 1 mm | 0.0357 | 0.0603 |
| Age | 1.02 | 1.00 | 1.03 | 1 year | 0.0168 | 0.0147 |
| Sex: M (vs F) | 1.06 | 0.72 | 1.57 | — | 0.755 | 0.754 |
| Nodal Disease: Present (vs Absent) | 1.92 | 1.32 | 2.80 | — | 0.000663 | 0.000746 |
| Ulceration: Present (vs Absent) | 1.57 | 1.07 | 2.30 | — | 0.0214 | 0.0212 |
| Mitotic Rate | 1.02 | 0.99 | 1.04 | 1 mitosis/mm$^2$ | 0.142 | 0.162 |
| Location: Extremities (vs Head and Neck) | 0.85 | 0.55 | 1.31 | — | 0.4614205 | 0.151801 |
| Location: Other (vs Head and Neck) | 0.73 | 0.10 | 5.34 | — | 0.7583885 | 0.151801 |
| Location: Trunk (vs Head and Neck) | 0.56 | 0.34 | 0.93 | — | 0.0276621 | 0.151801 |
| Simpson's Clonality | 0.92 | 0.71 | 1.19 | 0.1 | 0.522 | 0.511 |
| T-cell Fraction (continuous) | 0.80 | 0.71 | 0.90 | 0.1 | 0.000183 | 1.61E-05 |
| T-cell Fraction: ≥20% (vs <20%) | 0.37 | 0.24 | 0.59 | — | 2.04E-05 | 4.00E-06 |

Abbreviations: HR-Hazard Ratio, CI-95% Confidence Interval, p-value by two-sided Z-Test, LRT-Likelihood-ratio test. N = 199.

Figure 3C:
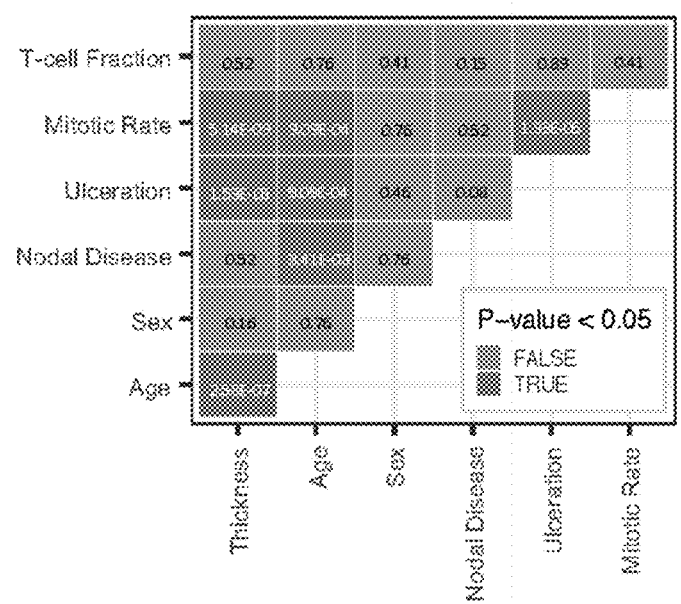
Figure 3D:
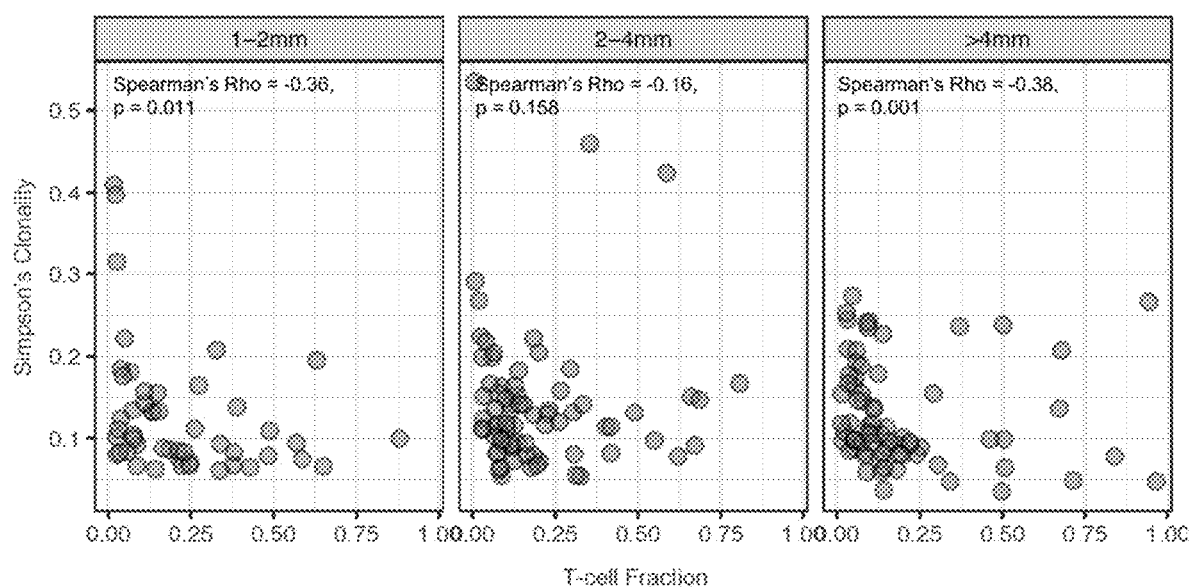
Figure 4E:
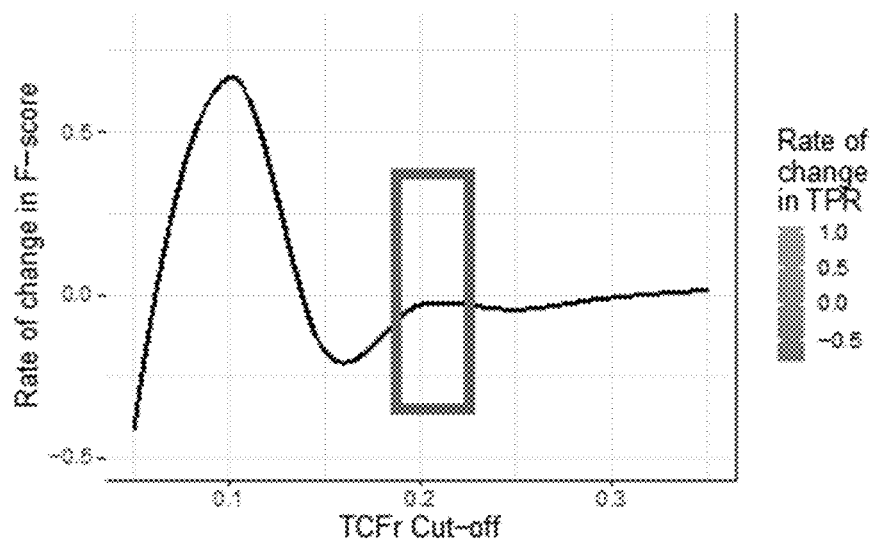
Figure 4F:
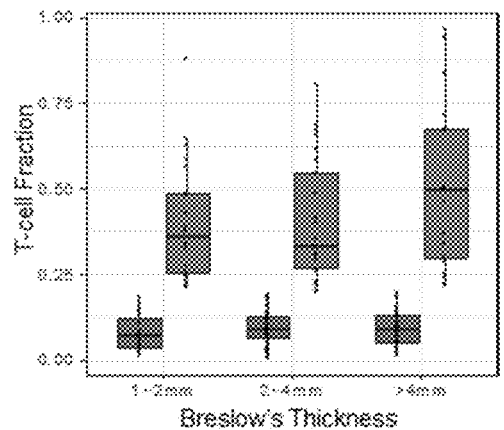
Figure 4G:
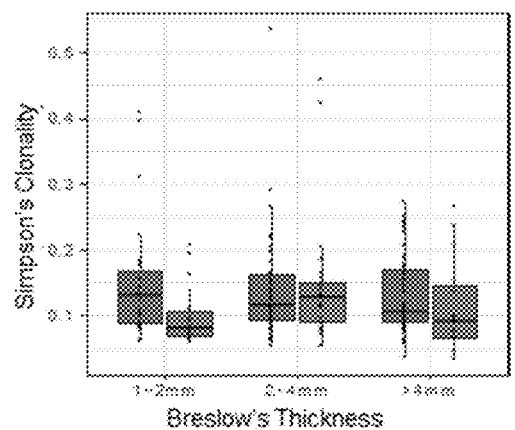
Figure 4H:
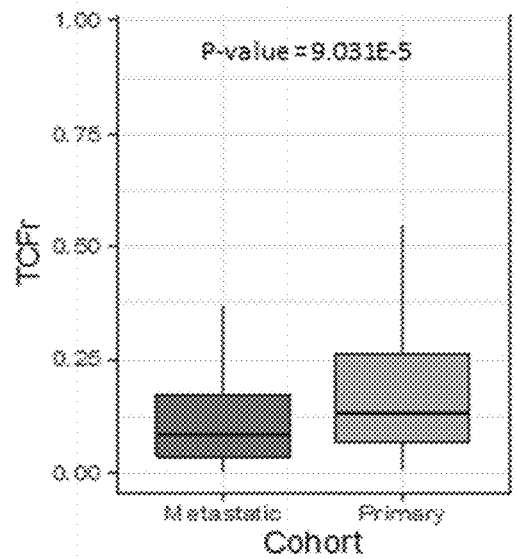
Figure 4I:
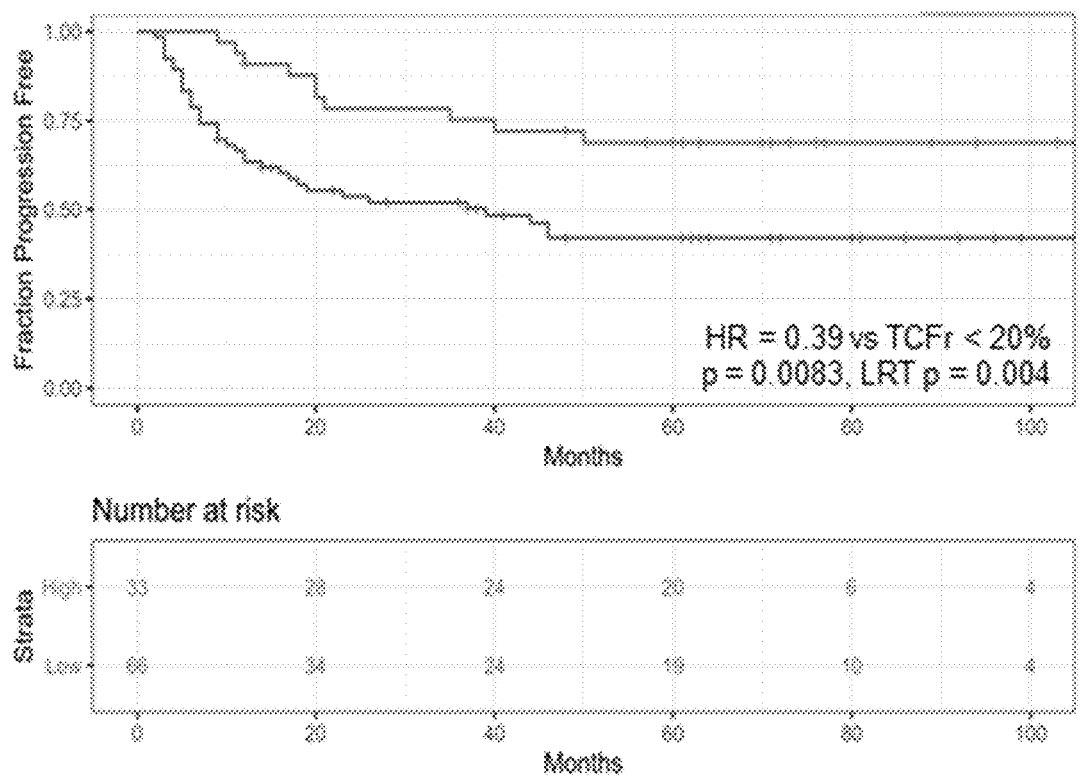
Figure 4J:
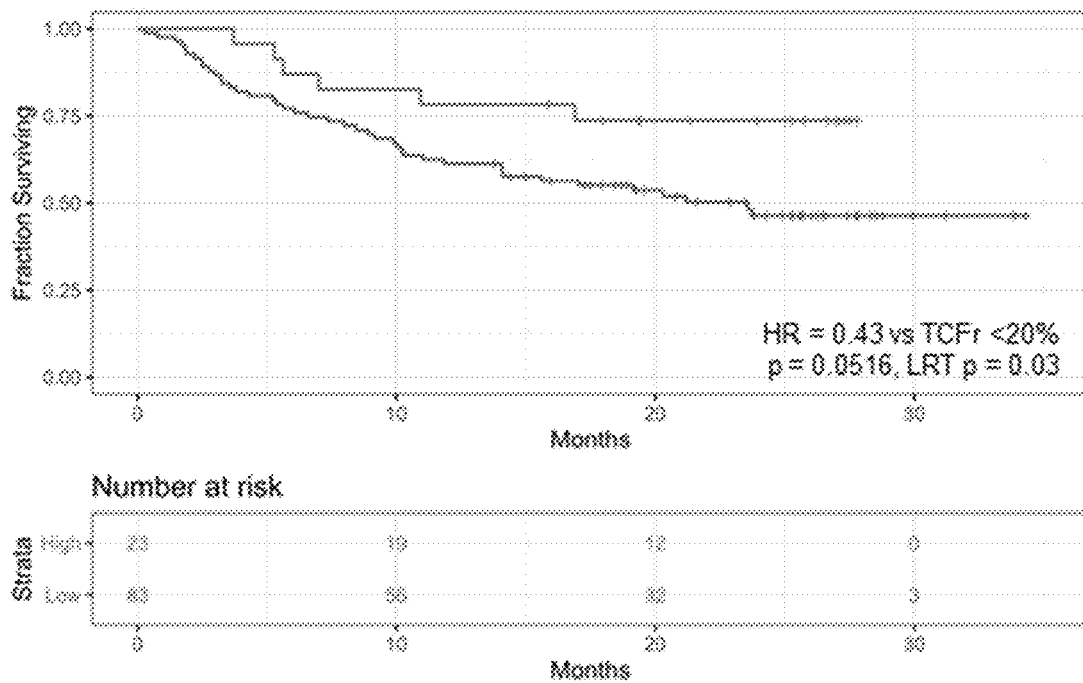

We next explored possible associations between these covariates. In line with prior studies, greater tumor thickness was associated with a higher mitotic rate, presence of ulceration, and patient age (FIG. 3c). In contrast, TCFr was not associated with any clinical or histological variable and was thus a fully independent predictor of progression (FIG. 3c,d). Based on this observation, we tested the prognostic influence of TCFr for the training and test cohorts, respectively. Despite random partitioning (which can introduce Example 4. Optimizing Prognostic TCFr Cut-Off To make TCFr an interpretable and clinically useful prognostic marker, we translated its continuous scale (from 0 to 1) into a categorical variable (high versus low) by identifying a cut-off value that best discriminated patients with disease recurrence from those who remained disease-free at five years post-resection. The training group was repeatedly subsampled and a grid search of seven TCFr cut-offs, from 0.05 to 0.35, were benchmarked by precision-recall F-score, TPR, and TNR for each iteration (FIG. 4a-e, FIG. 9a-d). An optimal cut-off was chosen based on the lowest TCFr where the rate of improvement in the F-score and TPR approximated zero. In the training cohort, the optimal cut-off occurred at a TCFr of 20% (FIG. 4e). We confirmed that the TCFr did not vary by tumor thickness within high TCFr and low TCFr tumors (FIG. 4f); similarly, Simpson clonality did not vary between high versus low TCFr tumors within tumor thickness groups (FIG. 4g). When applied to the test cohort, 33 patients with a TCFr 20% had significantly less risk of progression than 66 patients with a TCFr<20% (HR=0.39 vs TCFr<20%, p=0.0083, LRT p=0.004), validating our TCFr cut-off selection (FIG. 4i). At five years post-resection, 31% of patients with TCFr≥20% and 57% with TCFr<20% experienced recurrence. The true negative and true positive rates for the 20% TCFr cut-off subdivided by thickness group, stage and nodal status were determined.

To further explore the potential use of TCFr as a predictive biomarker, we sought to test the 20% TCFr cut-off on independent datasets. We elected to aggregate the TCR HTS data of two previously published cohorts of metastatic melanoma patients treated with combined immunotherapy (anti-CTLA-4+anti-PD-1), since no other data exists on primary melanoma TCFr.[32,34] TCR sequencing results of 106 patients from both studies were publicly accessible via the immuneACCESS® database[34] and GitHub[32]. Notably, the metastatic melanoma cohort had a significantly lower TCFr than our primary melanoma cohort (p=9.031E-5), with medians of 8.5% and 13.3%, respectively (FIG. 4h). This difference is consistent with our finding that patients with low TCFr are at greater risk of progression. Due to limitations in available clinical data, overall survival (rather than PFS) was the primary endpoint for this analysis and the follow-up period was limited to 30 months. In spite of these differences, applying the 20% TCFr cut-off to these metastatic melanomas still demonstrated that those with a high TCFr had a lower risk of death two years after initial treatment (HR=0.43 vs TCFr<20%, p=0.0516, LRT p=0.03; FIG. 4k).

Figure 5A:
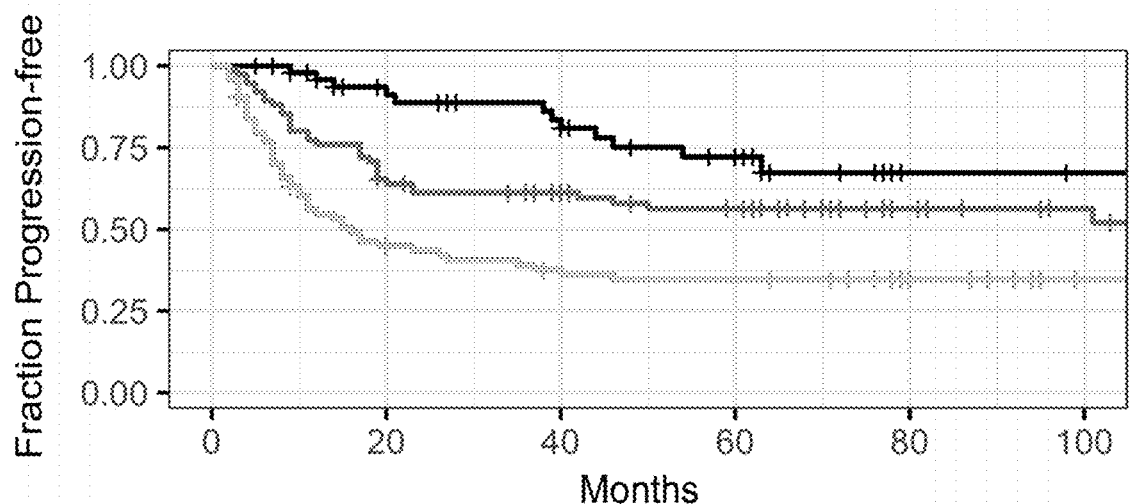
FIGS. 5A-D. Primary melanoma patients with low T-cell fraction are at greater risk of progression. (a-d) Cox regression estimates of progression-free survival rates according to (a) tumor thickness, (b) ulceration, (c) mitotic rate and (d) nodal disease. Model 1 (top panel in each figure) shows the Kaplan-Meier PFS curves of the histopathologic variable alone; Model 2 (bottom panel in each figure) shows the Kaplan-Meier PFS curves of the histopathologic variable with additional stratification using a 20% TCFr cut-off.
Figure 5A:
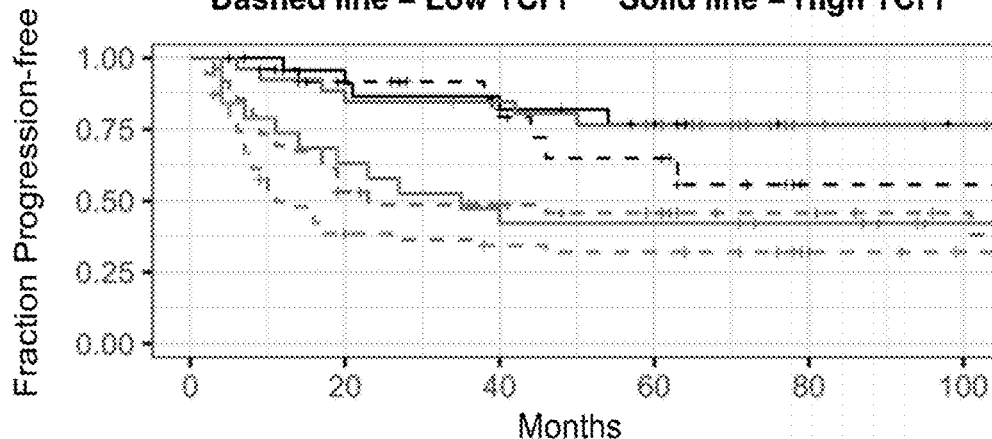

Example 5. Adding T-Cell Fraction to Breslow Thickness of Primary Melanomas Improves PFS Prediction We next calculated progression-free survival stratified by tumor thickness in a Cox Regression model. We considered either thickness group alone (model 1) or thickness group plus the 20% TCFr cut-off (model 2). The bivariate PFS prediction model of thickness group plus TCFr was significantly more accurate than thickness group alone (Analysis of Deviance/AOD, p=0.003, FIGS. 5a and 6a). The difference in PFS for patients with high (≥20%) and low (<20%) TCFr was most prominent for T3 (>2.0-4.0 mm thick) primary melanomas. Only 23.4% of T3 melanomas with high TCFr progressed in 5 years, while 54.2% of those with low TCFr (HR=0.3, p=0.007) progressed. For T3 primaries with high TCFr, the median PFS was not reached; for those with low TCFr, it was 23 months. Similarly, T4 (>4.0 mm thick) tumors with high TCFr had a median PFS of 35 months while tumors with low TCFr had a median PFS of 11 months.

Figure 5B:
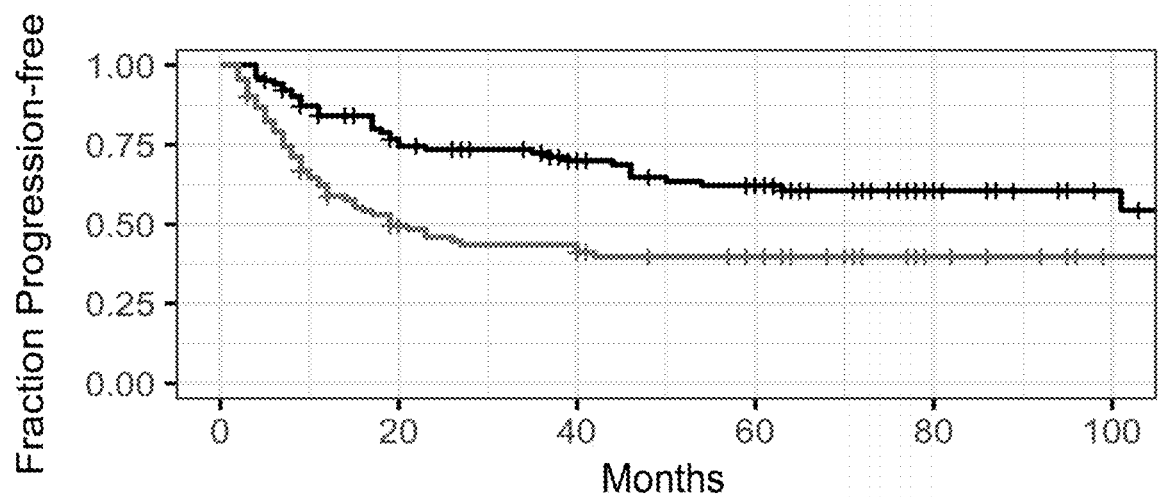
Figure 5B:
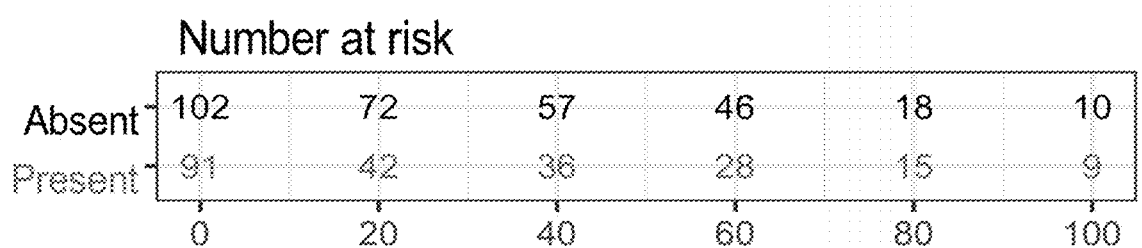
Figure 5B:
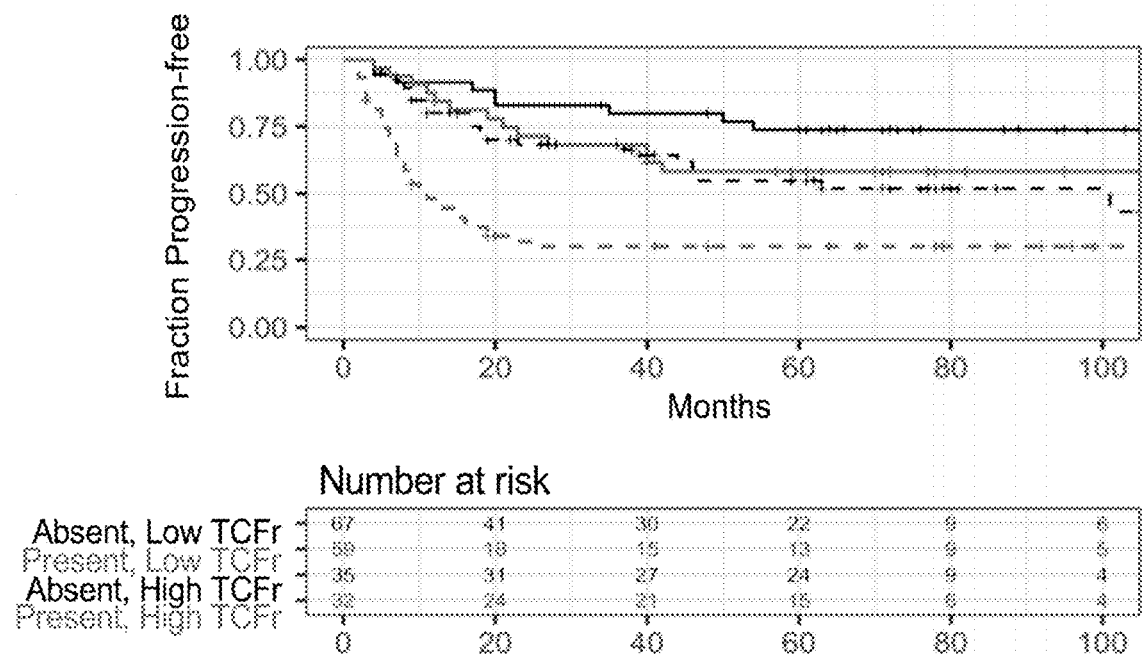

Example 6. T-Cell Fraction Modifies the Predictive Value of Other Prognostic Criteria T-cell fraction also modified other prognostic histological markers. Having a high TCFr was protective regardless of ulceration status (FIG. 5b). Patients with ulcerated tumors but high TCFr were roughly three times less likely to progress than ulcerated tumors with low TCFr (HR=0.36, p=0.00167, LRT p=8E-4). Likewise, non-ulcerated tumors with a high TCFr were more than two times less likely to recur than those with a low TCFr (HR=0.46, p=0.0443, LRT p=0.03). Of note, PFS rates of ulcerated tumors with high TCFr were equal to PFS rates of non-ulcerated tumors with low TCFr, emphasizing the value added by TCFr.

Figure 5C:
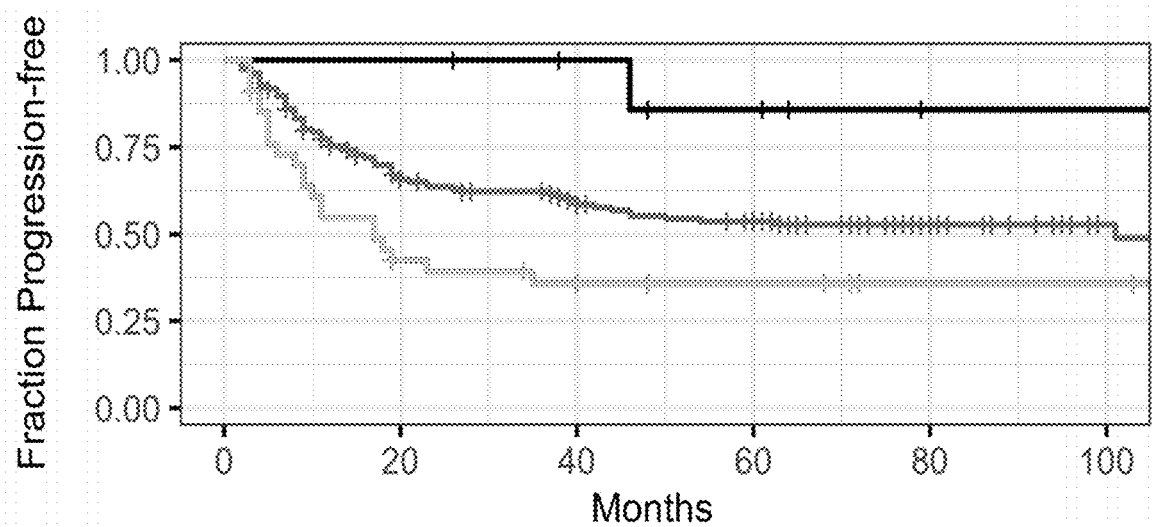
Figure 5C:
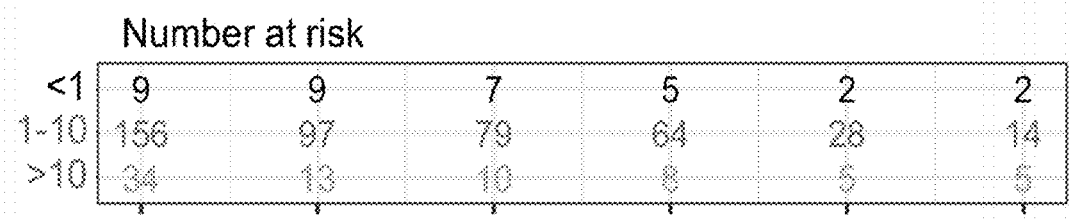
Figure 5C:
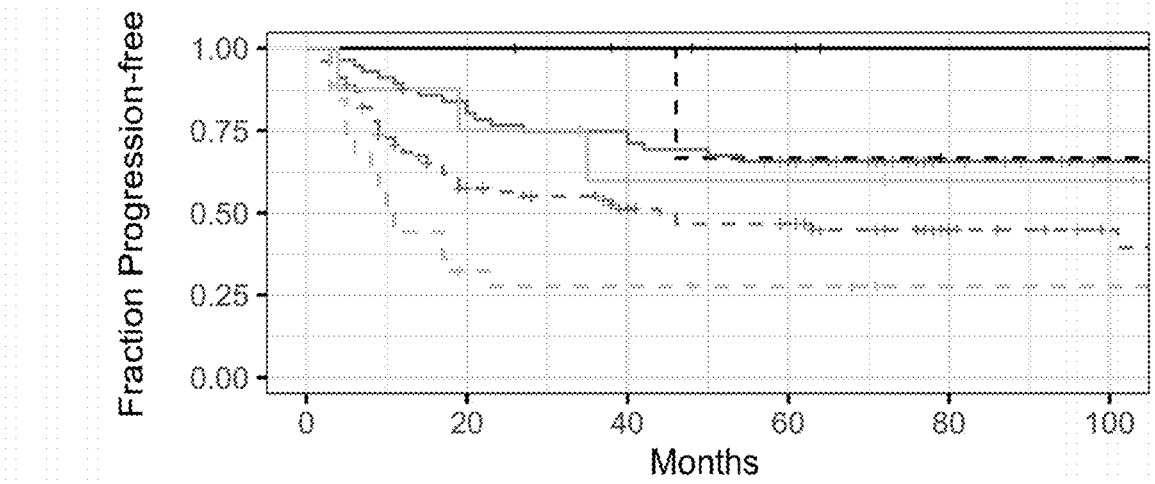
Figure 5C:
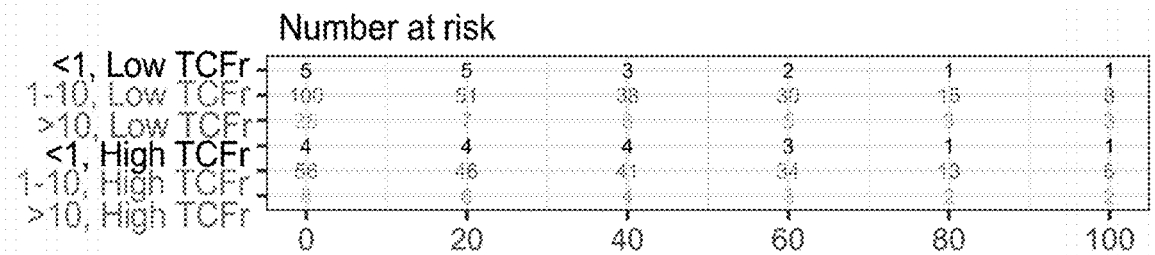

We then modelled the PFS for patients with different levels of mitoses/mm$^2$ with or without additional stratification by TCFr (FIG. 5c). As previously reported, the difference in survival was most profound when comparing patients with <1 (absent) and >10 mitoses/mm$^{2,3}$ We therefore stratified our cohort with three subgroups (<1, 1-10, >10 mitoses/mm$^2$). Again, having a high TCFr in the tumor was associated with a significantly decreased risk of melanoma progression as illustrated by Hazard Ratios of 0.49 for 1-10 mitoses/mm$^2$ (p=0.00768, LRT p=0.005) and of 0.33 for >10 mitoses/mm$^2$ (p=0.0799, LRT p=0.05) relative to a low TCFr. Too few patients had <1 mitoses/mm$^2$ to be assessed statistically.

Figure 5D:
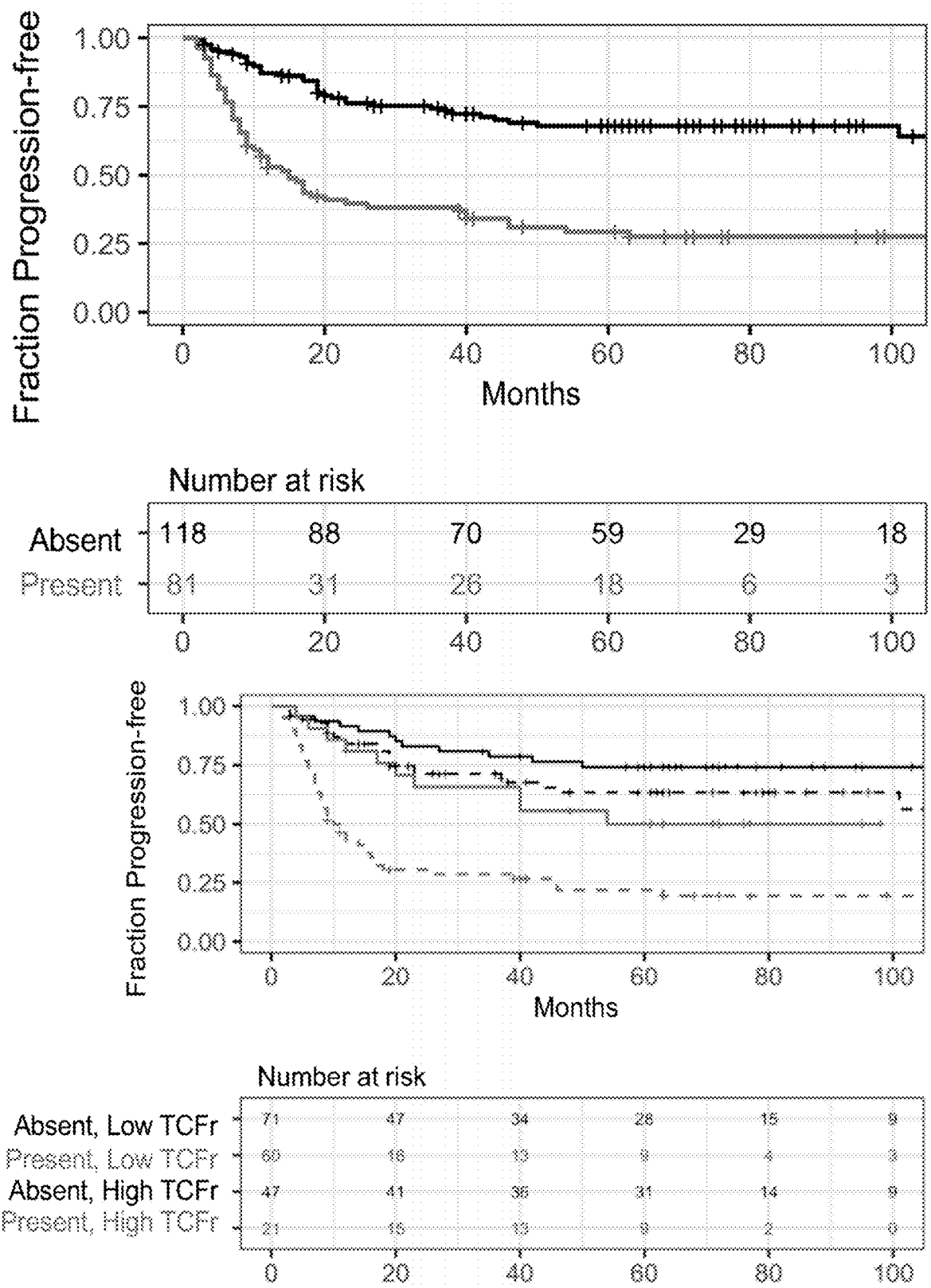

A TCFr>20% in the primary melanoma was even protective in patients who presented with tumor-positive regional lymph nodes at the initial diagnosis (FIG. 5d). Patients with resected nodal disease but high TCFr in the primary were nearly three times less likely to experience recurrence than patients with low TCFr (HR=0.37, p=0.00461, LRT p=0.002). Remarkably, PFS rates of patients with resected nodal disease but high TCFr were similar to those of patients without nodal disease but with a low TCFr.

Figures 6A, 6B:
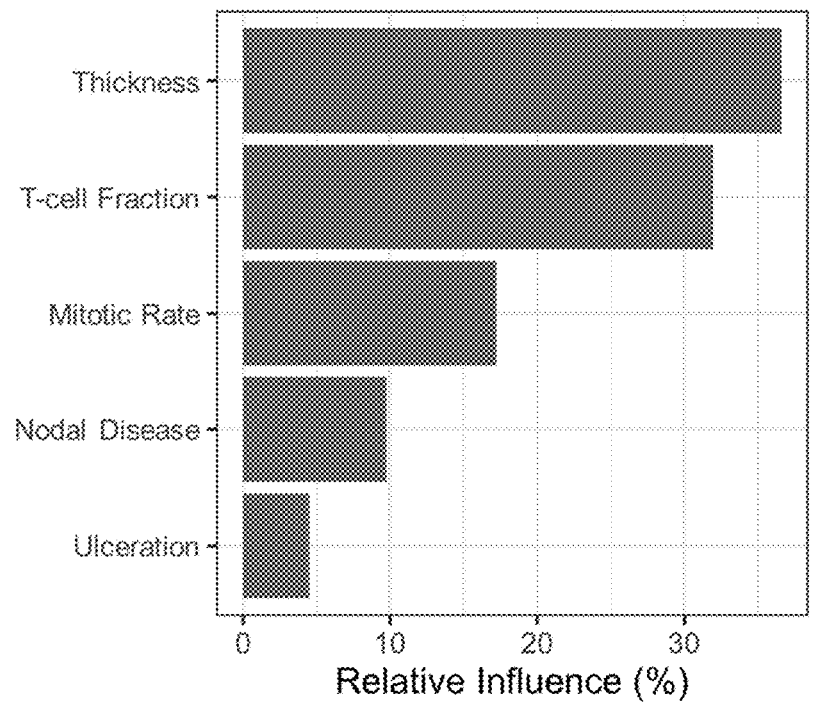
FIGS. 6A-B. PFS prediction accuracy improves when T-cell fraction is added to a histopathological feature. (a) Analysis of deviance comparing the 5-year PFS model fit for a histopathological variable alone versus a histopathological variable plus TCFr. Groups: thickness, n=199; ulceration, n=193, mitotic rate, n=193; nodal disease, n=199. Adding TCFr reduced the error in predicting recurrence for all histopathological factors (as seen by higher log-likelihood values and significant p-values). (b) Relative influence of variables on 5-year PFS prediction by gradient boosted modeling. Here, TCFr was the second most powerful predictor after tumor thickness.

Example 7. T-Cell Fraction is the Second Most Powerful Predictor after Breslow Thickness All of these histopathological variables demonstrated significantly better accuracy in their predictive power when TCFr was added to their Cox regression models (FIG. 6a). We also found that adding ulceration or mitotic rate to tumor thickness improved the accuracy of 5-year PFS predictions of disease recurrence (AOD: p=0.0251 and 0.0276, respectively) beyond thickness alone. However, when comparing the Cox regression models of tumor thickness+TCFr versus tumor thickness+ulceration or tumor thickness+mitotic rate, adding TCFr to tumor thickness was significantly more accurate (AOD: p<2.2E-16 and 0.0014, respectively).

The value of TCFr was further emphasized when we characterized the relative prognostic importance of tumor thickness, ulceration, mitotic rate, nodal disease, and TCFr in predicting disease recurrence by applying a machine-learning technique known as gradient boosting to these data.[35] This technique allowed us to assess relative variable importance by, a) how often a variable is used to split a decision tree and, b) how much a variable improves the result of each tree split. Using this approach, we determined that after tumor thickness, TCFr was the second most powerful predictor for PFS (FIG. 6b) and together, these two variables accounted for 68% of the classification power of whether a patient would experience disease progression. On the other hand, the non-independent variables associated with tumor thickness, such as ulceration, were devalued in their relative importance since they did not contribute new information to classification decisions.

Figure 7A:
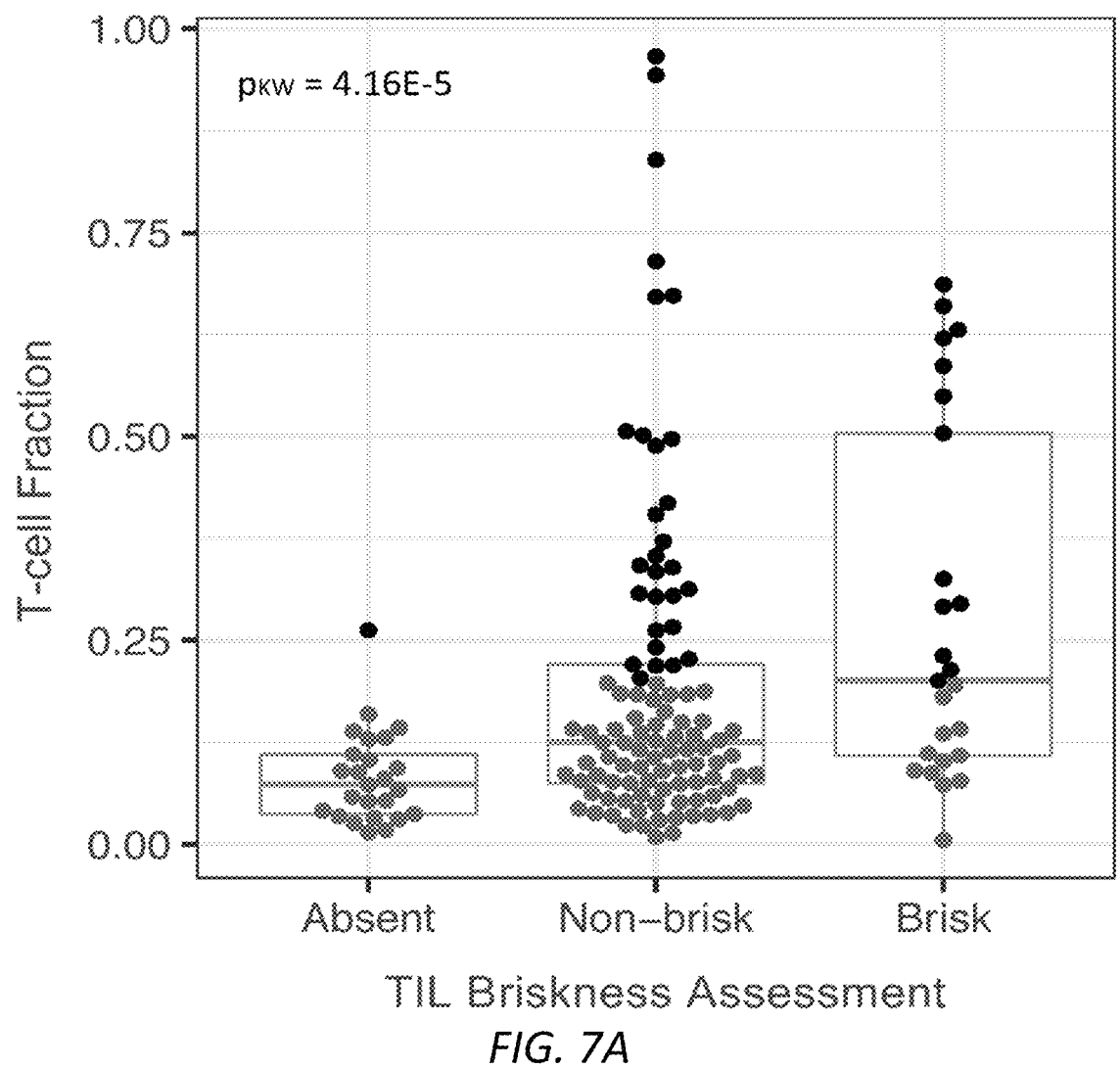
FIGS. 7A-F. Comparison of TCFr by HTS to histopathological TIL gradings. TIL reassessment with two grading systems by an experienced dermatopathologist blinded for TCR HTS results. (a,b) TCFr correlates with conventional (A, p=4.16E-5) and MIA (B, p=2.11E-7) TIL grading, but TCFr levels do not differ between MIA grade 0 and 1 as well as 2 and 3 by Kruskal-Wallis and pairwise post-hoc Kruskal-Dunn Tests. Conventional: absent, n=25; non-brisk, n=102; brisk, n=26, MIA: 0, n=25; 1, n=66; 2, n=44; 3, n=18. Box plots: the bold line indicates the median; box illustrates lower and upper quartiles; whiskers show the lowest and highest data point still within 1.5× of interquartile range from lower or upper quartile, respectively; all dots are data points. (c,d) Number of patients with low and high TCFr per TIL grading group. Bolded numbers indicate discordant labels between molecular and histopathological assessments. Discrepancies between measurements of TCFr and TIL are evident in higher grades (brisk, MIA 2/3). (e) Representative images of non-brisk and brisk graded H+E samples in accordance or discordance with TCFr measured by HTS; n=153. Non-brisk show areas of lymphocytes but also areas without any infiltration. Brisk samples are homogenously infiltrated with lymphocytes. (f) Fluorescently labeled anti-CD3 and anti-SOX-10 antibodies visualize different densities of melanoma infiltrating T cells within tumor nests for samples with low and high TCFr. Representative images shown; n=20; green=SOX10, red=CD3, blue=DAPI.
Figures 7B, 7C, 7D:
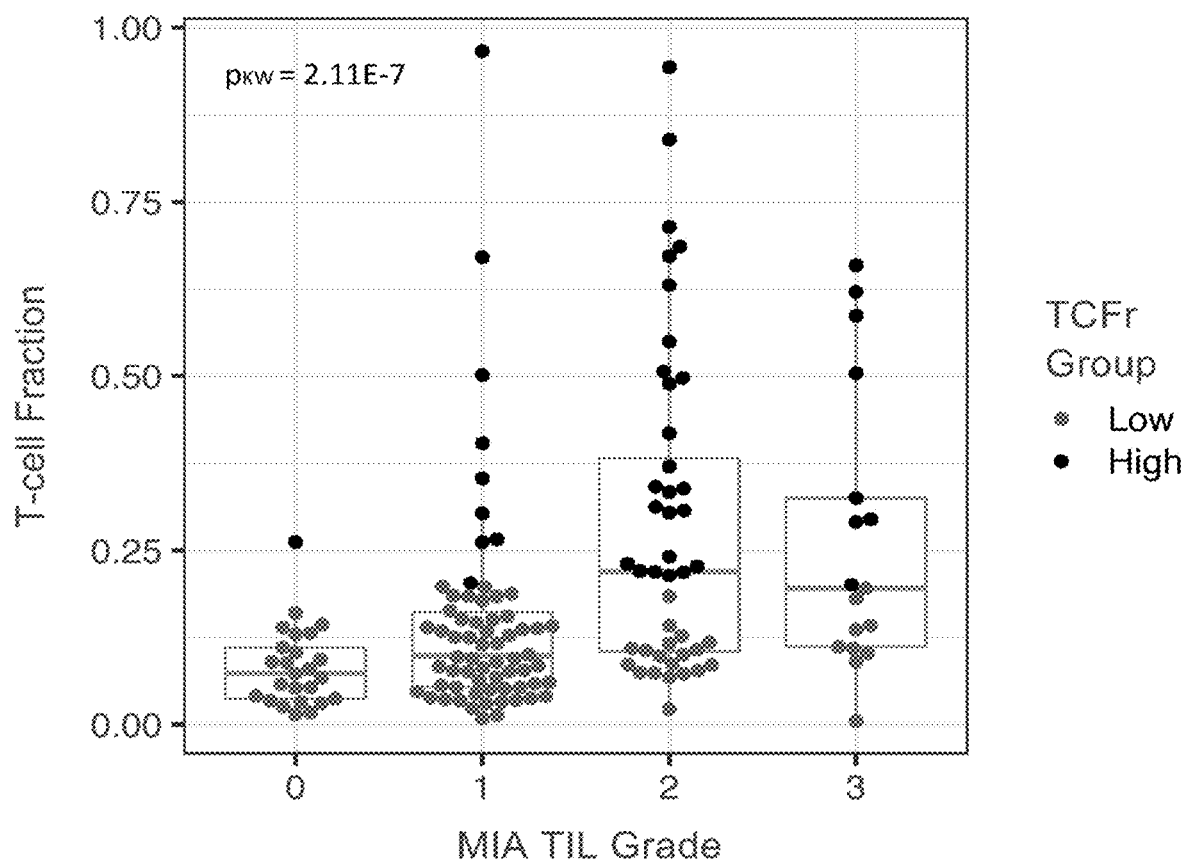
Figure 7E:
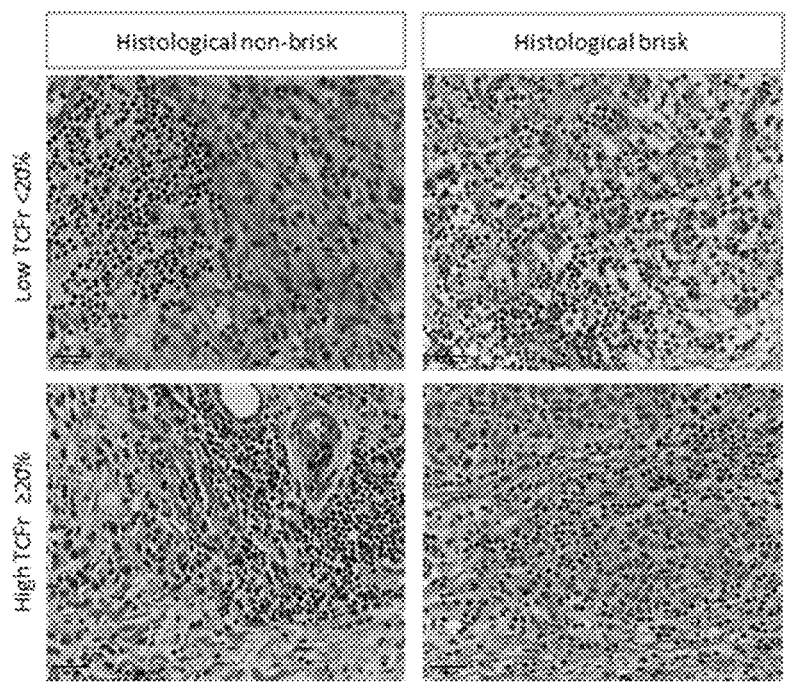
Figure 10A:
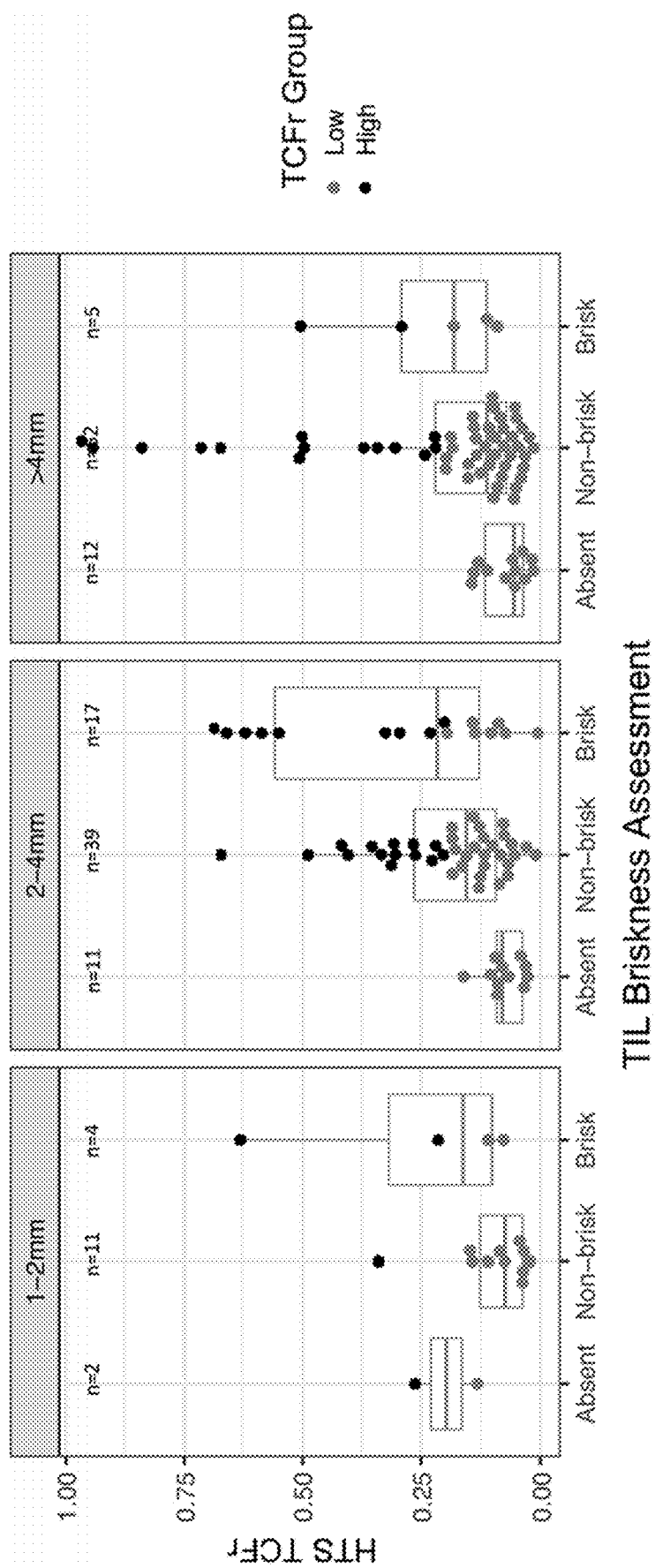
FIGS. 10A-D. Histological TIL grading. TIL regrading of samples, using two histological grading systems (n=153 primary melanoma samples). (a,b) Shown are T cell fraction per TIL grade for each thickness group. Dots for samples with low (<20%) TCFr are colorized orange, with high (≥20%) TCFr in green. Number of independent samples listed in plots. For all box plots: the bold line indicates the median; box illustrates lower and upper quartiles; whiskers show the lowest and highest data point still within 1.5× of interquartile range from lower or upper quartile, respectively; dots are data points. (c,d) Kaplan-Meier PFS curves according to (c) conventional TIL briskness assessment and (d) MIA TIL scores. Both grading systems are predictive of PFS; Cox regression with two-sided Z-test and Likelihood ratio test (LRT) (briskness: LRT p=3E-5; MIA: LRT p=0.001).
Figure 10B:
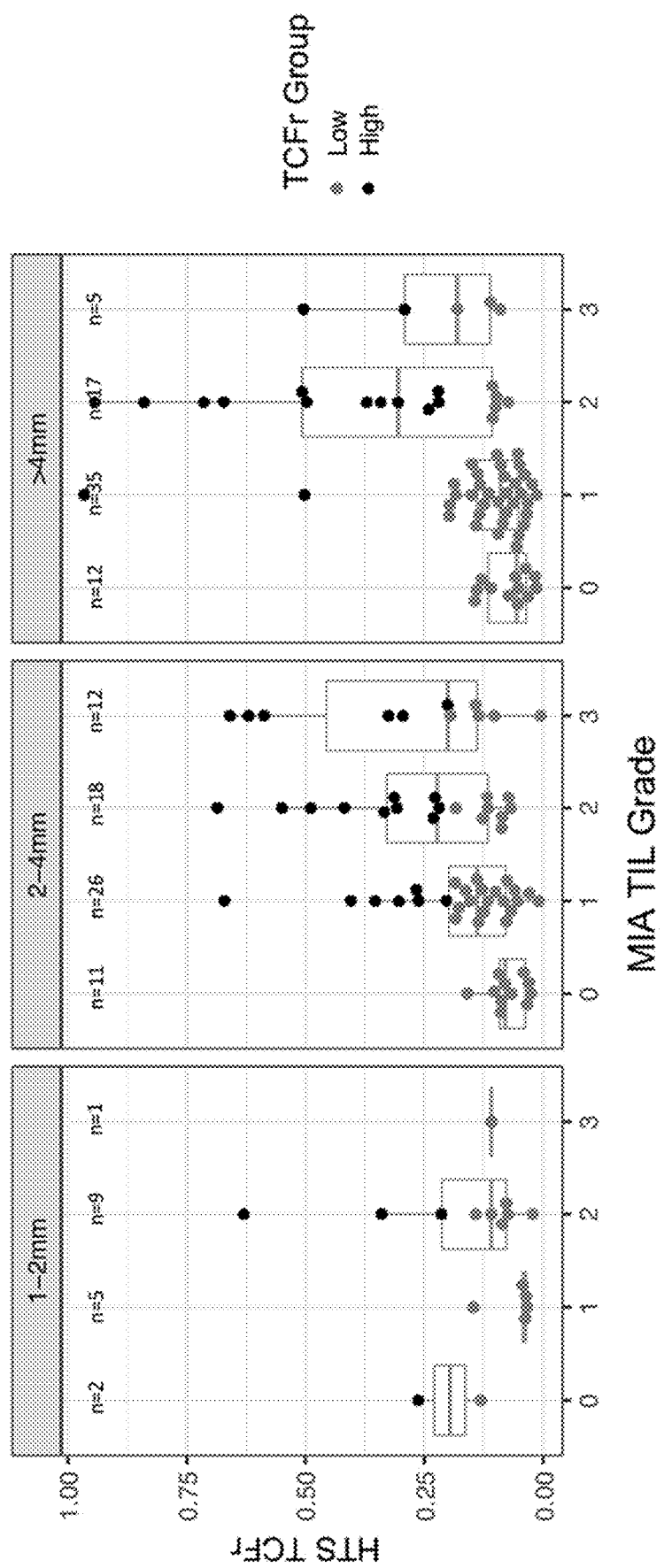
Figure 10C:
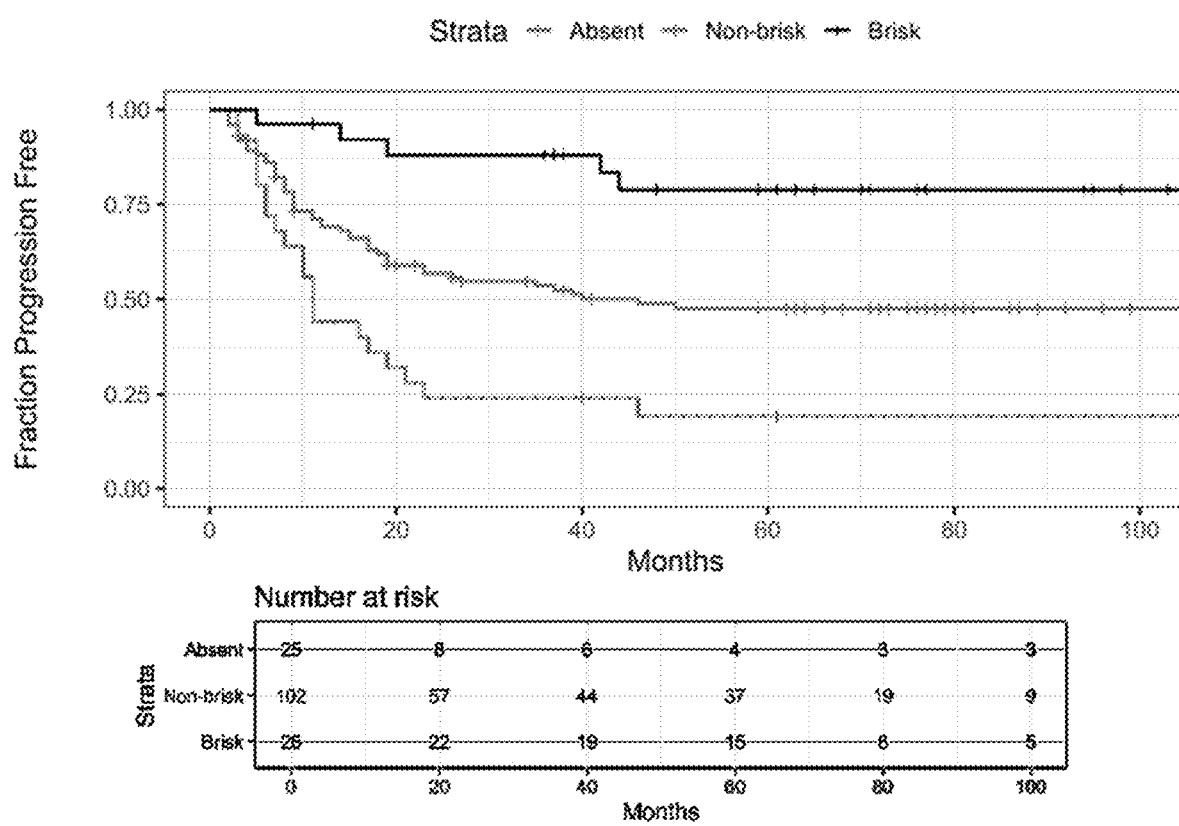
Figure 10D:
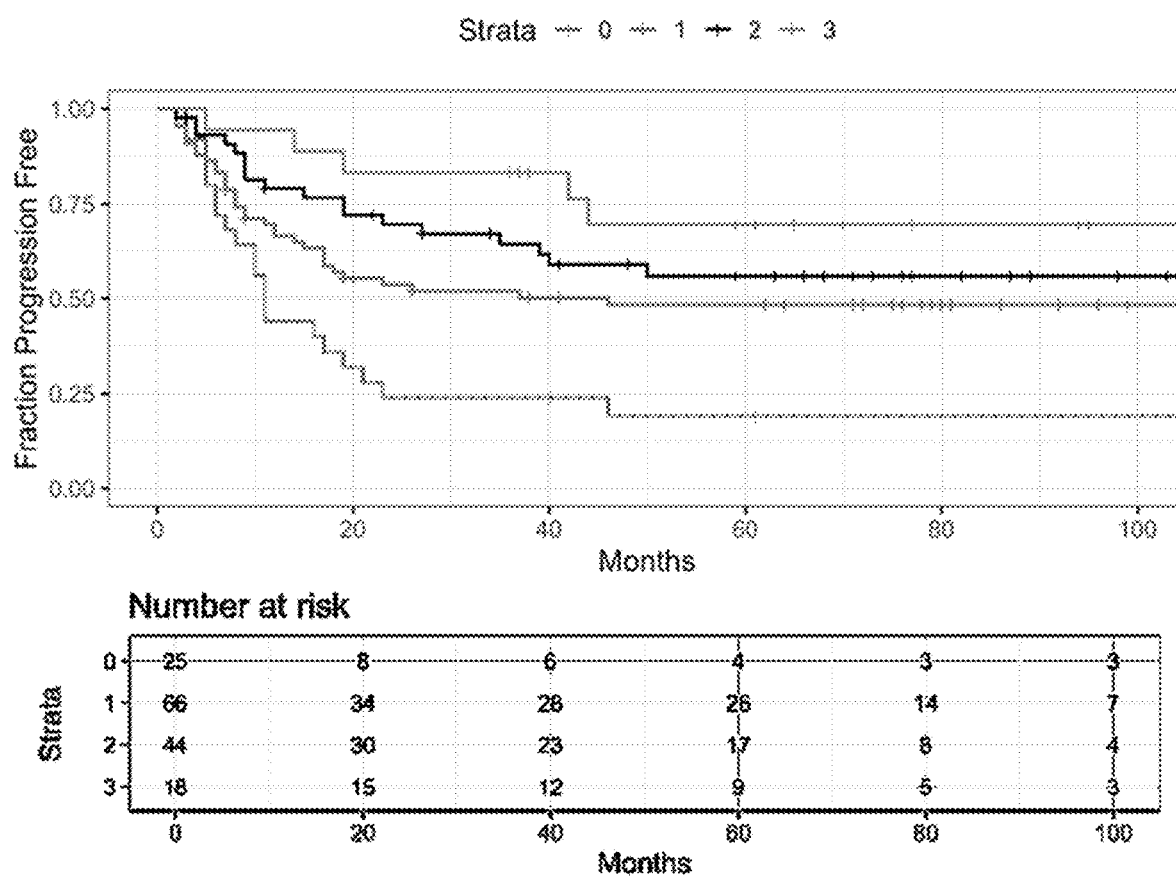

Example 8. T-Cell Fraction by HTS Outperforms Conventional Histopathological TIL Grading We next compared TCFr with conventional histopathological TIL grading for predicting patient outcome. Using the original diagnostic H+E slides, 153 samples were regraded by one experienced dermatopathologist (MCM) using two different grading systems. We first applied the conventionally used three-tiered (absent, non-brisk, and brisk) TIL classification as proposed by Clark et al. and modified by Clemente et al.[8,9] We also utilized a four-tier grading system proposed by the Melanoma Institute Australia (MIA).[10] Tumors with brisk TILs had a higher TCFr than those with non-brisk, which had a higher TCFr than those with absent TILs (all p<0.05). Similarly, higher MIA grades were associated with higher TCFr's (although MIA grades 0 vs. 1 and 2 vs. 3 had similar levels of TCFr; FIG. 7a,b, FIG. 10a,b). Conventional briskness assessment and MIA grading were highly correlated labels (p<2.3E-16) and both could partially predict progression-free survival (FIG. 10c,d). However, important discrepancies were evident between HTS and histopathological assessments, particularly for samples labelled as "brisk" and/or MIA grade 2/3. For these melanomas, the HTS-based cut-off of 20% TCFr would classify roughly half as high-risk for disease recurrence, whereas the histopathological assessment would have suggested these tumors were low-risk (FIG. 7c,d). Examples of original diagnostic H+E slides from patients with low and high TCFr in accordance or discordance with TIL assessment are shown in FIG. 7e.

Figure 7F:
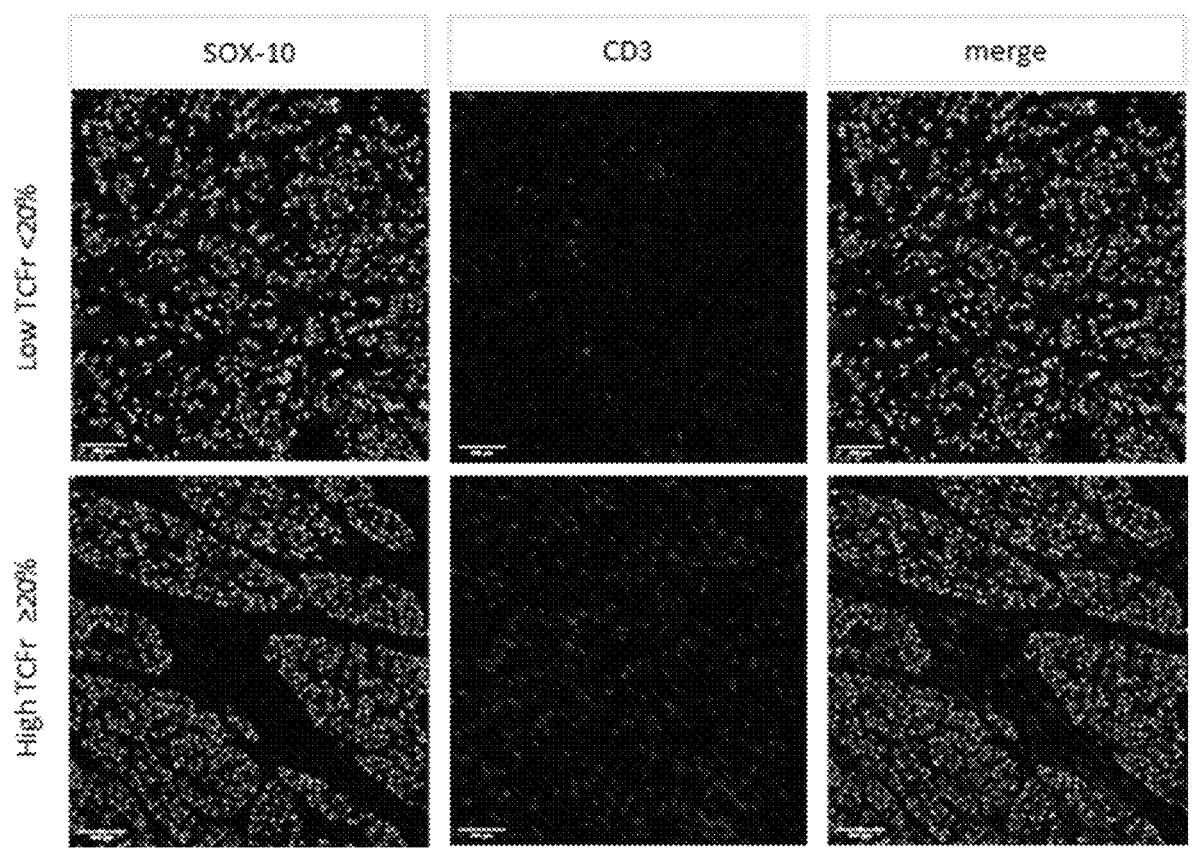

Immunofluorescence staining of a subset of our FFPE samples visualized abundant numbers of CD3+ T cells in samples with high TCFr (FIG. 7f) but only few infiltrating T cells for tumors with low TCFr. Importantly, TCFr as measured by HTS was significantly more accurate than both histopathological TIL assessments for predicting PFS at 5-years post-resection (AOD: briskness, p=0.0055; MIA grading: p=0.0031).

Figure 8A:
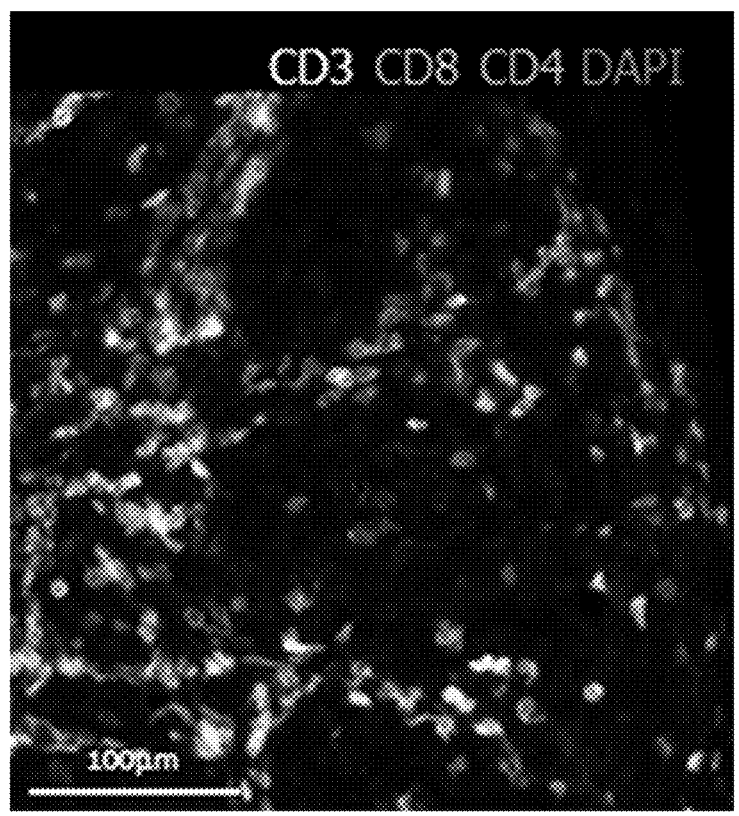
FIGS. 8A-F. Composition of the T cell infiltrate is highly variable in primary melanomas. Reassessment by multiplex immunohistochemistry to determine the relative abundance of CD3, CD8, CD4, FoxP3, CD39 and CD103. (a) Representative merged image of CD3, CD4 and CD8 staining; n=57 primary melanoma samples. (b) The amount of CD8+, CD4+FoxP3− and CD4+FoxP3+ cells is variable in both TCFr high as well as TCFr low samples independent of their recurrence status as illustrated by the stacked bar plots. (c) Representative merged image of CD8, CD39 and CD103 staining, n=57. (d) Putative tumor specific CD8+ T cells (CD8+CD39+ and CD8+CD39+CD103+) vary in frequency in both non-recurring and recurring TCFr high and TCFr low samples. (e) TCFr by HTS does not correlate with the number of CD8+, CD4+, Tregs and tumor specific CD8+ T cells (CD8+CD39+ and CD8+CD39+CD103+) in the T cell infiltrate. Line=regression line, grey shading=95% confidence interval, Spearman's correlation test; n=57. (f) Grouped boxplots of CD8+, CD4+, Tregs, CD8+CD39+ and CD8+CD39+CD103+ cells as percentage of all T cells in the infiltrate colorized by a 20% TCFr cut-off (≥20% TCFr in green, <20% TCFr in orange) and recurrence status. There is no difference in abundance of CD8+(Kruskal-Wallis Test $p_{KW}$=0.263), CD4+ ($p_{KW}$=0.263), CD8+CD39+ ($p_{KW}$=0.077) nor CD8+CD39+CD103+($p_{KW}$=0.500) between TCFr high and low samples. Tregs differed ($p_{KW}$=0.018) between the four groups since TCFr high non-recurring samples had fewer detectable CD4+FoxP3+ cells than TCFr low recurring samples two-sided Wilcoxon Rank Sum Test with post-hoc Benjamini-Hochberg correction, p=0.012). Group sizes: TCFr high non-rec, n=16, TCFr high rec, n=14; TCFr low non-rec, n=12; TCFr low rec, n=15. Box plots: the bold line indicates the median; box illustrates lower and upper quartiles; whiskers show the lowest and highest data point still within 1.5× of interquartile range from lower or upper quartile, dots are outliers.
Figure 8B:
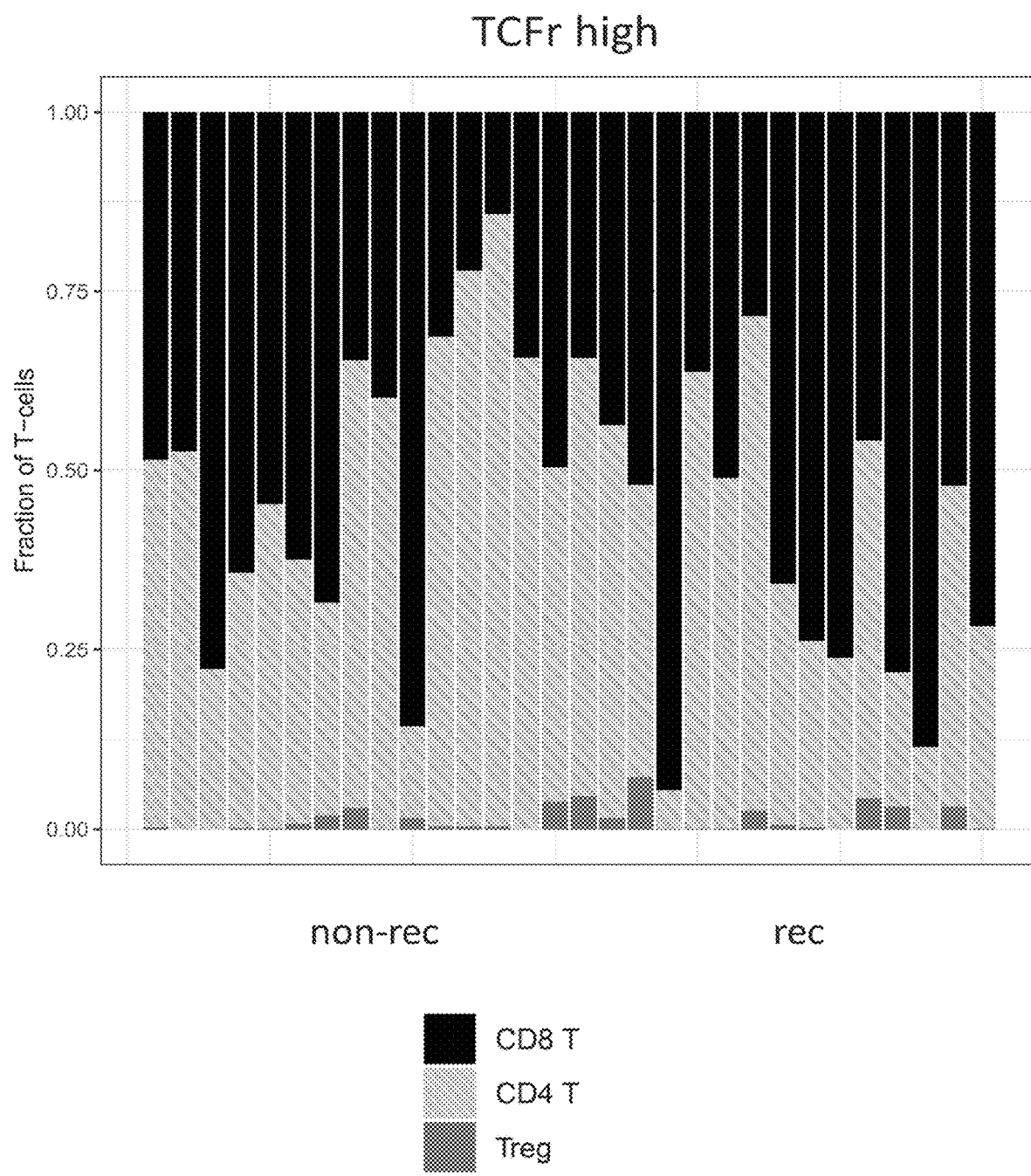
Figure 8C:
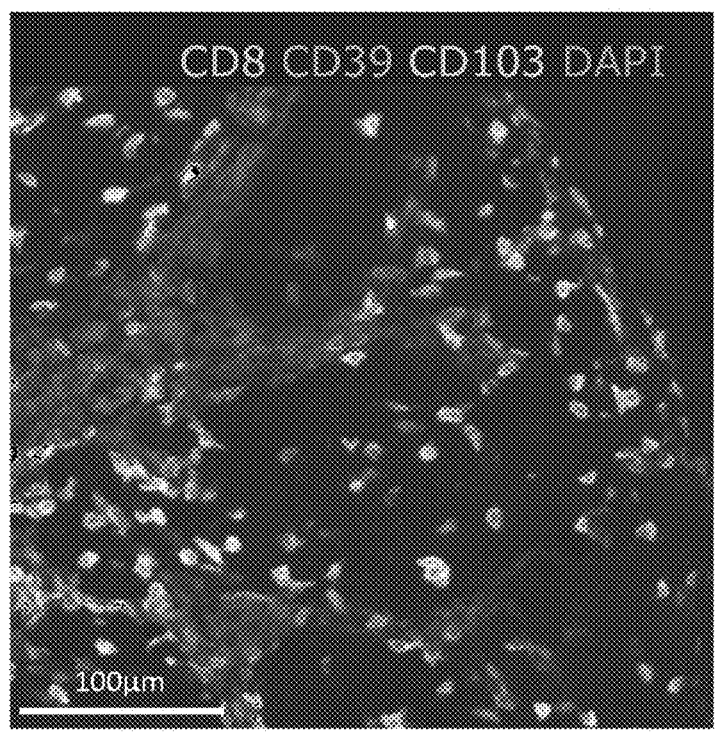
Figure 8D:
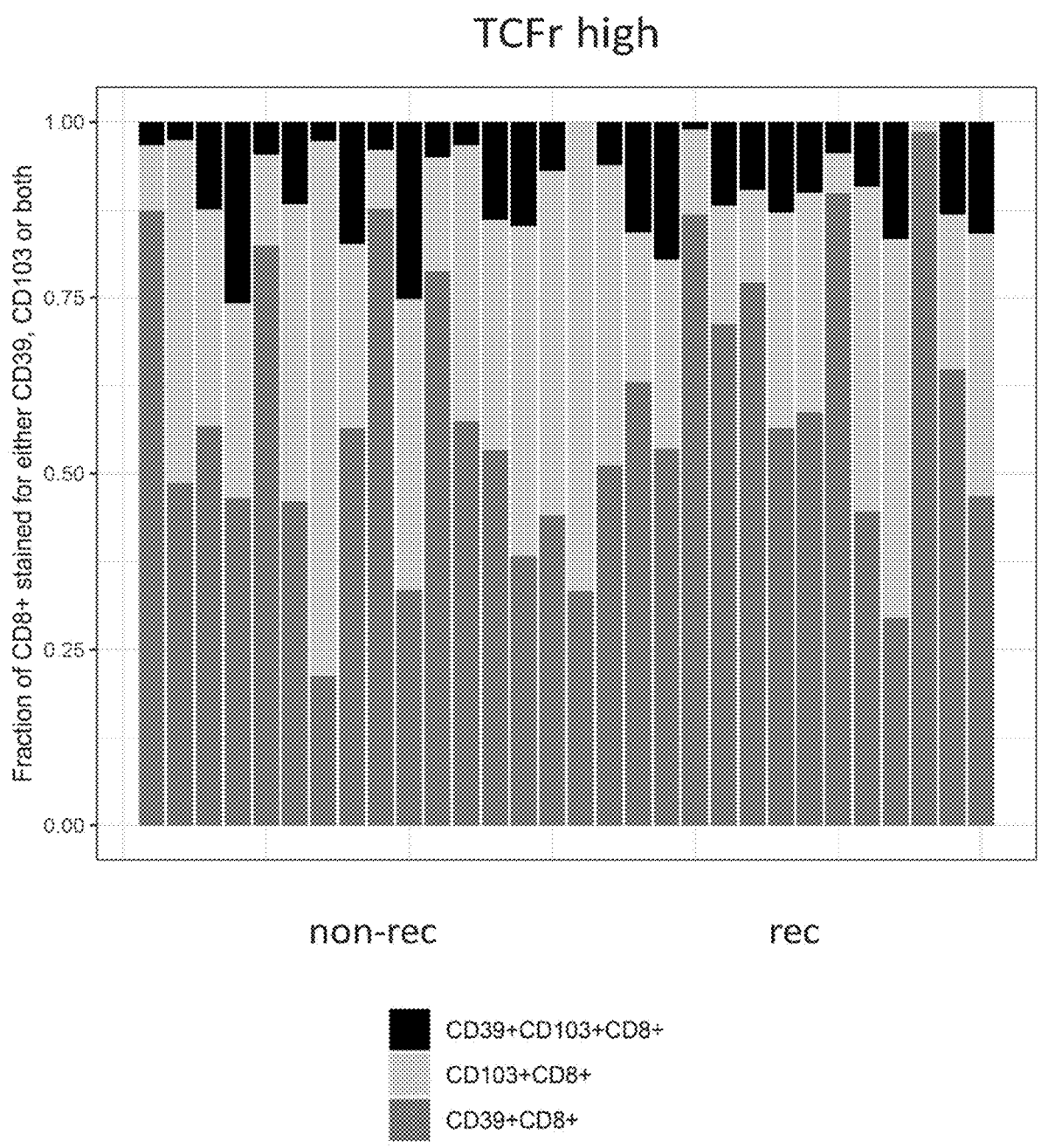
Figure 8E:
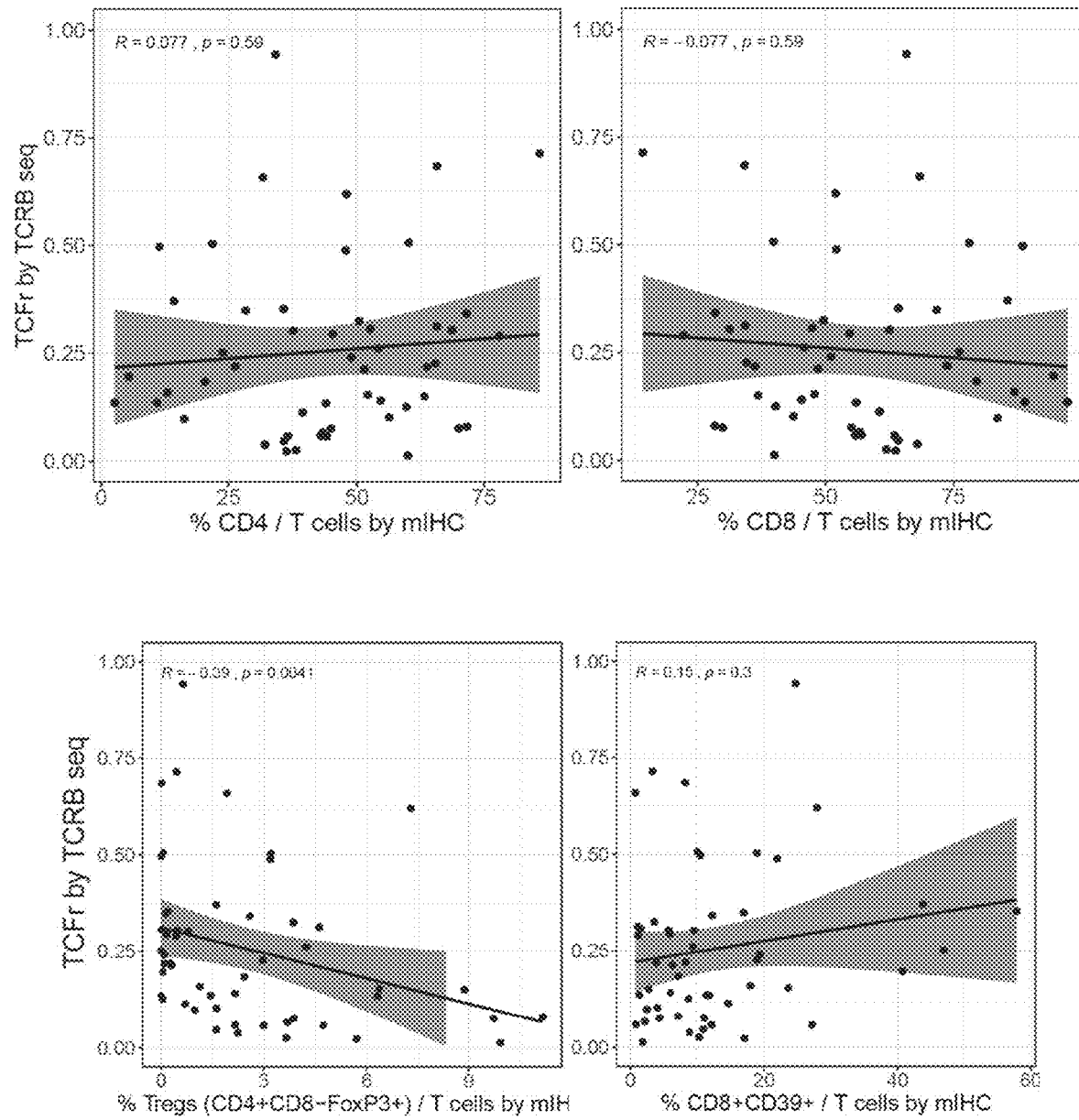
Figure 8F:
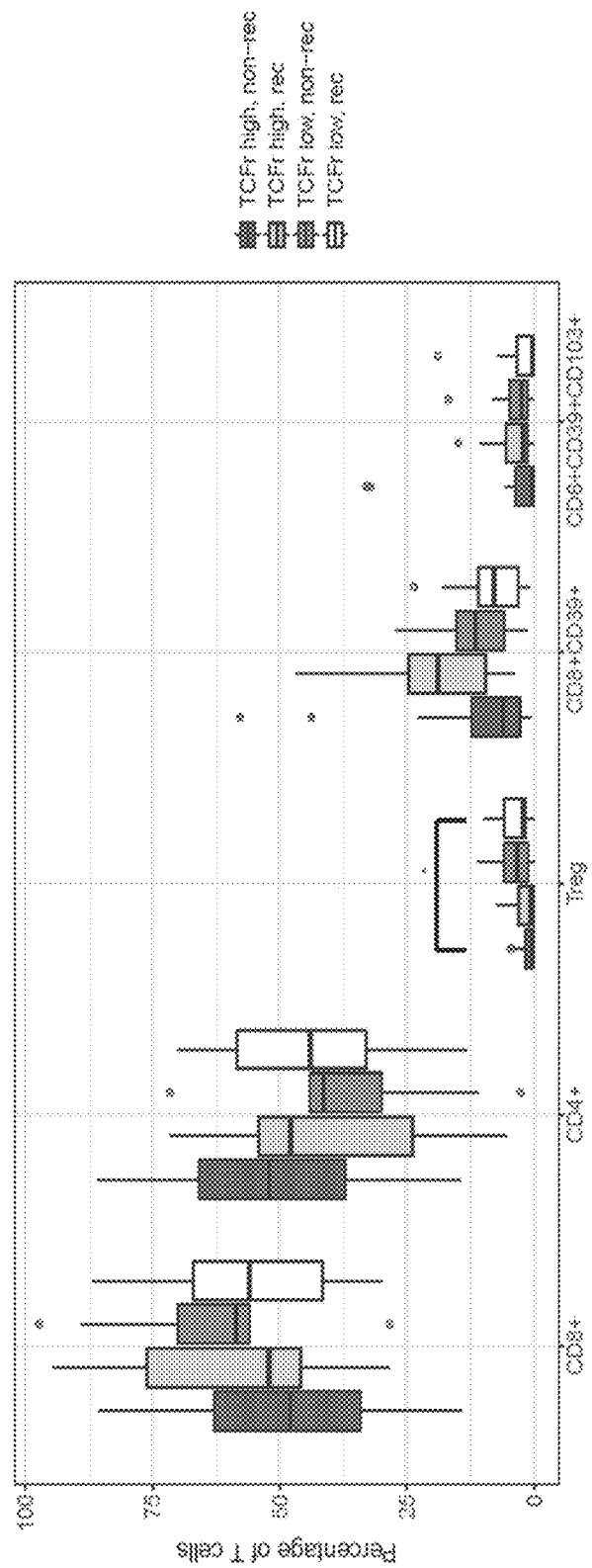
Figure 9A:
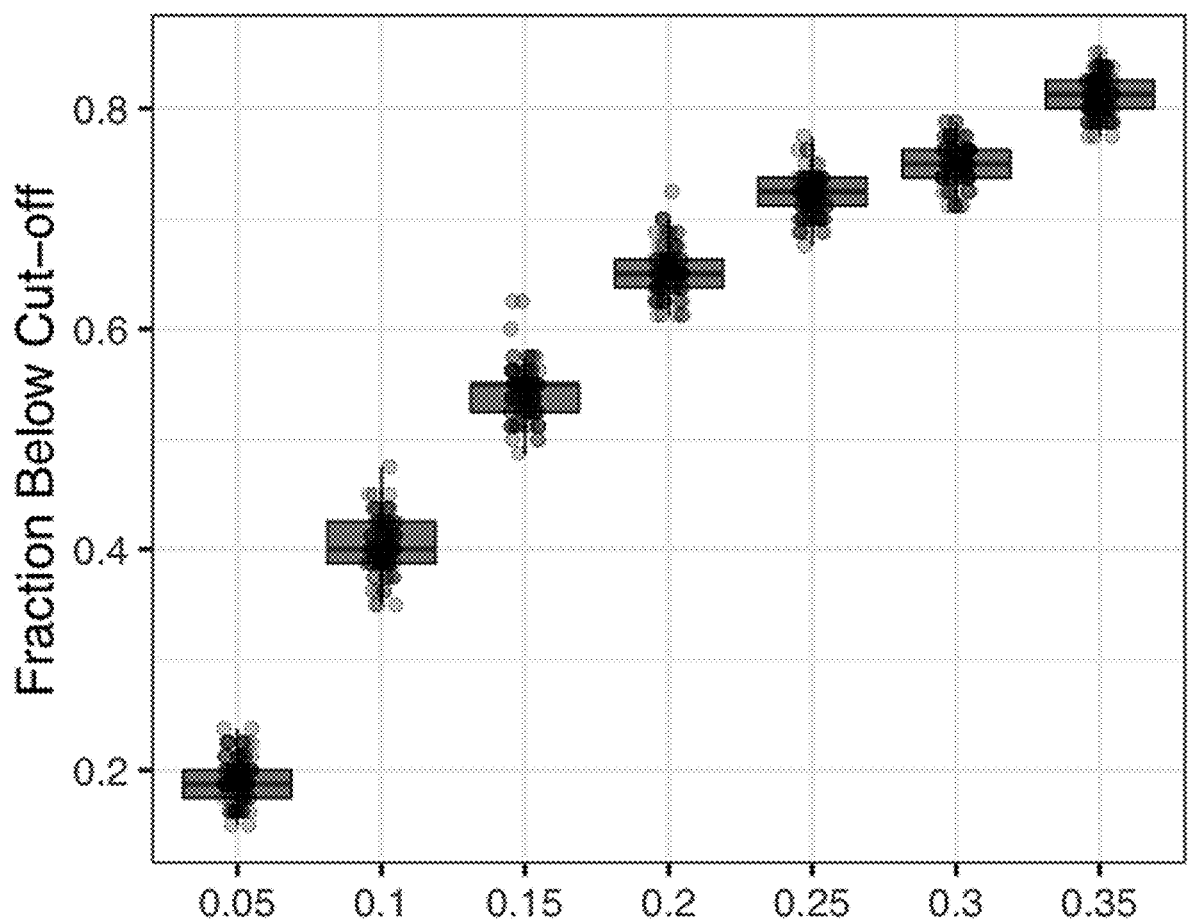
FIGS. 9A-D. TCFr cut-off benchmarking and selection. (a) Fraction below cut-off and (b) true negative rate (TNR: proportion of patients above the cut-off who remain disease-free) for seven different TCFr cut-off values as measured by bootstrapping the training group 100 times. Box plots (n=100 bootstraps): the bold line indicates the median; box illustrates lower and upper quartiles; whiskers show the lowest and highest data point still within 1.5× of interquartile range from lower or upper quartile, respectively. Each dot represents one bootstrap per TCFr value. (c) Precision-Recall Curves of 100 training cohort bootstraps colorized by TCFr cut-off (d) First order derivate of F-score versus TCFr cut-off colorized by the TPR; each dot represents one bootstrap per TCFr value, which were fitted with a LOESS curve.
Figure 9B:
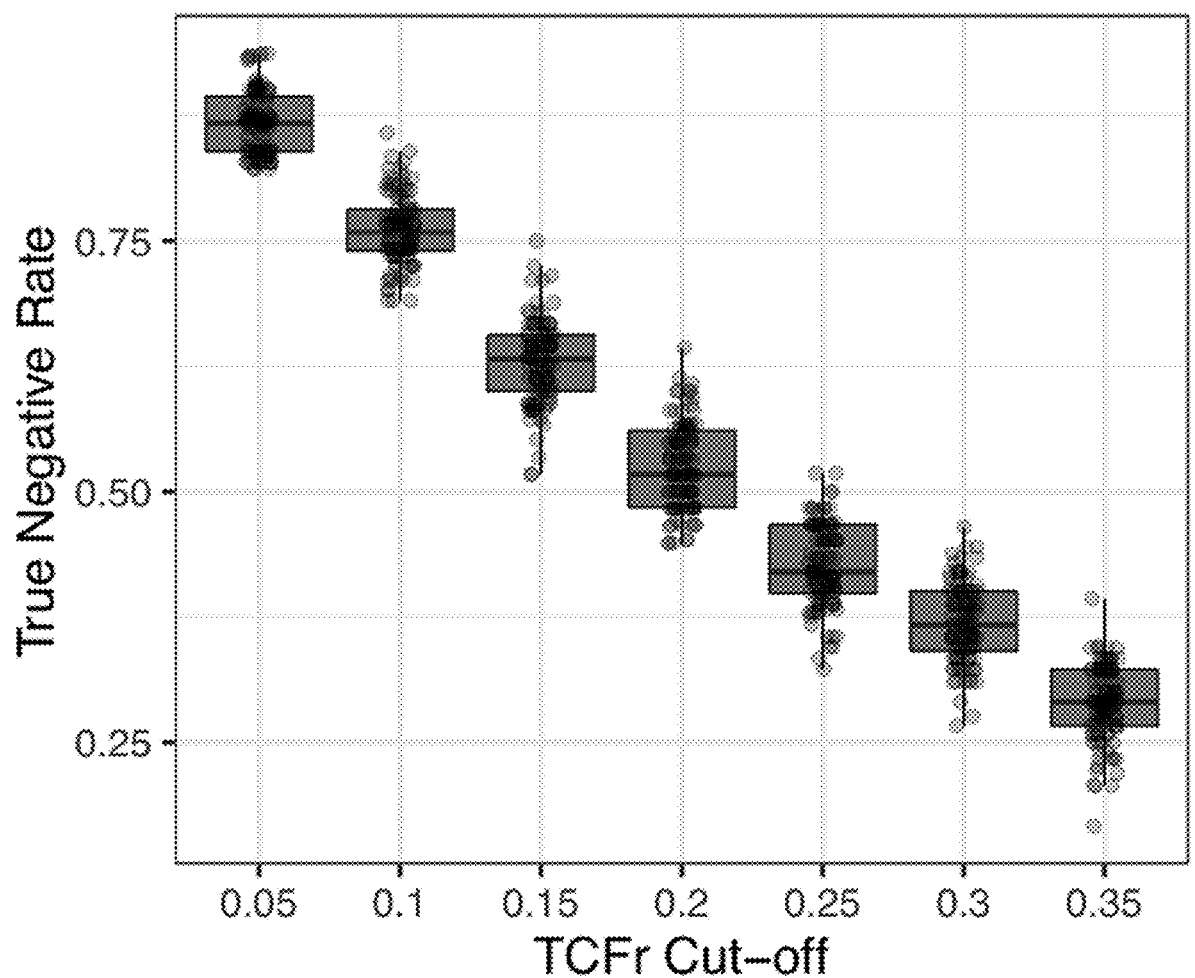
Figure 9C:
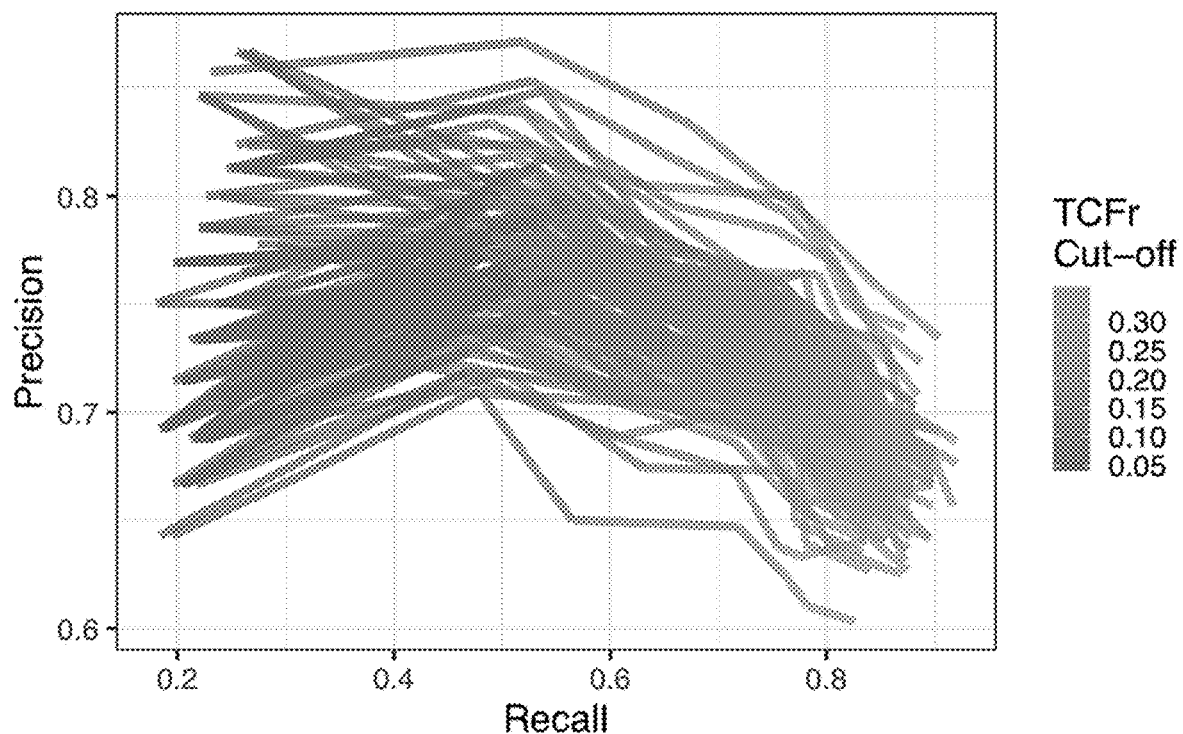
Figure 9D:
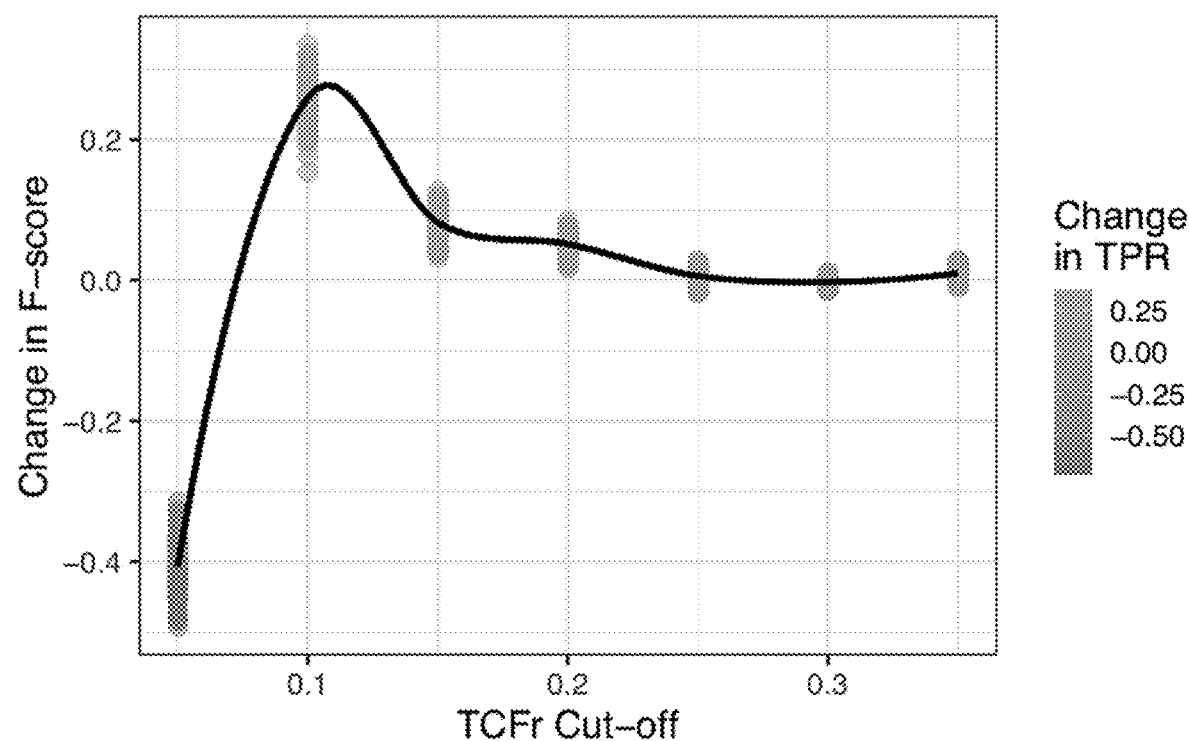
Figure 11A:
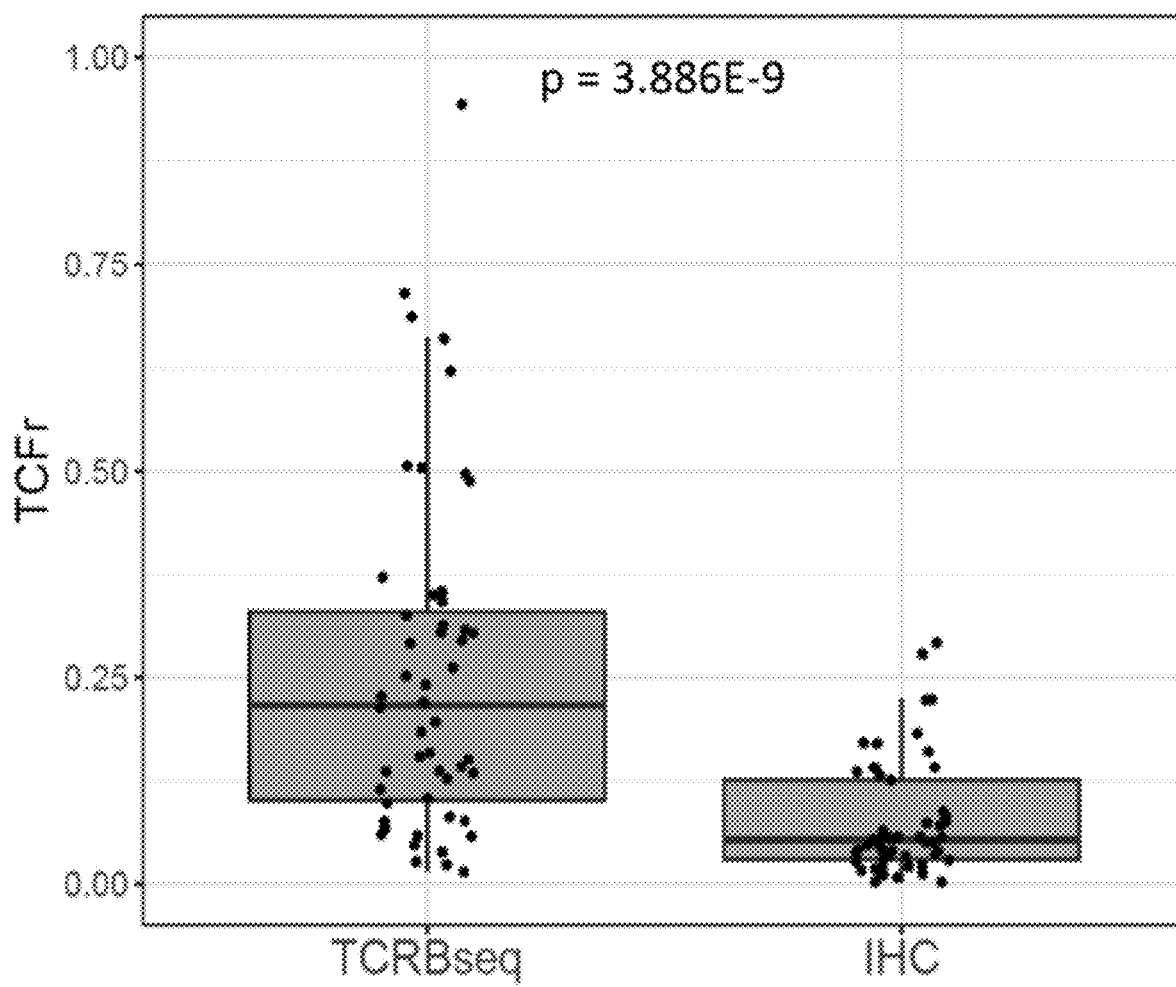
Figure 11B:
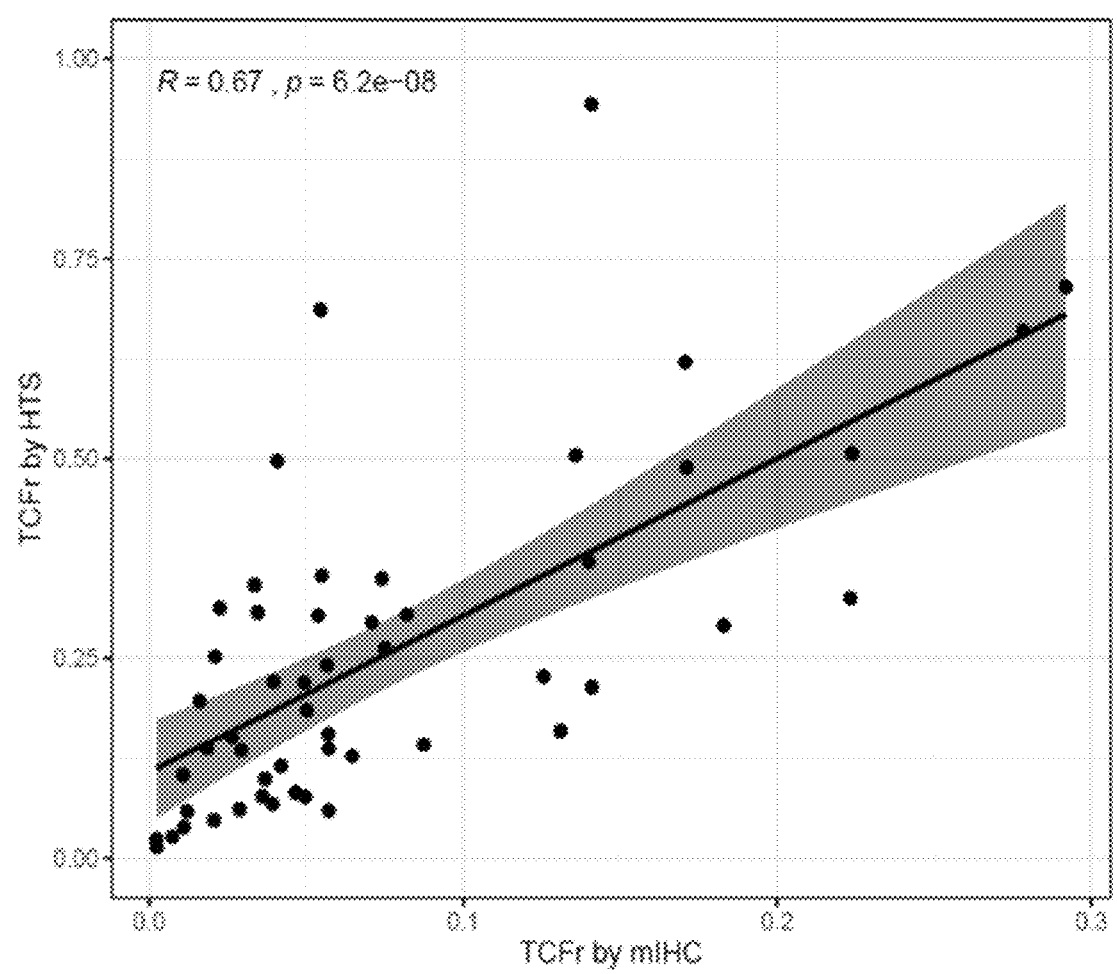

Example 9. Composition of the T Cell Infiltrate is Variable for Each Primary Melanoma To address the abundance of different T cell subsets in the infiltrate, we stained 57 samples (30 TCFr high and 27 TCFr low) which had sufficient residual tumor by multiplex immunohistochemistry (mIHC) for CD3, CD8, CD4, FoxP3, CD39 and CD103. The expression of CD39 alone and together with CD103 has been described to be upregulated on tumor antigen-specific T cells.[36,37] The median fraction of T cells was higher in the TCRB HTS than in the mIHC (median$_{HTS}$ 0.21 vs median$_{mIHC}$ 0.05, p=3.886E-9, FIG. 11a). Overall, the TCFr correlated with the ratio of CD3+ cells to DAPI positive nucleated cells as determined by mIHC (Spearman's Rho=0.67, p=6.2E-8, FIG. 11b). However, if multiple sections from one tumor were cut and stained, the number of CD3+ cells, as well as CD8+, CD4+, Tregs (CD4+CD8−FoxP3+), CD8+CD39+ and CD8+ CD39+CD103+ T cells varied greatly between the sections (FIG. 11c). The composition of the T cell infiltrate was unique for each tumor and variable in both TCFr high and TCFr low samples (FIG. 8a-d). There was no predominance of CD8+ nor CD4+ T cells, very few T regulatory cells (median 1.6% of T cells, IQR 0.2-3.7% of T cells) and varying numbers of tumor specific CD8+ T cells (median CD8+CD39+ 9.4% of T cells, IQR 4.0-17.1% of T cells). Consequently, the number of CD8+, CD4+, Tregs and tumor-specific CD8+(CD8+CD4−CD39+CD103+/−) did not correlate with TCFr by HTS (FIG. 8e). Independent of their recurrence status, TCFr high and TCFr low primary melanomas had comparable numbers of CD4+, CD8+, CD8+CD39+ and CD8+CD39+CD103+ infiltrating T cells (FIG. 8f). Tregs were less often present in non-recurring TCFr high samples than recurring TCFr low samples (p=0.012). None of the T cell subtypes was predictive of 5-year progression free survival (by univariate Cox regression).

REFERENCES

1. Matthews, N. H., Li, W. Q., Qureshi, A. A., Weinstock, M. A. & Cho, E. Epidemiology of Melanoma. in *Cutaneous Melanoma: Etiology and Therapy* (eds. Ward, W. H. & Farma, J. M.) (Codon Publications The Authors, Brisbane (AU), 2017).
2. Shaikh, W. R., et al. Melanoma Thickness and Survival Trends in the United States, 1989 to 2009. *Journal of the National Cancer Institute* 108(2016).
3. Gershenwald, J. E., et al. Melanoma staging: Evidence-based changes in the American Joint Committee on Cancer eighth edition cancer staging manual. *CA: a cancer journal for clinicians* 67, 472-492 (2017).
4. Elsaesser, O., et al. Prognosis of sentinel node staged patients with primary cutaneous melanoma. *PloS one* 7, e29791 (2012).
5. Lawrence, M. S., et al. Mutational heterogeneity in cancer and the search for new cancer-associated genes. *Nature* 499, 214-218 (2013).
6. Hayward, N. K., et al. Whole-genome landscapes of major melanoma subtypes. *Nature* 545, 175-180 (2017).
7. Snyder, A., et al. Genetic basis for clinical response to CTLA-4 blockade in melanoma. *The New England journal of medicine* 371, 2189-2199 (2014).
8. Clemente, C. G., et al. Prognostic value of tumor infiltrating lymphocytes in the vertical growth phase of primary cutaneous melanoma. *Cancer* 77, 1303-1310 (1996).
9. Clark, W. H., Jr., et al. Model predicting survival in stage I melanoma based on tumor progression. *Journal of the National Cancer Institute* 81, 1893-1904
10. Azimi, F., et al. Tumor-infiltrating lymphocyte grade is an independent predictor of sentinel lymph node status and survival in patients with cutaneous melanoma. *Journal of clinical oncology: official journal of the American Society of Clinical Oncology* 30, 2678-2683 (2012).
11. Mansson-Brahme, E., et al. Prognostic factors in thin cutaneous malignant melanoma. *Cancer* 73, 2324-2332 (1994).
12. Tuthill, R. J., Unger, J. M., Liu, P. Y., Flaherty, L. E. & Sondak, V. K. Risk assessment in localized primary cutaneous melanoma: a Southwest Oncology Group study evaluating nine factors and a test of the Clark logistic regression prediction model. *Am J Clin Pathol* 118, 504-511 (2002).
13. van Houdt, I. S., et al. Favorable outcome in clinically stage II melanoma patients is associated with the presence of activated tumor infiltrating T-lymphocytes and preserved MHC class I antigen expression. *International journal of cancer* 123, 609-615 (2008).
14. Krynitz, B., Rozell, B. L., Lyth, J., Smedby, K. E. & Lindelof, B.
Cutaneous malignant melanoma in the Swedish organ transplantation cohort: A study of clinicopathological characteristics and mortality. *J Am Acad Dermatol* 73, 106-113 e102 (2015).
15. Thomas, N. E., et al. Tumor-infiltrating lymphocyte grade in primary melanomas is independently associated with melanoma-specific survival in the population-based genes, environment and melanoma study. *J Clin Oncol* 31, 4252-4259 (2013).

16. Burton, A. L., et al. Prognostic significance of tumor infiltrating lymphocytes in melanoma. *Am Surg* 77, 188-192 (2011).
17. Kruper, L. L., et al. Predicting sentinel node status in AJCC stage I/II primary cutaneous melanoma. *Cancer* 107, 2436-2445 (2006).
18. Taylor, R. C., Patel, A., Panageas, K. S., Busam, K. J. & Brady, M. S. Tumor-infiltrating lymphocytes predict sentinel lymph node positivity in patients with cutaneous melanoma. *J Clin Oncol* 25, 869-875 (2007).
19. Mandala, M., et al. Clinical and histopathological risk factors to predict sentinel lymph node positivity, disease-free and overall survival in clinical stages I-II AJCC skin melanoma: outcome analysis from a single-institution prospectively collected database. *Eur J Cancer* 45, 2537-2545 (2009).
20. Donizy, P., et al. Paucity of tumor-infiltrating lymphocytes is an unfavorable prognosticator and predicts lymph node metastases in cutaneous melanoma patients. *Anticancer Res* 35, 351-358 (2015).
21. Thorn, M., Ponten, F., Bergstrom, R., Sparen, P. & Adami, H. O. Clinical and histopathologic predictors of survival in patients with malignant melanoma: a population-based study in Sweden. *J Natl Cancer Inst* 86, 761-769 (1994).
22. Barnhill, R. L., Fine, J. A., Roush, G. C. & Berwick, M. Predicting five-year outcome for patients with cutaneous melanoma in a population-based study. *Cancer* 78, 427-432 (1996).
23. Saldanha, G., Flatman, K., Teo, K. W. & Bamford, M. A Novel Numerical Scoring System for Melanoma Tumor-infiltrating Lymphocytes Has Better Prognostic Value Than Standard Scoring. *The American journal of surgical pathology* 41, 906-914 (2017).
24. Larkin, J., et al. Combined Nivolumab and Ipilimumab or Monotherapy in Untreated Melanoma. *The New England journal of medicine* 373, 23-34 (2015).
25. Prieto, P. A., et al. CTLA-4 blockade with ipilimumab: long-term follow-up of 177 patients with metastatic melanoma. *Clin Cancer Res* 18, 2039-2047 (2012).
26. Hogan, S. A., Levesque, M. P. & Cheng, P. F. Melanoma Immunotherapy: Next-Generation Biomarkers. *Front Oncol* 8, 178 (2018).
27. Robert, L., et al. Distinct immunological mechanisms of CTLA-4 and PD-1 blockade revealed by analyzing TCR usage in blood lymphocytes. *Oncoimmunology* 3, e29244 (2014).
28. Postow, M. A., et al. Peripheral T cell receptor diversity is associated with clinical outcomes following ipilimumab treatment in metastatic melanoma. *Journal for immunotherapy of cancer* 3, 23 (2015).
29. Cha, E., et al. Improved survival with T cell clonotype stability after anti-CTLA-4 treatment in cancer patients. *Science translational medicine* 6, 238ra270 (2014).
30. Tumeh, P. C., et al. PD-1 blockade induces responses by inhibiting adaptive immune resistance. *Nature* 515, 568-571 (2014).
31. Roh, W., et al. Integrated molecular analysis of tumor biopsies on sequential CTLA-4 and PD-1 blockade reveals markers of response and resistance. *Sci Transl Med* 9(2017).
32. Riaz, N., et al. Tumor and Microenvironment Evolution during Immunotherapy with Nivolumab. *Cell* 171, 934-949 e915 (2017).
33. Inoue, H., et al. Intratumoral expression levels of PD-L1, GZMA, and HLA-A along with oligoclonal T cell expansion associate with response to nivolumab in metastatic melanoma. *Oncoimmunology* 5, e1204507 (2016).
34. Yusko, E., et al. Association of Tumor Microenvironment T-*Cell* Repertoire and Mutational Load With Clinical Outcome After Sequential Checkpoint Blockade in Melanoma. *Cancer Immunol Res* (2019).
35. Elith, J., Leathwick, J. R. & Hastie, T. A working guide to boosted regression trees. *The Journal of animal ecology* 77, 802-813 (2008).
36. Simoni, Y., et al. Bystander CD8(+) T cells are abundant and phenotypically distinct in human tumour infiltrates. *Nature* 557, 575-579 (2018).
37. Duhen, T., et al. Co-expression of CD39 and CD103 identifies tumor-reactive CD8 T cells in human solid tumors. *Nature communications* 9, 2724 (2018).
38. Vasaturo, A., et al. T-cell Landscape in a Primary Melanoma Predicts the Survival of Patients with Metastatic Disease after Their Treatment with Dendritic *Cell* Vaccines. *Cancer research* 76, 3496-3506 (2016).
39. Nsengimana, J., et al. beta-Catenin-mediated immune evasion pathway frequently operates in primary cutaneous melanomas. *The Journal of clinical investigation* 128, 2048-2063 (2018).
40. Scheper, W., et al. Low and variable tumor reactivity of the intratumoral TCR repertoire in human cancers. *Nature medicine* 25, 89-94 (2019).
41. Rosato, P. C., et al. Virus-specific memory T cells populate tumors and can be repurposed for tumor immunotherapy. *Nature communications* 10, 567 (2019).
42. Camisaschi, C., Vallacchi, V., Castelli, C., Rivoltini, L. & Rodolfo, M. Immune cells in the melanoma microenvironment hold information for prediction of the risk of recurrence and response to treatment. *Expert review of molecular diagnostics* 14,
43. Ladanyi, A., et al. T-cell activation marker expression on tumor-infiltrating lymphocytes as prognostic factor in cutaneous malignant melanoma. *Clinical cancer research: an official journal of the American Association for Cancer Research* 10, 521-530 (2004).
44. Park, C. K. & Kim, S. K. Clinicopathological significance of intratumoral and peritumoral lymphocytes and lymphocyte score based on the histologic subtypes of cutaneous melanoma. *Oncotarget* 8, 14759-14769 (2017).
45. Huang, A. C., et al. A single dose of neoadjuvant PD-1 blockade predicts clinical outcomes in resectable melanoma. *Nature medicine* 25, 454-461 (2019).
46. Carlson, C. S., et al. Using synthetic templates to design an unbiased multiplex PCR assay. *Nature communications* 4, 2680 (2013).
47. Robins, H. S., et al. Comprehensive assessment of T-cell receptor beta-chain diversity in alphabeta T cells. *Blood* 114, 4099-4107 (2009).
48. RCoreTeam. R: A language and environment for statistical computing. *R Foundation for Statistical Computing*, Vienna, Austria. (2017).
49. McShane, L. M., et al. Reporting recommendations for tumor marker prognostic studies (REMARK). *Journal of the National Cancer Institute* 97, 1180-1184 (2005).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating a subject who has primary melanoma, wherein the primary melanoma is cutaneous melanoma and is stage I to IIC, the method comprising:
   obtaining a biopsy sample from the primary melanoma;
   determining the T cell fraction (TCFr) of said sample, wherein determining the TCFr comprises analyzing T-cell receptor beta (TCR β) gene sequences in substantially every T cell in the sample, and quantitating total nucleated cells and calculating the proportion of T cells in the sample relative to its total number of nucleated cells;
   selecting a subject with TCFr below 20% for an aggressive treatment; and
   treating said subject with the aggressive treatment, wherein the aggressive treatment is targeted treatment, immunotherapy, chemotherapy, and/or radiation, or a combination thereof.

2. The method of claim 1, wherein the primary melanoma is 1-4 mm thick.

3. The method of claim 1, wherein said analyzing is performed by high-throughput DNA sequencing.

4. The method of claim 1, wherein the chemotherapy comprises administration of one or more nitrosoureas; alkylating agents; microtubule targeting agents; or platinum-containing agents.

5. The method of claim 1, wherein the targeted treatment comprises a BRAF inhibitor and/or a MEK inhibitor.

6. The method of claim 1, wherein the immunotherapy comprises administration of a checkpoint inhibitor.

7. The method of claim 1, wherein the immunotherapy comprises administration of a vaccine targeting melanoma cells, peptide-based vaccine, viral vector-based vaccine, or dendritic cell vaccine.

* * * * *